(12) United States Patent
Beck et al.

(10) Patent No.: US 9,694,006 B2
(45) Date of Patent: *Jul. 4, 2017

(54) USE OF PYRROLOQUINOLINE COMPOUNDS TO KILL CLINICALLY LATENT MICROORGANISMS

(75) Inventors: Petra Helga Beck, Oxfordshire (GB); Marc Barry Brown, Oxfordshire (GB); David Edward Clark, Essex (GB); Anthony Coates, London (GB); Hazel Joan Dyke, Essex (GB); Yanmin Hu, London (GB); Derek John Londesbrough, Sunderland (GB); Keith Mills, Hertfordshire (GB); Thomas David Pallin, Essex (GB); Gary Patrick Reid, Sunderland (GB); Gerlinda Stoddart, Oxfordshire (GB)

(73) Assignee: HELPERBY THERAPEUTICS LIMITED, North Yorks (GB)

(*) Notice: Subject to any disclaimer, the term of this patent is extended or adjusted under 35 U.S.C. 154(b) by 663 days.

This patent is subject to a terminal disclaimer.

(21) Appl. No.: 13/473,707

(22) Filed: May 17, 2012

(65) Prior Publication Data

US 2012/0231995 A1 Sep. 13, 2012

Related U.S. Application Data

(62) Division of application No. 12/092,947, filed as application No. PCT/GB2006/004178 on Nov. 8, 2006, now Pat. No. 8,207,187.

(30) Foreign Application Priority Data

Nov. 8, 2005 (GB) .................................. 0522715.2

(51) Int. Cl.
*A61K 31/4745* (2006.01)
*A61K 31/4439* (2006.01)
*C07D 471/04* (2006.01)

(52) U.S. Cl.
CPC ...... *A61K 31/4745* (2013.01); *A61K 31/4439* (2013.01); *C07D 471/04* (2013.01)

(58) Field of Classification Search
None
See application file for complete search history.

(56) References Cited

U.S. PATENT DOCUMENTS 2,623,878 A 12/1952 Isler et al.
2,691,023 A 10/1954 Horlein et al.
(Continued)

FOREIGN PATENT DOCUMENTS

EP 0226508 A1 6/1987
EP 0 307 078 A1 3/1989
(Continued)

OTHER PUBLICATIONS

Badawey et al., "Potential antineoplastics. Synthesis and cytotoxicity of certain 4-chloro-3-(2-chloroethyl)-2-methylquinolines and related derivatives," Eur. J. Med. Chem., vol. 32, No. 10, 1997, pp. 815-822.

(Continued)

*Primary Examiner* — Bethany Barham
*Assistant Examiner* — Barbara Frazier
(74) *Attorney, Agent, or Firm* — Sughrue Mion, PLLC

(57) ABSTRACT

There is provided the use of compounds of formula I

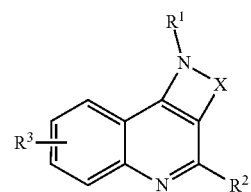

wherein $R^1$, $R^2$, $R^3$ and X have meanings given in the description, for the preparation of a medicament for killing clinically latent microorganisms. There is also provided the use of compounds of formula I for treating microbial infections, as well as certain compounds of formula I per se.

9 Claims, 4 Drawing Sheets

(56) References Cited

U.S. PATENT DOCUMENTS

| | | | |
|---|---|---|---|
| 2,691,024 | A | 10/1954 | Horlein et al. |
| 2,714,593 | A | 8/1955 | Horlein et al. |
| 4,771,052 | A | 9/1988 | Schonafinger et al. |
| 6,180,640 | B1 | 1/2001 | Cuny et al. |
| 6,995,163 | B2 | 2/2006 | Hibi et al. |
| 7,074,801 | B1 | 7/2006 | Yoshida et al. |
| 2004/0147580 | A1 | 7/2004 | Burgess et al. |
| 2004/0248890 | A1 | 12/2004 | Gonzalez, III et al. |
| 2009/0137622 | A1 | 5/2009 | Beck et al. |

FOREIGN PATENT DOCUMENTS

| | | |
|---|---|---|
| EP | 0481429 A2 | 4/1992 |
| EP | 0587473 A1 | 3/1994 |
| EP | 1 238 979 A1 | 9/2002 |
| GB | 725745 A | 3/1955 |
| JP | 6-92963 A | 4/1994 |
| WO | 9744342 A1 | 11/1997 |
| WO | 9805660 A1 | 2/1998 |
| WO | 9909029 A1 | 2/1999 |
| WO | 0001696 A1 | 1/2000 |
| WO | 0028074 A1 | 5/2000 |
| WO | 0142247 A1 | 6/2001 |
| WO | 2004002960 A1 | 1/2004 |
| WO | 2005076861 A2 | 8/2005 |
| WO | 2005/105802 A1 | 11/2005 |
| WO | 2006034235 A2 | 3/2006 |
| WO | 2006070284 A1 | 7/2006 |

OTHER PUBLICATIONS

Braga et al. "Making crystals from crystals: a green route to crystal engineering and polymorphism" Chem. Commun. 2005, 3635-3645.

Brown et al., "Reversible Inhibitors of the Gastric (H+/K+)-ATPase. 1. 1-Aryl-4-methylpyrrolo[3,2-c]quinolines as Conformationally Restrained Analogues of 4-(Arylamino)quinolines," J. Med. Chem., vol. 33, 1990, pp. 527-533, XP-000919165.

Chambers et al., "Reactions Involving Fluoride Ion. Part 42. Heterocyclic Compounds from 3,4-perfluoro-dimehtylhexa-2,4-diene", J. Chem. Soc., Perkin Trans.1, 1997, 1457-1463.

Chem. Abs., 2005, RN865658-30-6.

Chem. Abs., 2006, RN881294-38-8.

Chem. Abs., 2007, RN861210-25-5.

Chem. Abs., 2007, RN865658-34-0.

Cheon et al., "Anti-Ulcer Activity of Newly Synthesized Acylquoline Derivatives," 1999 pp. 137-142, vol. 22, No. 2, Arch. Pharm. Res.

Coates et al., "New Strategies for Antibacterial Drug Design, Targeting Non-Multiplying Latent Bacteria," 2006 pp. 133-151, vol. 7, Issue 3, Drugs R D.

Coates et al., "The Future Challenges Facing the Development of New Antimicrobial Drugs", Nature Reviews, 2002, 1, 895-910.

Coates, Anthony R.M., Ed."Dormancy and Low Growth States in Microbial Diseases", 2003 pp. 131-159, 181-207, Cambridge University Press, UK, Ed. A.R.M. Coates.

Dhillon et al., "Metronidazole Has No Antibacterial Effect in Cornell Model Murine Tuberculosis," 1998 pp. 736-742, vol. 2, No. 9, Int. J. Tuberc. Lung Dis.

European Office Action issued in corresponding application No. 06 808 472.2-2101 dated Feb. 3, 2012.

Fan et al., "Structures of 1-phenyl-2, 3, 4-tris(trifluoromethyl)pyrrolo[3,2-c]quinoline(1) and 2-fluoro-3-pentafluoroethyl-1-phenyl-2,3,4-tris(trifluoromethyl)-2-3-dihydropyrrolo[3,2-c]quinoline(2)", Acta Cryst., 1987, C43(11), 2206-2209.

Heidempergher et al., "Pyrrolo[3,2-c]quinoline derivatives: a new class of kynurenine-3-hydroxylase inhibitors," Il Farmaco, vol. 54, No. 3, 1999, pp. 152-160.

Helissey et al., "Synthesis, Antitumor Evaluation, and SAR of New 1H-Pyrrolo[3,2-c] Quinoline-6,9-Diones", Anti-Cancer Drug Design, 1994, 9, 51-67.

Herbert et al., "Bactericidal Action of Ofloxacin, Sulbactam-Ampicillin, Rifampin, and Isoniazid on Logarithmic- and Stationary-Phase Cultures of *Mycobacterium tuberculosis*," 1996 pp. 2296-2299, vol. 40, No. 10, Antimicrobial Agents and Chemotherapy.

Hu et al., "Detection of mRNA Transcripts and Active Transcription in Persistent *Mycobacterium tuberculosis* Induced by Exposure to Rifampin or Pyrazinamide," 2000 pp. 6358-6365, vol. 182, No. 22, Journal of Bacteriology.

Hu et al., "Increased Levels of sigJmRNA in Late Stationery Phase Cultures of *Mycobacterium tuberculosis* Detected by DNA Array Hybridisation", FEMS Microbiol. Lett., 2001, 202, 59-65.

Hu et al., "Sterilising Action of Pyrazinamide in Models of Dormant and Rifampicin-Tolerant *Mycobacterium tuberculosis*," 2006 pp. 317-322, vol. 10, No. 3, Int J Tuberc Lung Dis.

Hu et al., "Sterilizing Activities of Fluoroquinolones against Rifampin-Tolerant Populations of *Mycobacterium tuberculosis*" 2003 pp. 653-657, Vo. 47, No. 2, Antimicrobial Agents and Chemotherapy.

Hu et al., "Transposon Mutagenesis Identifies Genes Which Control Antimicrobial in Stationary Phase *Escherichia coli*", Drug Tolerance FEMS Microbiol. Lett., 2005, 243, 117-124.

Ife et al., "Reversible Inhibitors of the Gastric (H+/K+)-ATPase. 5. Substituted 2,4-Diaminoquinazolines and Thienopyrimidines," J. Med. Chem., 1995 pp. 2763-2773, vol. 38, No. 14.

International Preliminary Report on Patentability and Written Opinion dated May 14, 2008 issued in corresponding International Application No. PCT/GB2006/004178.

International Search Report, dated Apr. 18, 2008, in related International Application No. PCT/GB2007/004268.

Ji et al., "Characterization of human liver cytochrome P450 enzymes involved in the metabolism of a new H+/K+-ATPase inhibitor KR-60436," Toxicology Letters, 2005, pp. 103-114, vol. 155, No. 1.

Kim et al., "A Facile Method for Direct Conversion of Dihydrofuroquinolones to Dihydropyrroloquinolones," 1998 pp. 221-226, vol. 48, No. 2, Heterocycles.

Larsen et al., "Product Class 3: Quinolines," 2005 pp. 389-549, No. 15, Science of Synthesis.

Leach et al., "Reversible Inhibitors of the Gastric (H+/K+)-ATPase. 2. 1-Arylpyrrolo[3,2-c]quinolines: Effect of the 4-Substituent," J. Med. Chem., 1992, pp. 1845-1852, vol. 35, No. 10.

Li, Guangyun, et al., "Synthesis and Antimalarial Actvities of Derivatives of 2, 4-Dipiperidino- or 2,4-Dipyrrolidino-6(Substituted Amino)-Quinazolines" 1982, pp. 827-834, vol. 17, No. 11.

Meth-Cohn et al., "A Novel One-Step Synthesis of Quinolinium Salts and 4-Quinolones from Formanilides", Tetrahedron Lett., 1993, 34(22), 3629-32.

Meth-Cohn et al., "The Reverse Vilsmeier Approach to the Synthesis of Quinolines, Quinolinium Salts and Quinolones," Tetrahedron, 1995, 51(47), 12869-82.

Mitchison et al., "Predictive In Vitro Models of the Sterilizing Activity of Anti-Tuberculosis Drugs", Current Pharmaceutical Design, 2004, 10, 3285-3295.

Mohamed et al., "Synthesis and Anti-inflammatory Evaluation of Some New Quinazoline Derivatives", Int. Journal of Pharmacology, 2005, 1(3), 261-266.

Morissette et al. "High-throughput crystallization: polymorphs, salts, co-crystals and solvates of pharmaceutical solids" Advanced Drug Delivery Reviews, 2004, 56, 275-300.

Nagaoka, "Studies on the Synthesis of Quinoline Compounds. X. Condensation Reaction of 4-Chloroquinaldine Compounds and Aminophenols", J. Pharm. Soc. Japan., 1961, 81, 363-369.

Nagaoka, Studies on the Synthesis of Quinoline Compounds. XI Bromination Reaction of 4-Chloroquinaldine Compounds (1), J. Pharm. Soc. Japan., 1961, 81, 479-483.

Nagaoka, "Studies on the Synthesis of Quinoline Compounds. XI. Bromination Reaction of 4-Chloroquinaldine Compounds (2)", J. Pharm Soc. Japan., 1961, 81, 484-489.

Ozawa et al., "Studies of New Utilization of 2-Acetyl-gamma-butyrolactone. III. A New Synthesis of Quinaldine Derivatives. (3). A Synthesis of 4-Chloro-3-(2-chloroethyl)quinaldine Derivatives", J. Pharm. Soc. Japan, 1957 pp. 85-89, vol. 77.

(56) References Cited

OTHER PUBLICATIONS

Ozawa et al., "Studies on New Utilization of 2-Acetyl-y-butyrolactone. IV. Studies on the Antibacterial Activity of Quinaldine Compounds on Shigella flexneri 2a and *Salmonella typhi* H 901 W," J. Pharm. Soc. Japan, vol. 77, 1957, pp. 90-93 in Japanese, 14 pages with abstract and English translation, XP-002419062.

Parsons et al., "Tandem Radical Cyclisation Reactions for the Construction of Pseudocopsinine and Aspidosperma Alkaloid Models", Synlett (Spec. Issue), 1995, 507-509.

Parsons et al., "The Facile Construction of Indole Alkaloid Models: A Tandem Cascade Approach for the Synthesis of a Model for Pseudocopsinine," Tetrahedron, 1996 pp. 647-660, vol. 52, No. 2.

Reid et al., "Spectroscopic and Physicochemical Studies on the Interactions of Reversible H+/K+-ATPase Inhibitors with Phospholipid Bilayers", Biochimica et Biophysica Acta, Biomembranes, 1990, 1029(1), 24-32.

Seddon et al. "Pseudopolymorph: A Polemic" Crystal Growth and Design, 2004, 4, 1087.

Singh et al., "Quantitative Structure-Activity Relationship Studies of Inhibitors of (H+/K+)-ATPase", Drug Design and Delivery, 1991, 7(2), 131-138.

Tanaka et al., "Synthetic Studies on Pyrroloquinolines. I. Syntheses of 2,3-Dihydro-1H-pyrrolo[2,3-b]quinoline Derivatives," 1972 pp. 109-116, vol. 20, No. 1, Chem. Pharm. Bull.

Tapia et al., "A Convenient Synthesis of Benzo[g]Pyrrolo[3,2-c]Quinoline-6,11-Diones", Synthesis, 2005, 903-906.

Vippagunta et al. "Crystalline solids" Advanced Drug Delivery Reviews, 2001, 48, 3-26.

Yum et al., "Synthesis and Biological Profile of 1-Aryl-3-Substituted Pyrrolo[3,2-c] Quinolines", Bioorganic and Medicinal Chemistry Letters, 1999, 9(19), 2819-2822.

USE OF PYRROLOQUINOLINE COMPOUNDS TO KILL CLINICALLY LATENT MICROORGANISMS

This is a Divisional of application Ser. No. 12/092,947 filed Oct. 6, 2008 which is a national stage of PCT/GB2006/004178 filed Nov. 8, 2006, claiming priority based on United Kingdom Application No. 0522715.2 filed Nov. 8, 2005, the contents of all of which are incorporated herein by reference in their entirety.

This invention relates to the use of compounds based upon the pyrrolo[3,2-c]quinoline ring system to kill clinically latent microorganisms. The invention further relates to the use of such compounds to treat microbial infections, as well as, inter alia, certain of the compounds per se.

The listing or discussion of a prior-published document in this specification should not necessarily be taken as an acknowledgement that the document is part of the state of the art or is common general knowledge.

Before the introduction of antibiotics, patients suffering from acute bacterial infections (e.g. tuberculosis or pneumonia) had a low chance of survival. For example, mortality from tuberculosis was around 50%.

Although the introduction of antibacterial agents in the 1940s and 1950s rapidly changed this picture, bacteria have responded by progressively gaining resistance to commonly used antibiotics. Now, every country in the world has antibiotic-resistant bacteria. Indeed, more than 70% of bacteria that give rise to hospital acquired infections in the USA resist at least one of the main antimicrobial agents that are typically used to fight infection (see Nature Reviews, Drug Discovery 1, 895-910 (2002)).

One way of tackling the growing problem of resistant bacteria is the development of new classes of antimicrobial agents. However, until the introduction of linezolid in 2000, there had been no new class of antibiotic marketed for over 37 years. Moreover, even the development of new classes of antibiotic provides only a temporary solution, and indeed there are already reports of resistance of certain bacteria to linezolid (see Lancet 357, 1179 (2001) and Lancet 358, 207-208 (2001)).

In order to develop more long-term solutions to the problem of bacterial resistance, it is clear that alternative approaches are required. One such alternative approach is to minimise, as much as is possible, the opportunities that bacteria are given for developing resistance to important antibiotics.

Thus, strategies that can be adopted include limiting the use of antibiotics for the treatment of non-acute infections, as well as controlling which antibiotics are fed to animals in order to promote growth.

However, in order to tackle the problem more effectively, it is necessary to gain an understanding of the actual mechanisms by which bacteria generate resistance to antibiotic agents. To do this requires first a consideration of how current antibiotic agents work to kill bacteria.

Antimicrobial agents target essential components of bacterial metabolism. For example, the β-lactams (e.g. penicillins and cephalosporins) inhibit cell wall synthesis, whereas other agents inhibit a diverse range of targets, such as DNA gyrase (quinolones) and protein synthesis (e.g. macrolides, aminoglycosides, tetracyclines and oxazolidinones). The range of organisms against which the antimicrobial agents are effective varies, depending upon which organisms are heavily reliant upon the metabolic step(s) that is/are inhibited. Further, the effect upon bacteria can vary from a mere inhibition of growth (i.e. a bacteriostatic effect, as seen with agents such as the tetracyclines) to full killing (i.e. a bactericidal effect, as seen, for example, with penicillin).

Bacteria have been growing on Earth for more than 3 billion years and, in that time, have needed to respond to vast numbers of environmental stresses. It is therefore perhaps not surprising that bacteria have developed a seemingly inexhaustible variety of mechanisms by which they can respond to the metabolic stresses imposed upon them by antibiotic agents. Indeed, mechanisms by which the bacteria can generate resistance include strategies as diverse as inactivation of the drug, modification of the site of action, modification of the permeability of the cell wall, overproduction of the target enzyme and bypass of the inhibited steps.

Nevertheless, the rate of resistance emerges to a particular agent has been observed to vary widely, depending upon factors such as the agent's mechanism of action, whether the agent's mode of killing is time- or concentration-dependent, the potency against the population of bacteria and the magnitude and duration of the available serum concentration.

It has been proposed (see Science 264, 388-393 (1994)) that agents that target single enzymes (e.g. rifampicin) are the most prone to the development of resistance. Further, the longer that suboptimal levels of antimicrobial agent are in contact with the bacteria, the more likely the emergence of resistance.

Moreover, it is now known that many bacterial infections include sub-populations of bacteria that are phenotypically resistant to antimicrobials (see, for example: J. Antimicrob. Chemother. 4, 395-404 (1988); J. Med. Microbiol. 38, 197-202 (1993); J. Bacteriol. 182, 1794-1801 (2000); ibid. 182, 6358-6365 (2000); ibid. 183, 6746-6751 (2001); FEMS Microbiol. Lett. 202, 59-65 (2001); and Trends in Microbiology 13, 34-40 (2005)). There appear to be several types of such phenotypically resistant bacteria, including persisters, stationary-phase bacteria, as well as those in the depths of biofilms. However, each of these types is characterised by its low rate of growth (compared to log-phase bacteria under the same conditions). Nutritional starvation and high cell densities are also common characteristics of such bacteria.

Although resistant to antimicrobial agents in their slow-growing state, phenotypically resistant bacteria differ from those that are genotypically resistant in that they regain their susceptibility to antimicrobials when they return to a fast-growing state (e.g. when nutrients become more readily available to them).

The presence of phenotypically resistant bacteria in an infection leads to the need for prolonged courses of antimicrobial agents, comprising multiple doses. This is because the resistant, slowly multiplying bacteria provide a pool of "latent" organisms that can convert to a fast-growing state when the conditions allow (thereby effectively re-initiating the infection). Multiple doses over time deal with this issue by gradually killing off the "latent" bacteria that convert to "active" form.

However, dealing with "latent" bacteria by administering prolonged courses of antimicrobials poses its own problems. That is, prolonged exposure of bacteria to suboptimal concentrations of antimicrobial agent can lead to the emergence of genotypically resistant bacteria, which can then multiply rapidly in the presence of even high concentrations of the antimicrobial.

Long courses of antimicrobials are more likely to encourage the emergence of genotypic resistance than shorter courses on the grounds that non-multiplying bacterial will tend to survive and, interestingly, probably have an enhanced ability to mutate to resistance (see, for example: *Proc. Natl. Acad. Sci. USA* 92, 11736-11740 (1995); *J. Bacteriol.* 179, 6688-6691 (1997); and *Antimicrob. Agents Chemother.* 44, 1771-1777 (2000)). For example, non-dividing *E. coli* continually mutates to ciprofloxacin resistance during a seven-day exposure to the agent. [129] Thus, "latent" bacteria might be one of the sources of genotypically resistant bacteria.

In the light of the above, a new approach to combating the problem of bacterial resistance might be to select and develop antimicrobial agents on the basis of their ability to kill "latent" microorganisms. The production of such agents would allow, amongst other things, for the shortening of chemotherapy regimes in the treatment of microbial infections, thus reducing the frequency with which genotypical resistance arises in microorganisms.

Certain pyrrolo[2,3-c]quinolines, as well as their 2,3-dihydro derivatives, are disclosed in: *Science of Synthesis* 15, 389-549 (2005); *Heterocycles* 48(2), 221-226 (1998); *Tetrahedron* 52(2), 647-60 (1996); ibid. 51(47), 12869-82 (1995); *Synlett* (Spec. Issue), 507-509 (1995); *Tetrahedron Lett.* 34(22), 3629-32 (1993); JP 48030280; JP 48030078; JP 48030077; *Chem. & Pharm. Bull.* 20(1), 109-16 (1972); *Yakugaku Zasshi* 77, 85-9 (1957); ibid. 81, 363-9 (1961); ibid. 81, 479-83 and 484-9 (1961); *Acta Crystallographica* C43(11), 2206-9 (1987); *Acta Chimica Sinica* 41(7), 668-71 (1984); ibid. 42(5), 470-8 (1984); *J. Chem. Soc., Perkin Trans.* 1 1457-63 (1997); and *Anti-Cancer Drug Design* 9, 51-67 (1994).

Medical utilities of such compounds, for examples as inhibitors of the gastric ($H^+/K^+$)-ATPase, as agents for the treatment of diseases related to corticotropin-releasing factor (CRF) and/or corticotropin-releasing factor receptor, as agents for the prevention and/or treatment of neurodegenerative diseases, as inhibitors of the effects of free radicals, as immunoregulators, as antiinflammatory agents, as analgesics, as antipyretic agents, as hypotensive agents, as inhibitors of enzymes of the kynurenine pathway, as cytotoxic agents, or as inhibitors of HIV particle formation are mentioned in WO 97/44342; WO 98/05660; WO 99/09029; WO 00/01696; WO 01/42247; WO 2005/076861; EP 0 307 078; EP 0 587 473; JP 06092963; U.S. Pat. No. 4,771,052; U.S. Pat. No. 6,995,163; *J. Med. Chem.* 33(2), 527-33 (1990); *Drug Design and Delivery* 7, 131-8 (1991); *J. Med. Chem.* 35, 1845-52 (1992); *Farmaco* 54(3), 152-160 (1999); *Bioorg. Med. Chem. Lett.* 9, 2819-22 (1999); *Biochem. Biophys. Acta* 1029, 24-32 (1990); and *Eur. J. Med. Chem.* 32, 815-22 (1997).

Activity against malaria parasites, *Trypanosoma cruzi* and amoeba for certain 2,3-dihydropyrrolo[3,2-c]quinoline compounds is mentioned in GB 725 745, U.S. Pat. No. 2,691,023, U.S. Pat. No. 2,691,024 and *Synthesis* 903-906 (2005).

Further, activity against certain growing bacteria for a small number of 2,3-dihydropyrrolo[3,2-c]quinoline compounds is mentioned in *Yakugaku Zasshi* 77, 90-3 (1957).

We have now found, surprisingly, that pyrrolo[2,3-c]quinolines, or their 2,3-dihydro derivatives, may be used to kill clinically latent microorganisms.

According to a first aspect of the invention, there is provided the use of a compound of formula I, or a pharmaceutically-acceptable derivative thereof, for the preparation of a medicament for killing clinically latent microorganisms, wherein the compound of formula I is represented by the structure

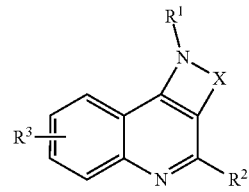

I wherein
$R^1$ represents
(a) H;
(b) $C_{1-12}$ alkyl, $C_{3-12}$ cycloalkyl, $C_{3-12}$ cycloalkenyl (which latter three groups are optionally substituted by one or more substituents selected from halo, nitro, CN, $C_{1-6}$ alkyl, $C_{1-6}$ alkenyl, $C_{1-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), $OR^{4a}$, $S(O)_n R^{4b}$, $S(O)_2 N(R^{4c})(R^{4d})$, $N(R^{4e})S(O)_2 R^{4f}$, $N(R^{4g})(R^{4h})$, $B^1$—C(O)—$B^2$—$R^{4i}$, aryl and $Het^1$, and which $C_{3-12}$ cycloalkyl or $C_{4-12}$ cycloalkenyl groups may additionally be substituted by =O),
(c) aryl or
(d) $Het^2$;
$R^2$ represents
(a) H;
(b) $C_{1-12}$ alkyl, $C_{1-12}$ alkenyl, $C_{1-12}$ alkynyl, $C_{3-12}$ cycloalkyl or $C_{4-12}$ cycloalkenyl, which latter five groups are optionally substituted by one or more substituents selected from halo, nitro, CN, $C_{1-6}$ alkyl, $C_{1-6}$ alkenyl, $C_{1-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), $OR^{5a}$, $S(O)_n R^{5b}$, $S(O)_2 N(R^{5c})(R^{5d})$, $N(R^{5e})S(O)_2 R^{5f}$, $N(R^{5g})(R^{5h})$, $B^3$—C(O)—$B^4$—$R^{5i}$, aryl and $Het^3$, and which $C_{3-12}$ cycloalkyl or $C_{4-12}$ cycloalkenyl groups may additionally be substituted by =O,
(c) aryl or
(d) $Het^4$;
$R^3$ represents H or one to four substituents on the fused benzene ring selected from
(a) halo,
(b) CN,
(c) $C_{1-12}$ alkyl, $C_{1-12}$ alkenyl, $C_{1-12}$ alkynyl, $C_{3-12}$ cycloalkyl or $C_{4-12}$ cycloalkenyl, which latter five groups are optionally substituted by one or more substituents selected from halo, nitro, CN, $C_{1-6}$ alkyl, $C_{1-6}$ alkenyl, $C_{1-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), $OR^{6a}$, $S(O)_q R^{6b}$, $S(O)_2 N(R^{6c})(R^{6d})$, $N(R^{6e})S(O)_2 R^{6f}$, $N(R^{6g})(R^{6h})$, $B^5$—C(O)—$B^6$—$R^{6i}$, aryl and $Het^5$, and which $C_{3-12}$ cycloalkyl or $C_{4-12}$ cycloalkenyl groups may additionally be substituted by =O,
(d) $OR^{7a}$,
(e) $S(O)_r R^{7b}$,
(f) $S(O)_2 N(R^{7c})(R^{7d})$,
(g) $N(R^{7e})S(O)_2 R^{7f}$,
(h) $N(R^{7g})(R^{7h})$,
(i) $B^7$—C(O)—$B^8$—$R^{7i}$,
(j) aryl or
(k) $Het^6$;

$R^{4a}$ to $R^{4i}$, $R^{5a}$ to $R^{5i}$, $R^{6a}$ to $R^{6i}$ and $R^{7a}$ to $R^{7i}$ independently represent, at each occurrence,
(a) H,
(b) $C_{1-10}$ alkyl, $C_{2-10}$ alkenyl, $C_{2-10}$ alkynyl (which latter three groups are optionally substituted by one or more substituents selected from halo, OH, $C_{1-6}$ alkoxy, aryl and $Het^7$),
(c) $C_{3-10}$ cycloalkyl, $C_{4-10}$ cycloalkenyl (which latter two groups are optionally substituted by one or more substituents selected from halo, OH, =O, $C_{1-6}$ alkyl, $C_{1-6}$ alkoxy, aryl and $Het^8$),
(d) aryl or
(e) $Het^9$,
provided that $R^{4b}$, $R^{5b}$, $R^{6b}$ or $R^{7b}$ does not represent H when n, p, q or r, respectively is 1 or 2;
X represents
—$C(R^{8a})(R^{8b})$—$C(R^{8c})(R^{8d})$— or
(b) —$C(R^{8e})$=$C(R^{8f})$—;
$R^{8a}$ to $R^{8f}$ independently represent H, halo or $C_{1-4}$ alkyl;
each aryl independently represents a $C_{6-10}$ carbocyclic aromatic group, which group may comprise either one or two rings and may be substituted by one or more substituents selected from
(a) halo,
(b) CN,
(c) $C_{1-12}$ alkyl, $C_{1-12}$ alkenyl, $C_{1-12}$ alkynyl, $C_{3-12}$ cycloalkyl or $C_{4-12}$ cycloalkenyl, which latter five groups are optionally substituted by one or more substituents selected from halo, nitro, CN, $C_{1-6}$ alkyl, $C_{1-6}$ alkenyl, $C_{1-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), $OR^{9a}$, $S(O)_tR^{9b}$, $S(O)_2N(R^{9c})(R^{9d})$, $N(R^{9e})S(O)_2R^{9f}$, $N(R^{9g})(R^{9h})$, $B^9$—C(O)—$B^{10}$—$R^{9i}$, phenyl, naphthyl (which latter two groups are optionally substituted by one or more substituents selected from OH, halo, $C_{1-4}$ alkyl and $C_{1-4}$ alkoxy) and $Het^{10}$, and which $C_{3-12}$ cycloalkyl or $C_{4-12}$ cycloalkenyl groups may additionally be substituted by =O,
(d) $OR^{10a}$,
(e) $S(O)_uR^{10b}$,
(f) $S(O)_2N(R^{10c})(R^{10d})$,
(g) $N(R^{10e})S(O)_2R^{10f}$,
(h) $N(R^{10g})(R^{10h})$,
(i) $B^{11}$—C(O)—$B^{12}R^{10i}$,
(j) phenyl (which latter group is optionally substituted by one or more substituents selected from OH, halo, $C_{1-4}$ alkyl and $C_{1-4}$ alkoxy) or
(k) $Het^{11}$;
$R^{9a}$ to $R^{9i}$ and $R^{10a}$ to $R^{10i}$ independently represent, at each occurrence,
(a) H,
(b) $C_{1-12}$ alkyl, $C_{2-12}$ alkenyl, $C_{2-12}$ alkynyl, $C_{3-12}$ cycloalkyl, $C_{4-12}$ cycloalkenyl (which latter five groups are optionally substituted by one or more substituents selected from halo, OH, $C_{1-6}$ alkyl, $C_{3-12}$ cycloalkyl, $C_{4-12}$ cycloalkenyl (which latter two groups are optionally substituted by one or more substituents selected from OH, =O, halo, $C_{1-4}$ alkyl and $C_{1-4}$ alkoxy), $C_{1-6}$ alkoxy, $NH_2$, $N(H)$—$C_{1-6}$ alkyl, $N(C_{1-6}$ alkyl$)_2$, phenyl (which latter group is optionally substituted by one or more substituents selected from OH, halo, $C_{1-4}$ alkyl and $C_{1-4}$ alkoxy) and $Het^{12}$, and which $C_{3-12}$ cycloalkyl or $C_{4-12}$ cycloalkenyl groups may additionally be substituted by =O,
(c) phenyl (which latter group is optionally substituted by one or more substituents selected from OH, CN, halo, $C_{1-6}$ alkyl and $C_{1-6}$ alkoxy) or
(e) $Het^{13}$,
provided that $R^{9b}$ or $R^{10b}$ does not represent H when t or u, respectively is 1 or 2;

$Het^1$ to $Het^{13}$ independently represent 4- to 14-membered heterocyclic groups containing one or more heteroatoms selected from oxygen, nitrogen and/or sulfur, which heterocyclic groups may comprise one, two or three rings and may be substituted by one or more substituents selected from
(a) halo,
(b) CN,
(c) $C_{1-12}$ alkyl, $C_{1-12}$ alkenyl, $C_{1-12}$ alkynyl, $C_{3-12}$ cycloalkyl or $C_{4-12}$ cycloalkenyl, which latter five groups are optionally substituted by one or more substituents selected from halo, nitro, CN, $C_{1-6}$ alkyl, $C_{1-6}$ alkenyl, $C_{1-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), $OR^{11a}$, $S(O)_vR^{11b}$, $S(O)_2N(R^{11c})(R^{11d})$, $N(R^{11e})S(O)_2R^{11f}$, $N(R^{11g})(R^{11h})$, $B^{13}$—C(O)—$B^{14}$—$R^{11i}$, phenyl, naphthyl (which latter two groups are optionally substituted by one or more substituents selected from OH, halo, $C_{1-4}$ alkyl and $C_{1-4}$ alkoxy) and $Het^a$, and which $C_{3-12}$ cycloalkyl or $C_{4-12}$ cycloalkenyl groups may additionally be substituted by =O,
(d) $OR^{12a}$,
(e) =O,
(f) $S(O)_wR^{12b}$,
(g) $S(O)_2N(R^{12c})(R^{12d})$,
(h) $N(R^{12e})S(O)_2R^{12f}$,
(i) $N(R^{12g})(R^{12h})$,
(j) $B^{15}$—C(O)—$B^{16}$—$R^{12i}$,
(k) phenyl (which latter group is optionally substituted by one or more substituents selected from OH, halo, $C_{1-4}$ alkyl and $C_{1-4}$ alkoxy) or
(l) $Het^b$;
$R^{11a}$ to $R^{11i}$ and $R^{12a}$ to $R^{12i}$ independently represent, at each occurrence,
(a) H,
(b) $C_{1-12}$ alkyl, $C_{2-12}$ alkenyl, $C_{2-12}$ alkynyl, $C_{3-12}$ cycloalkyl, $C_{4-12}$ cycloalkenyl (which latter five groups are optionally substituted by one or more substituents selected from halo, OH, $C_{1-6}$ alkyl, $C_{3-12}$ cycloalkyl, $C_{4-12}$ cycloalkenyl (which latter two groups are optionally substituted by one or more substituents selected from OH, =O, halo, $C_{1-4}$ alkyl and $C_{1-4}$ alkoxy), $C_{1-6}$ alkoxy, phenyl (which latter group is optionally substituted by one or more substituents selected from OH, halo, $C_{1-4}$ alkyl and $C_{1-4}$ alkoxy) and $Het^c$, and which $C_{3-12}$ cycloalkyl or $C_{4-12}$ cycloalkenyl groups may additionally be substituted by =O,
(c) phenyl (which latter group is optionally substituted by one or more substituents selected from OH, halo, $C_{1-4}$ alkyl and $C_{1-4}$ alkoxy) or
(e) $Het^d$,
provided that $R^{11b}$ or $R^{12b}$) does not represent H when v or w, respectively is 1 or 2;
$B^1$ to $B^{16}$ independently represent a direct bond, O, S, NH or $N(R^{13})$;
n, p, q, r, s, t, u, v and w independently represent 0, 1 or 2;
$R^{13}$ represents
(a) $C_{1-6}$ alkyl,
(b) phenyl (which latter group is optionally substituted by one or more substituents selected from OH, halo, $C_{1-4}$ alkyl and $C_{1-4}$ alkoxy),
(c) $C_{3-7}$ cycloalkyl (which latter group is are optionally substituted by one or more substituents selected from OH, =O, halo, $C_{1-4}$ alkyl and $C_{1-4}$ alkoxy) or
(e) $Het^c$;

Het$^a$ to Het$^e$ independently represent 5- or 6-membered heterocyclic groups containing one to four heteroatoms selected from oxygen, nitrogen and/or sulfur, which heterocyclic groups may be substituted by one or more substituents selected from halo, =O and $C_{1-6}$ alkyl; and unless otherwise specified (i) alkyl, alkenyl, alkynyl, cycloalkyl, and cycloalkenyl groups, as well as the alkyl part of alkoxy groups, may be substituted by one or more halo atoms, and (ii) cycloalkyl and cycloalkenyl groups may comprise one or two rings and may additionally be ring-fused to one or two benzene rings.

When used herein, the term "pharmaceutically-acceptable derivative" includes references to:

(a) pharmaceutically-acceptable salts with either acids or bases (e.g. acid addition salts); and/or (b) solvates (e.g. hydrates)

Acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalenesulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

The term "pharmaceutically-acceptable derivative" also includes references to:

(a) $C_{1-4}$ alkyl quaternary ammonium salts; or (b) N-oxides, at either of the two tertiary N-atoms of the (2,3-dihydro-) pyrroloquinoline ring system or at a tertiary N-atom that may be present in any of substituents $R^1$, $R^2$ and $R^3$.

For the avoidance of doubt, the definitions of the terms aryl, alkyl, alkenyl, alkynyl, cycloalkyl, cycloalkenyl and alkoxy groups provided above apply, unless otherwise stated, at each usage of such terms herein. Further, the one or two benzene rings that may be fused to cycloalkyl groups may bear one or more of the substituents defined in respect of the relevant cycloalkyl group.

The term "halo", when used herein, includes fluoro, chloro, bromo and iodo.

Heterocyclic (Het$^1$ to Het$^{13}$ and Het$^a$ to Het$^e$) groups may be fully saturated, partly unsaturated, wholly aromatic or partly aromatic in character. Values of heterocyclic (Het$^1$ to Het$^{13}$ and Het$^a$ to Het$^e$) groups that may be mentioned include 1-azabicyclo[2.2.2]octanyl, benzimidazolyl, benzo[c]isoxazolidinyl, benzisoxazolyl, benzodioxanyl, benzodioxepanyl, benzodioxolyl, benzofuranyl, benzofurazanyl, benzomorpholinyl, 2,1,3-benzoxadiazolyl, benzoxazolidinyl, benzoxazolyl, benzopyrazolyl, benzo[e]pyrimidine, 2,1,3-benzothiadiazolyl, benzothiazolyl, benzothienyl, benzotriazolyl, chromanyl, chromenyl, cinnolinyl, 2,3-dihydrobenzimidazolyl, 2,3-dihydrobenzo[b]furanyl, 1,3-dihydrobenzo-[c]furanyl, 1,3-dihydro-2,1-benzisoxazolyl 2,3-dihydropyrrolo[2,3-b]pyridinyl, dioxanyl, furanyl, hexahydropyrimidinyl, hydantoinyl, imidazolyl, imidazo[1,2-a]pyridinyl, imidazo[2,3-b]thiazolyl, indolyl, isoquinolinyl, isoxazolidinyl, isoxazolyl, maleimido, morpholinyl, naphtho[1,2-b]furanyl, oxadiazolyl, 1,2- or 1,3-oxazinanyl, oxazolyl, phthalazinyl, piperazinyl, piperidinyl, purinyl, pyranyl, pyrazinyl, pyrazolyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, sulfolanyl, 3-sulfolenyl, 4,5,6,7-tetrahydrobenzimidazolyl, 4,5,6,7-tetrahydrobenzopyrazolyl, 5,6,7,8-tetrahydro-benzo[e]pyrimidine, tetrahydrofuranyl, tetrahydropyranyl, 3,4,5,6-tetrahydro-pyridinyl, 1,2,3,4-tetrahydropyrimidinyl, 3,4,5,6-tetrahydropyrimidinyl, thiadiazolyl, thiazolidinyl, thiazolyl, thienyl, thieno[5,1-c]pyridinyl, thiochromanyl, triazolyl, 1,3,4-triazolo[2,3-b]pyrimidinyl, xanthenyl and the like. Values of Het$^1$ that may be mentioned include benzodioxanyl (e.g. benzodioxan-2-yl), benzodioxolyl (e.g. benzodioxol-5-yl), pyrazinyl (e.g. pyrazin-2-yl), pyridinyl (e.g. pyridin-2-yl or pyridin-3-yl), pyrrolidinonyl (e.g. pyrrolidinon-1-yl) and tetrahydrofuranyl (e.g. tetrahydrofuran-2-yl).

Values of Het$^2$ that may be mentioned include benzimidazolyl (e.g. benzimidazol-2-yl), piperidinyl (e.g. piperidin-4-yl), pyridinyl (e.g. pyridin-3-yl) and pyrrolidinyl (e.g. pyrrolidin-3-yl).

Values of Het$^6$ that may be mentioned include morpholinyl (e.g. morpholin-4-yl) and piperidinyl (e.g. piperidin-4-yl).

Values of Het$^9$ that may be mentioned include piperidinyl (e.g. piperidin-1-yl).

Values of Het$^{11}$ that may be mentioned include piperazinyl (e.g. piperazin-1-yl), piperidinyl (e.g. piperidin-1-yl) and pyridinyl (e.g. pyridin-3-yl).

Values of Het$^{13}$ that may be mentioned include pyridinyl (e.g. pyridin-3-yl).

Compounds of formula I that may be mentioned include:

(a) those in which $R^1$ and/or $R^2$ represents H; and (b) those in which $R^1$ represents other than H and/or $R^2$ represents other than H.

When used herein, the term "microorganisms" means:

(a) fungi (as defined below); and, particularly (b) bacteria (as defined below).

References herein to the terms "microbial", "antimicrobial" and "antimicrobially" shall be interpreted in accordance with the definition of "microorganisms". For example, the term "microbial" means fungal or, particularly, bacterial.

When used herein, the term "clinically latent" includes references to microorganisms that are viable but non-culturable (e.g. bacteria that cannot be detected by standard culture techniques but that are detectable and quantifiable by techniques such as broth dilution counting, microscopy, or molecular techniques such as polymerase chain reaction).

The term "clinically latent" also includes references to microorganisms that are phenotypically tolerant, for example microorganisms that:

(a) are sensitive (e.g. in log phase) to the biostatic (e.g. bacteriostatic) effects of conventional antimicrobial agents (i.e. microorganisms for which the minimum inhibitory concentration (MIC) of a conventional antimicrobial is substantially unchanged); but (b) possess drastically decreased susceptibility to drug-induced killing (e.g. microorganisms for which, with any given conventional antimicrobial agent, the ratio of minimum microbicidal concentration (e.g. minimum bactericidal concentration, MBC) to MIC is 10 or more).

In relation to point (a) above, "substantially unchanged" refers to MIC values that are anywhere from 50 to 200%

(e.g. 90 to 110%) of the value determined under standard conditions for the microorganism and conventional antimicrobial agent concerned.

For the avoidance of doubt, the term "clinically latent" excludes references to microorganisms that are genotypically resistant to conventional antimicrobial agents (i.e. microorganisms that differ genetically from antimicrobial-sensitive members of the same genus and that display an increased MIC (e.g. in log phase) for one or more conventional antimicrobial agents compared to said antimicrobial-sensitive microorganisms).

The term "clinically latent" further includes references to microorganisms that:
(i) are metabolically active; but
(ii) have a growth rate that is below the threshold of infectious disease expression.

The term "threshold of infectious disease expression" will be understood by those skilled in the art to include references to the growth rate threshold below which the symptoms of infectious disease (in a patient infected with the relevant microorganism) are absent.

In relation to point (i) above, metabolic activity of latent microorganisms can be determined by several methods known to those skilled in the art, for example by measuring mRNA levels in the microorganisms or by determining their rate of uridine uptake. In this respect, the term "clinically latent" further includes references to microorganisms that, compared to the same number of microorganisms under logarithmic growth conditions (in vitro or in vivo), possess reduced but still significant levels of:
(I) mRNA (e.g. from 0.0001 to 50%, such as from 1 to 30, 5 to 25 or 10 to 20%, of the level of mRNA); and/or
(II) uridine (e.g. [$^3$H]uridine) uptake (e.g. from 0.0005 to 50%, such as from 1 to 40, 15 to 35 or 20 to 30% of the level of [$^3$H]uridine uptake).

When used herein, the term "conventional antimicrobial agent(s)" means:
(a) conventional antifungal agents; and, particularly
(b) conventional antibacterial agents,
wherein each of (a) and (b) is as defined below.

When used herein, the term "conventional antibacterial agent(s)" include references to bactericidal and bacteristatic agents that are known in the prior art (i.e. agents that have been selected and developed on the basis of their MICs—namely their ability to inhibit the growth of bacteria). In this respect, particular conventional antibiotic agents that may be mentioned include any one or more of the following.

(a) β-Lactams, including:
  (i) penicillins, such as
    (I) benzylpenicillin, procaine benzylpenicillin, phenoxymethylpenicillin, methicillin, propicillin, epicillin, cyclacillin, hetacillin, 6-aminopenicillanic acid, penicillic acid, penicillanic acid sulphone (sulbactam), penicillin G, penicillin V, phenethicillin, phenoxymethylpenicillinic acid, azlocillin, carbenicillin, cloxacillin, D-(−)-penicillamine, dicloxacillin, nafcillin and oxacillin,
    (II) penicillinase-resistant penicillins (e.g. flucloxacillin),
    (III) broad-spectrum penicillins (e.g. ampicillin, amoxicillin, metampicillin and bacampicillin),
    (IV) antipseudomonal penicillins (e.g. carboxypenicillins such as ticarcillin or ureidopenicillins such as piperacillin),
    (V) mecillinams (e.g. pivmecillinam), or
    (VI) combinations of any two or more of the agents mentioned at (I) to (V) above, or combinations of any of the agents mentioned at (I) to (V) above with a β-lactamase inhibitor such as tazobactam or, particularly, clavulanic acid (which acid is optionally in metal salt form, e.g. in salt form with an alkali metal such as sodium or, particularly, potassium);
  (ii) cephalosporins, such as cefaclor, cefadroxil, cefalexin (cephalexin), cefcapene, cefcapene pivoxil, cefdinir, cefditoren, cefditoren pivoxil, cefixime, cefotaxime, cefpirome, cefpodoxime, cefpodoxime proxetil, cefprozil, cefradine, ceftazidime, cefteram, cefteram pivoxil, ceftriaxone, cefuroxime, cefuroxime axetil, cephaloridine, cephacetrile, cephamandole, cephaloglycine, ceftobiprole, PPI-0903 (TAK-599), 7-aminocephalosporanic acid, 7-aminodes-acetoxycephalosporanic acid, cefamandole, cefazolin, cefmetazole, cefoperazone, cefsulodin, cephalosporin C zinc salt, cephalothin, cephapirin; and
  (iii) other β-lactams, such as monobactams (e.g. aztreonam), carbapenems (e.g. imipenem (optionally in combination with a renal enzyme inhibitor such as cilastatin), meropenem, ertapenem, doripenem (S-4661) and RO4908463 (CS-023)), penems (e.g. faropenem) and 1-oxa-β-lactams (e.g. moxalactam).
(b) Tetracyclines, such as tetracycline, demeclocycline, doxycycline, lymecycline, minocycline, oxytetracycline, chlortetracycline, meclocycline and methacycline, as well as glycylcyclines (e.g. tigecycline).
(c) Aminoglycosides, such as amikacin, gentamicin, netilmicin, neomycin, streptomycin, tobramycin, amastatin, butirosin, butirosin A, daunorubicin, dibekacin, dihydrostreptomycin, G 418, hygromycin B, kanamycin B, kanamycin, kirromycin, paromomycin, ribostamycin, sisomicin, spectinomycin, streptozocin and thiostrepton.
(d)
  (i) Macrolides, such as azithromycin, clarithromycin, erythromycin, roxithromycin, spiramycin, amphotericins B (e.g. amphotericin B), bafilomycins (e.g. bafilomycin A1), brefeldins (e.g. brefeldin A), concanamycins (e.g. concanamycin A), filipin complex, josamycin, mepartricin, midecamycin, nonactin, nystatin, oleandomycin, oligomycins (e.g. oligomycin A, oligomycin B and oligomycin C), pimaricin, rifampicin, rifamycin, rosamicin, tylosin, virginiamycin and fosfomycin.
  (ii) Ketolides such as telithromycin and cethromycin (ABT-773).
  (iii) Lincosamines, such as lincomycin.
(e) Clindamycin and clindamycin 2-phosphate.
(f) Phenicols, such as chloramphenicol and thiamphenicol.
(g) Steroids, such as fusidic acid (optionally in metal salt form, e.g. in salt form with an alkali metal such as sodium).
(h) Glycopeptides such as vancomycin, teicoplanin, bleomycin, phleomycin, ristomycin, telavancin, dalbavancin and oritavancin.
(i) Oxazolidinones, such as linezolid and AZD2563.
(j) Streptogramins, such as quinupristin and dalfopristin, or a combination thereof.
(k)
  (i) Peptides, such as polymyxins (e.g. colistin and polymyxin B), lysostaphin, duramycin, actinomycins (e.g. actinomycin C and actinomycin D), actinonin, 7-aminoactinomycin D, antimycin A, antipain, bacitracin, cyclosporin A, echinomycin, gramicidins (e.g. gramicidin A and gramicidin C), myxothiazol, nisin, paracelsin, valinomycin and viomycin.
  (ii) Lipopeptides, such as daptomycin.
  (iii) Lipoglycopeptides, such as ramoplanin.

(l) Sulfonamides, such as sulfamethoxazole, sulfadiazine, sulfaquinoxaline, sulfathiazole (which latter two agents are optionally in metal salt form, e.g. in salt form with an alkali metal such as sodium), succinylsulfathiazole, sulfadimethoxine, sulfaguanidine, sulfamethazine, sulfamonomethoxine, sulfanilamide and sulfasalazine.

(m) Trimethoprim, optionally in combination with a sulfonamide, such as sulfamethoxazole (e.g. the combination co-trimoxazole).

(n) Antituberculous drugs, such as isoniazid, rifampicin, rifabutin, pyrazinamide, ethambutol, streptomycin, amikacin, capreomycin, kanamycin, quinolones (e.g. those at (q) below), para-aminosalicylic acid, cycloserine and ethionamide.

(o) Antileprotic drugs, such as dapsone, rifampicin and clofazimine.

(p)
  (i) Nitroimidazoles, such as metronidazole and timidazole.
  (ii) Nitrofurans, such as nitrofurantoin.

(q) Quinolones, such as nalidixic acid, norfloxacin, ciprofloxacin, ofloxacin, levofloxacin, moxifloxacin, gatifloxacin, gemifloxacin, garenoxacin, DX-619, WCK 771 (the arginine salt of S-(−)-nadifloxacin), 8-quinolinol, cinoxacin, enrofloxacin, flumequine, lomefloxacin, oxolinic acid and pipemidic acid.

(r) Amino acid derivatives, such as azaserine, bestatin, D-cycloserine, 1,10-phenanthroline, 6-diazo-5-oxo-L-norleucine and L-alanyl-L-1-aminoethyl-phosphonic acid.

(s) Aureolic acids, such as chromomycin A3, mithramycin A and mitomycin C.

(t) Benzochinoides, such as herbimycin A.

(u) Coumarin-glycosides, such as novobiocin.

(v) Diphenyl ether derivatives, such as irgasan.

(w) Epipolythiodixopiperazines, such as gliotoxin from *Gliocladium fimbriatum*.

(x) Fatty acid derivatives, such as cerulenin.

(y) Glucosamines, such as 1-deoxymannojirimycin, 1-deoxynojirimycin and N-methyl-1-deoxynojirimycin.

(z) Indole derivatives, such as staurosporine.

(aa) Diaminopyrimidines, such as iclaprim (AR-100).

(ab) Macrolactams, such as ascomycin.

(ac) Taxoids, such as paclitaxel.

(ad) Statins, such as mevastatin.

(ae) Polyphenolic acids, such as (+)-usnic acid.

(af) Polyethers, such as lasalocid A, lonomycin A, monensin, nigericin and salinomycin.

(ag) Picolinic acid derivatives, such as fusaric acid.

(ah) Peptidyl nucleosides, such as blasticidine S, nikkomycin, nourseothricin and puromycin.

(ai) Nucleosides, such as adenine 9-β-D-arabinofuranoside, 5-azacytidine, cordycepin, formycin A, tubercidin and tunicamycin.

(aj) Pleuromutilins, such as GSK-565154, GSK-275833 and tiamulin.

(ak) Peptide deformylase inhibitors, such as LBM415 (NVP PDF-713) and BB 83698.

(al) Antibacterial agents for the skin, such as fucidin, benzamycin, clindamycin, erythromycin, tetracycline, silver sulfadiazine, chlortetracycline, metronidazole, mupirocin, framycitin, gramicidin, neomycin sulfate, polymyxins (e.g. polymixin B) and gentamycin;

(al) Miscellaneous agents, such as methenamine (hexamine), doxorubicin, piericidin A, stigmatellin, actidione, anisomycin, apramycin, coumermycin A1, L(+)-lactic acid, cytochalasins (e.g. cytochalasin B and cytochalasin D), emetine and ionomycin.

Particular conventional antibiotics that may be mentioned include those listed at (a) to (q) above, such as:
  the -cillins listed at (a)(i) above (e.g. amoxicillin, ampicillin, phenoxymethylpenicillin or, particularly, co-amoxiclav (co-amoxicillin));
  the cephalosporins listed at (a)(ii) above (e.g. cefuroxime, cefaclor or cefalexin);
  the carbapenems listed at (a)(iii) above (e.g. ertapenem);
  the tetracyclines listed at (b) above (e.g. doxycycline or minocycline);
  the macrolides listed at (d)(i) above (e.g. clarithromycin, erythromycin, roxithromycin or, particularly, azithromycin);
  the ketolides listed at (d) (ii) above (e.g. telithromycin);
  the oxazolidinones listed at (i) above (e.g. linezolid);
  the lipopeptides listed at (k)(ii) above (e.g. daptomycin) trimethoprim and the combinations therewith (e.g. co-trimoxazol) listed at (m) above;
  the nitrofurans listed at (p) above (e.g. nitrofurantoin); and
  the quinolones listed at (q) above (e.g. norfloxacin, ciprofloxacin, ofloxacin, or, particularly, levofloxacin or moxifloxacin).

When used herein, the term "conventional antifungal agent(s)" include references to fungicidal and fungistatic agents that are known in the prior art (i.e. agents that have been selected and developed on the basis of their MICs—namely their ability to inhibit the growth of fungi). In this respect, particular conventional antifungal agents that may be mentioned include any one or more of the following.

(a) azole antifungals, such as imidazoles (e.g. clotrimazole, econazole, fenticonazole, ketoconazole, miconazole, sulconazole, and tioconazole) or triazoles (e.g. fluconazole, itraconazole and voriconazole);

(b) polyene antifungals, such as amphotericin and nystatin;

(c) miscellaneous antifungal agents such as griseofulvin, caspofungin or flucytosine, which latter two agents are optionally employed in combination;

(d) allylamine antifungals, such as terbinafine.

Compounds of formula I that may be mentioned include the following.

(1) A compound of formula I, as hereinbefore defined, provided that the compound is not of the formula

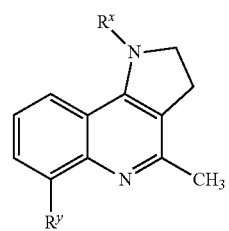

in which:
  (a) $R^y$ represents H and $R^x$ represents H, methyl, 2-hydroxyethyl, phenyl, 4-methylphenyl, 4-methoxyphenyl or 2-chlorophenyl;
  (b) $R^y$ represents methoxy and $R^x$ represents phenyl; or
  (c) $R^y$ represents hydroxy and $R^x$ represents methyl, 2-hydroxyethyl or phenyl.

(In other words, the compound is not:
4-methyl-2,3-dihydro-1H-pyrrolo[3,2-c]quinoline;
1,4-dimethyl-2,3-dihydro-1H-pyrrolo[3,2-c]quinoline;
1-[2-hydroxyethyl]-4-methyl-2,3-dihydro-1H-pyrrolo[3,2-c]quinoline;
4-methyl-1-phenyl-2,3-dihydro-1H-pyrrolo[3,2-c]quinoline;
4-methyl-1-(4-methylphenyl)-2,3-dihydro-1H-pyrrolo[3,2-c]quinoline;
4-methyl-1-(4-methoxyphenyl)-2,3-dihydro-1H-pyrrolo[3,2-c]quinoline;
4-methyl-1-(2-chlorophenyl)-2,3-dihydro-1H-pyrrolo[3,2-c]quinoline;
6-methoxy-4-methyl-1-phenyl-2,3-dihydro-1H-pyrrolo[3,2-c]quinoline;
6-hydroxy-1,4-dimethyl-2,3-dihydro-1H-pyrrolo[3,2-c]quinoline;
6-hydroxy-1-[2-hydroxyethyl]-4-methyl-2,3-dihydro-1H-pyrrolo[3,2-c]quinoline; or
6-hydroxy-4-methyl-1-phenyl-2,3-dihydro-1H-pyrrolo[3,2-c]quinoline.)

(2) A compound of formula I, as hereinbefore defined, provided that $R^3$ does not represent H or a single $OR^{7a}$ substituent at the 6-position of the pyrrolo[3,2-c]quinoline or 2,3-dihydro-1H-pyrrolo[3,2-c]quino line ring system, wherein $R^{7a}$ either:
(a) is as hereinbefore defined;
(b) represents H or $C_{1-10}$ alkyl; or
(c) represents H or methyl.

(3) A compound of formula I, as hereinbefore defined, in which X represents —C($R^{8a}$)($R^{8b}$)—C($R^{8c}$)($R^{8d}$)—, wherein $R^{8a}$ to $R^{8d}$ are as hereinbefore defined.

Particular embodiments of the compounds of formula I include those in which:

(1) $R^1$ represents
$C_{1-6}$ alkyl or $C_{3-7}$ cycloalkyl (which latter two groups are optionally substituted by one or more substituents selected from halo, $C_{1-4}$ alkyl, $C_{3-6}$ cycloalkyl (which latter group is optionally substituted by one or more substituents selected from halo, $C_{1-4}$ alkyl and $C_{1-4}$ alkoxy), $OR^{4a}$, $C(O)OR^{4i}$, aryl and $Het^1$) (such as $C_{1-6}$ alkyl or $C_{3-7}$ cycloalkyl (which latter two groups are optionally substituted by one or more substituents selected from halo, $C_{1-4}$ alkyl, $C_{3-6}$ cycloalkyl (which latter group is optionally substituted by one or more substituents selected from halo, $C_{1-4}$ alkyl and $C_{1-4}$ alkoxy), $OR^{4a}$, aryl and $Het^1$),
aryl or
$Het^2$;

(2) $R^2$ represents $C_{1-6}$ alkyl optionally substituted by one or more substituents selected from halo, $OR^{5a}$, $N(R^{5g})(R^{5h})$ and $C(O)OR^{5i}$;

(3) $R^3$ represents H or, particularly, one to four substituents on the fused benzene ring selected from
halo (e.g. chloro),
CN,
$C_{1-6}$ alkyl optionally substituted by one or more substituents selected from halo, CN, and $OR^{6a}$,
$OR^{7a}$,
$S(O)_rR^{7b}$,
$N(H)R^{7h}$,
$C(O)R^{7i}$,
$C(O)OR^{7i}$,
aryl and
$Het^6$
(e.g. $R^3$ represents one to four substituents on the fused benzene ring selected from $C_{1-6}$ alkyl (optionally substituted by one or more substituents selected from halo, CN, and $OR^{6a}$), $OR^{7a}$, $S(O)_rR^{7b}$, aryl and $Het^6$);

(4) $R^{4a}$ to $R^{4i}$, $R^{5a}$ to $R^{5i}$, $R^{6a}$ to $R^{6i}$ and $R^{7a}$ to $R^{7i}$ independently represent, at each occurrence,
$C_{1-10}$ alkyl (optionally substituted by one or more substituents selected from halo and aryl),
$C_{3-6}$ cycloalkyl (optionally substituted by one or more substituents selected from halo, $C_{1-4}$ alkyl and $C_{1-4}$ alkoxy),
aryl or
$Het^9$,
or $R^{4a}$ to $R^{4i}$, $R^{5a}$ to $R^{5i}$, $R^{6a}$ to $R^{6i}$ and $R^{7c}$ to $R^{7i}$ may also represent H,
provided that $R^{4b}$, $R^{5b}$, $R^{6b}$ or $R^{7b}$ does not represent H when n, p, q or r, respectively is 1 or 2;

(5) X represents —C(H)$R^{8a}$—C(H)$R^{8c}$—;

(6) $R^{8a}$ to $R^{8f}$ independently represent H or methyl;

(7) each aryl independently represents a $C_{6-10}$ carbocyclic aromatic group, which group may comprise either one or two rings and may be substituted by one or more substituents selected from
halo,
CN,
$C_{1-6}$ alkyl optionally substituted by one or more substituents selected from halo, $C_{3-6}$ cycloalkyl (which latter groups is optionally substituted by one or more substituents selected from halo, $C_{1-4}$ alkyl and $C_{1-4}$ alkoxy), $OR^{9a}$, $S(O)_tR^{9b}$, $S(O)_2N(H)R^{9c}$, $N(H)S(O)_2R^{9f}$, $N(R^{9g})(R^{9h})$, $B^9$—C(O)—$B^{10}$—$R^{9i}$, phenyl (which latter groups is optionally substituted by one or more substituents selected from OH, halo, methyl and methoxy) and $Het^{10}$,
$OR^{10a}$,
$S(O)_uR^{10b}$,
$N(R^{10g})(R^{10h})$,
$B^{11}$—C(O)—$B^{12}$—$R^{10i}$,
phenyl (which latter group is optionally substituted by one or more substituents selected from OH, halo, $C_{1-4}$ alkyl and $C_{1-4}$ alkoxy) or
$Het^{11}$;

(8) $R^{9a}$ to $R^{9i}$ and $R^{10a}$ to $R^{10i}$ independently represent, at each occurrence,
H,
$C_{1-6}$ alkyl, $C_{3-6}$ cycloalkyl (which latter two groups are optionally substituted by one or more substituents selected from halo, OH, $C_{1-4}$ alkyl, $C_{4-6}$ cycloalkyl (which latter group is optionally substituted by one or more substituents selected from halo, $C_{1-4}$ alkyl and $C_{1-4}$ alkoxy), $C_{1-4}$ alkoxy, $NH_2$, N(H)—$C_{1-4}$ alkyl, N($C_{1-4}$ alkyl)$_2$, phenyl (which latter group is optionally substituted by one or more substituents selected from OH, halo, methyl and methoxy) and $Het^{12}$),
phenyl (which latter group is optionally substituted by one or more substituents selected from OH, halo, $C_{1-4}$ alkyl and $C_{1-4}$alkoxy) or $Het^{13}$,
provided that $R^{9b}$ or $R^{10b}$ does not represent H when t or u, respectively is 1 or 2;

(9) $Het^1$ to $Het^{13}$ independently represent 5- to 10-membered heterocyclic groups containing from one to four heteroatoms selected from oxygen, nitrogen and/or sulfur, which heterocyclic groups may comprise one or two rings and may be substituted by one or more substituents selected from
halo,
$C_{1-6}$ alkyl, $C_{3-6}$ cycloalkyl, which latter two groups are optionally substituted by one or more substituents selected from halo, OH, $C_{1-4}$ alkyl, $C_{4-6}$ cycloalkyl (which latter group is optionally substituted by one or more substituents selected from halo, $C_{1-4}$ alkyl and $C_{1-4}$ alkoxy), $C_{1-4}$ alkoxy, phenyl (which latter group is optionally substituted by one or more substituents selected from OH, halo, methyl and methoxy) and Het$^a$,
OR$^{12a}$,
=O,
S(O)$_w$R$^{12b}$,
N(R$^{12g}$)(R$^{12h}$),
B$^{15}$—C(O)—B$^{16}$—R$^{12i}$,
phenyl (which latter group is optionally substituted by one or more substituents selected from OH, halo, methyl and methoxy) or
Het$^b$;

(10) R$^{11a}$ to R$^{11i}$ and R$^{12a}$ to R$^{12i}$ independently represent, at each occurrence,
H,
$C_{1-6}$ alkyl, $C_{3-6}$ cycloalkyl (which latter two groups are optionally substituted by one or more substituents selected from halo, OH, $C_{1-4}$ alkyl, $C_{4-6}$ cycloalkyl (which latter group is optionally substituted by one or more substituents selected from halo, $C_{1-4}$ alkyl and $C_{1-4}$ alkoxy), $C_{1-4}$ alkoxy, phenyl (which latter group is optionally substituted by one or more substituents selected from OH, halo, methyl and methoxy) and Het$^c$,
phenyl (which latter group is optionally substituted by one or more substituents selected from OH, halo, methyl and methoxy) or
Het$^d$,
provided that R$^{11b}$ or R$^{12b}$ does not represent H when v or w, respectively is 1 or 2;

(11) B$^1$ to B$^{16}$ independently represent a direct bond, O, S or NH;

(12) R$^{13}$ represents $C_{1-4}$ alkyl or phenyl (which latter group is optionally substituted by one or more substituents selected from OH, halo, methyl and methoxy);

(13) Het$^a$ to Het$^e$ independently represent 5- or 6-membered heterocyclic groups containing one or heteroatoms selected from oxygen, nitrogen and/or sulfur, which heterocyclic groups may be substituted by one or more substituents selected from halo, =O and methyl;

(14) unless otherwise specified, alkyl, alkenyl, alkynyl, cycloalkyl, and cycloalkenyl groups, as well as the alkyl part of alkoxy groups, are unsubstituted;

(15) unless otherwise specified, cycloalkyl groups comprise one or (if sufficient number of C-atoms is present) two rings and are optionally ring-fused to a benzene ring (so as to form a group such as, for example, 1,2,3,4-tetrahydronaphthyl or, particularly, indanyl).

More particular embodiments of the compounds of formula I include those in which:

(1) R$^1$ represents
$C_{1-5}$ alkyl (which latter group is optionally substituted by one or more substituents selected from fluoro, $C_{3-5}$ cycloalkyl (which latter group is optionally substituted by one or more substituents selected from fluoro, methyl and methoxy), $C_{1-4}$ alkoxy (e.g. methoxy), phenoxy, phenyl (which latter group is optionally substituted by one or more substituents selected from halo, $C_{1-4}$ alkyl and $C_{1-4}$ alkoxy) and Het$^1$),
$C_{3-6}$ cycloalkyl, (which latter group is optionally fused to a benzene ring (e.g. to form a group such as indanyl or 1,2,3,4-tetrahydronaphthyl) and is optionally substituted by one or more substituents selected from fluoro, methyl and methoxy),
phenyl (which latter group is optionally substituted by one or more substituents selected from halo, $C_{1-6}$ alkyl (which latter group is optionally substituted by one or more substituents selected from OR$^{9a}$, N(R$^{9g}$)(R$^{9h}$) and phenyl), OR$^{10a}$ and Het$^{11}$), or
Het$^2$;

(2) Het$^1$ represents 5- to 10-membered, aromatic or part-aromatic heterocyclic group containing from one to four heteroatoms selected from oxygen, nitrogen and/or sulfur, which heterocyclic group comprises either one or two rings and is optionally substituted by one or more substituents selected from halo, $C_{1-3}$ alkyl (e.g. methyl) and $C_{1-3}$ alkoxy (e.g. methoxy) (e.g. Het$^1$ represents a 9- or 10-membered, aromatic or part-aromatic heterocyclic group containing one or two heteroatoms selected from oxygen and nitrogen, such as a benzodioxanyl or benzodioxolyl group);

(3) Het$^2$ represents a 5- to 10-membered, heterocyclic group containing from one to four heteroatoms selected from oxygen, nitrogen and/or sulfur, which heterocyclic group comprises either one or two rings and is optionally substituted by one or more substituents selected from halo, $C_{1-3}$ alkyl (which latter group is optionally substituted by phenyl) and OR$^{12a}$ (e.g. Het$^2$ represents a 5- or 6-membered, aromatic or fully saturated heterocyclic group containing one or two heteroatoms selected from oxygen and nitrogen, such as a pyridyl or piperidinyl group, which group is optionally substituted by $C_{1-2}$ alkyl (which latter group is optionally substituted by phenyl), $C_{1-3}$ alkoxy (e.g. methoxy) or phenoxy);

(4) Het$^{11}$ represents a 5- to 6-membered, fully saturated, partly unsaturated or aromatic heterocyclic group containing one or two heteroatoms selected from oxygen, nitrogen and/or sulfur, which heterocyclic group is optionally substituted by one or more substituents selected from halo and $C_{1-3}$ alkyl (e.g. Het$^{11}$ represents a 6-membered, fully saturated heterocyclic group containing one or two heteroatoms selected from oxygen and nitrogen, such as a piperazinyl group, which group is optionally substituted by $C_{1-3}$ alkyl (e.g. methyl));

(5) R$^{9a}$ to R$^{9i}$ independently represent, at each occurrence, H or $C_{1-3}$ alkyl (e.g. methyl);

(6) R$^{10a}$ represents, independently at each occurrence,
H,
$C_{1-4}$ alkyl, $C_{5-6}$ cycloalkyl (which latter two groups are optionally substituted by one or more substituents selected from halo, methyl, methoxy, NH$_2$, N(H)CH$_3$, N(CH$_3$)$_2$ or phenyl),
phenyl (which latter group is optionally substituted by one or more substituents selected from halo, methyl and methoxy) or
Het$^{13}$;

(7) Het$^{13}$ represents a 5- to 10-membered, aromatic heterocyclic group containing from one to four heteroatoms selected from oxygen, nitrogen and/or sulfur, which heterocyclic group comprises either one or two rings and is optionally substituted by one or more substituents selected from halo, $C_{1-3}$ alkyl (e.g. methyl) and $C_{1-3}$ alkoxy (e.g. methoxy) (e.g. Het$^2$ represents a 5- or 6-membered, aromatic heterocyclic group containing one or two heteroatoms selected from oxygen and nitrogen, such as an unsubstituted pyridyl group);

(7) R$^{12a}$ represents $C_{1-6}$ alkyl, $C_{5-6}$ cycloalkyl (which latter two groups are optionally substituted by one or more substituents selected from halo, methyl and methoxy) or phenyl (which latter group is optionally substituted by one or more substituents selected from halo, methyl and methoxy);
(8) $R^2$ represents $C_{1-3}$ alkyl optionally substituted by one or more substituents selected from halo, OH and $N(H)R^{5g}$ (e.g. $R^2$ represents unsubstituted $C_{1-3}$ alkyl, such as methyl);
(9) $R^3$ represents one to three (e.g. one or two) substituents on the fused benzene ring selected from
$C_{1-3}$ alkyl (optionally substituted by one or more halo groups),
$N(H)R^{7h}$,
$Het^6$ or, particularly,
$OR^{7a}$
(such as one to three (e.g. one or two) substituents on the fused benzene ring selected from $C_{1-3}$ alkyl (optionally substituted by one or more halo groups) or, particularly, $OR^{7a}$);
(10) $R^{7a}$ represents, independently at each occurrence,
$C_{1-6}$ alkyl (optionally substituted by one or more substituents selected from halo and phenyl (which latter group is optionally substituted by one or more substituents selected from halo, $C_{1-4}$ alkyl and $C_{1-4}$ alkoxy)),
$C_{5-6}$ cycloalkyl (optionally substituted by one or more substituents selected from halo, methyl and methoxy),
phenyl (which latter group is optionally substituted by one or more substituents selected from halo, $C_{1-4}$ alkyl and $C_{1-4}$ alkoxy) or
$Het^9$;
(11) $R^{7a}$ represents phenyl optionally substituted by one or more substituents selected from halo, $C_{1-4}$ alkyl and $C_{1-4}$ alkoxy);
(12) $Het^6$ represents a 5- or 6-membered fully saturated heterocyclic group containing one or two heteroatoms selected from oxygen and nitrogen (e.g. a piperidinyl (such as a piperidin-1-yl) group), which group is optionally substituted by one or more $C_{1-2}$ alkyl groups;
(13) $Het^9$ represents a 5- to 10-membered, aromatic heterocyclic group containing from one to four heteroatoms selected from oxygen, nitrogen and/or sulfur, which heterocyclic group comprises either one or two rings and is optionally substituted by one or more substituents selected from halo, $C_{1-3}$ alkyl (e.g. methyl) and $C_{1-3}$ alkoxy (e.g. methoxy);
(14) X represents $-CH_2-CH_2-$.

In one particular embodiment of the invention, the compound of formula I may be represented as a compound of formula Ia,

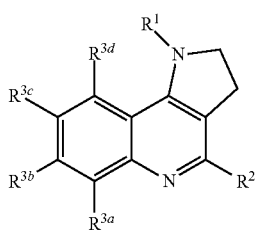

Ia wherein $R^1$ and $R^2$ are as hereinbefore defined and each of $R^{3a}$ to $R^{3d}$ represents either H or a substituent as hereinbefore defined in relation to the group $R^3$.

Hereinafter, references to compounds of formula I are, unless the context indicates otherwise, intended to include references to compounds of formula Ia. Conversely, where reference is made to particular embodiments of the compounds of formula Ia, these embodiments apply equally, where relevant, to compounds of formula I.

Particular embodiments of the compounds of formula Ia that may be mentioned include those in which:
(1) one or both of $R^{3a}$ and $R^{3c}$ represent a substituent as hereinbefore defined in relation to the group $R^3$, and $R^{3b}$ and $R^{3d}$ both represent H;
(2) $R^{3a}$ and $R^{3c}$ independently represent H, $OR^{7a}$, $N(H)R^{7h}$ or $Het^6$ (e.g. H or $OR^{7a}$), wherein $R^{7a}$, $R^{7h}$ and $Het^6$ are as hereinbefore defined, provided that $R^{3a}$ and $R^{3c}$ do not both represent H.

More particular embodiments of the compounds of formula Ia that may be mentioned include those in which:
$R^1$ represents
$C_{1-5}$ alkyl (which latter group is optionally substituted by $C_{3-5}$ cycloalkyl (e.g. cyclopropyl), phenyl (which latter group is optionally substituted by one or more substituents selected from halo, methyl and methoxy), phenoxy, benzodioxanyl (e.g. benzodioxan-2-yl) or benzodioxolyl (e.g. benzodioxol-5-yl)),
$C_{3-6}$ cycloalkyl (which latter group is optionally fused to a benzene ring (e.g. to provide a cycloalkyl group such as cyclopropyl, or a benzo-fused cycloalkyl group such as 1,2,3,4-tetrahydronaphthyl or indanyl (e.g. indan-2-yl, indan-1-yl, (S)-indan-1-yl or (R)-indan-1-yl))),
phenyl (which latter group is optionally substituted by one or more substituents (e.g. one or two substituents, such as a single substituent in the 4-position) selected from halo (e.g. fluoro), $C_{1-4}$ alkyl (e.g. methyl or, particularly, iso-propyl), OH, $C_{1-4}$ alkoxy (which latter group is optionally substituted by $N(CH_3)_2$, providing, for example, a methoxy or $OCH_2CH_2N(CH_3)_2$ group), phenoxy (which latter group is either unsubstituted or is substituted by one or more, e.g. one or two, substituents selected from methoxy or, particularly, halo (such as fluoro)), pyridyloxy (e.g. pyrid-3-yloxy) and piperazinyl (optionally substituted by methyl, providing, for example, 4-methylpiperazin-1-yl),
pyridyl (e.g. pyrid-3-yl), which latter group is optionally substituted (e.g. in the 6-position) by methoxy or phenoxy, or piperidinyl (e.g. piperidin-4-yl), which latter group is optionally substituted (e.g. at the 1-position) by $C_{1-2}$ alkyl (which latter group is optionally substituted by phenyl, providing, for example, benzyl);
$R^{3a}$ and $R^{3a}$ independently represent
H,
$C_{1-4}$ alkoxy (optionally substituted by one or more halo atoms (e.g. to provide a substituted alkoxy group such as trifluoromethoxy or, particularly, an unsubstituted alkoxy group such as methoxy or ethoxy)),
$-N(H)$-(phenyl), the phenyl part of which latter group is (optionally substituted by one or more substituents selected from halo, methyl and methoxy),
a 5- or 6-membered N-linked, fully saturated heterocycle containing an N-atom (that via which the group is linked) and optionally containing one further heteroatom selected from N and O (e.g. a piperidin-1-yl group) or
phenoxy (optionally substituted by one or more substituents selected from halo, methyl and methoxy),
(e.g. $R^{3a}$ and $R^{3c}$ independently represent H, $C_{1-4}$ alkoxy (optionally substituted by one or more halo atoms (e.g. to provide a substituted alkoxy group such as trifluoromethoxy or, particularly, an unsubstituted alkoxy group such as methoxy or ethoxy)), or phenoxy (optionally substituted by one or more substituents selected from halo, methyl and methoxy)), provided that $R^{3a}$ and $R^{3c}$ do not both represent H.

Further, in compounds of formula Ia, embodiments of the group $R^1$ that may be mentioned include phenyl substituted (e.g. at the 4-position) by a $C_{3-12}$ alkyl group (e.g. a branched $C_{3-12}$ alkyl group, such as iso-propyl), and optionally further substituted as defined above in respect of $R^1$ (when that group represents aryl).

Specific embodiments of the compounds of formula Ia that may be mentioned further include those in which:
(1) $R^{3a}$ and $R^{3c}$ are both other than H (e.g. $R^{3a}$ and $R^{3c}$ both represent $OR^{7a}$, wherein $R^{7a}$ is as hereinbefore defined), and $R^{3b}$ and $R^{3d}$ both represent H;
(2) $R^{3a}$ is other than H (e.g. $R^{3a}$ represents $OR^{7a}$, wherein $R^{7a}$ is as hereinbefore defined), and $R^{3b}$, $R^{3c}$ and $R^{3d}$ all represent H; or, particularly,
(3) $R^{3c}$ is other than H (e.g. $R^{3c}$ represents $OR^{7a}$, wherein $R^{7a}$ is as hereinbefore defined), and $R^{3a}$, $R^{3c}$ and $R^{3d}$ all represent H.

Specific values of $R^1$ that may be mentioned in relation to compounds of formula I include 3-methylbut-1-yl, 1-methylbenzimidazol-2-yl, cyclopropyl, cyclopropylmethyl, 2-phenoxyethyl, benzodioxol-5-ylmethyl, 6-methoxypyridin-3-yl, 6-phenoxypyridin-3-yl, 3-hydroxyphenyl, 3-hydroxy-5-methylphenyl, 4-hydroxyphenyl, 4-(2-dimethylaminoethoxy)phenyl, 3-fluoro-4-(4-methylpiperazin-1-yl)phenyl, 4-(pyridin-3-yloxy)phenyl or, particularly, benzodioxan-2-ylmethyl, 1-benzylpiperidin-4-yl, cyclohexyl, 1,2,3,4-tetrahydronaphth-1-yl, 1-phenylethyl, 2-phenylethyl, phenyl, 4-iso-propylphenyl, 4-methoxyphenyl, 3-phenoxyphenyl, 4-phenoxyphenyl, benzyl, (2-methylphenyl)methyl, indan-1-yl or indan-2-yl.

Other specific values of $R^1$ that may be mentioned in relation to compounds of formula I include 3-methoxypropyl, ethoxycarbonylmethyl, 2-(methoxycarbonyl)ethyl, 2-(ethoxycarbonyl)ethyl, 3-(methoxycarbonyl)propyl, 3-(ethoxycarbonyl)propyl, 1-benzylpyrrolidin-3-yl, 1-methylpiperidin-4-yl, tetrahydrofuran-2-ylmethyl, 2-pyridylmethyl, 5-methylpyrazin-2-ylmethyl, 2-(2-pyridyl)ethyl, 2-(3-pyridyl)ethyl, 3-(1-pyrrolidin-2-onyl)propyl, 2-methylphenyl, 4-(piperidin-1-yl)phenyl, 4-(3-pyridyl)phenyl, 2-phenylpropyl or, particularly, (S)-indan-1-yl, (R)-indan-1-yl, 2-(4-chlorophenyl)ethyl, 2-(4-methoxyphenyl)ethyl or 4-(4-fluorophenoxy)phenyl.

Particular compounds of formula Ia that may be mentioned include those of the following formula,

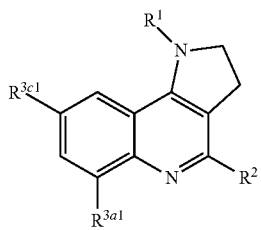

wherein:
$R^1$ and $R^2$ are as hereinbefore defined;
$R^{3a1}$ represents H and $R^{3c1}$ represents phenoxy, or, when $R^1$ represents
  $C_{1-2}$ alkyl substituted by optionally substituted phenyl (e.g. benzyl, (2-methylphenyl)methyl, 1-phenylethyl or, particularly, 2-phenylethyl),
  $C_{5-6}$ cycloalkyl fused to a benzene ring (e.g. 1,2,3,4-tetrahydronaphthyl, indan-1-yl or, particularly, indan-2-yl), or
  phenyl substituted by phenoxy,
then $R^{3a1}$ can additionally represent methoxy, or phenoxy and $R^{3c1}$ can additionally represent H, methoxy, trifluoromethoxy or ethoxy,
provided that $R^{3a1}$ and $R^{3c1}$ do not both represent phenoxy.

The medicament mentioned in the first aspect of the invention may be utilised in a method of medical treatment. Thus, according to a second aspect of the invention, there is provided a method of killing clinically latent microorganisms in a mammal infected with such latent microorganisms, the method comprising administering to said mammal a microbicidally effective amount of compound of formula I, as hereinbefore defined.

Furthermore, the compound of formula I may be used to kill clinically latent microorganisms. Thus, according to a third aspect of the invention, there is provided the use of a compound of formula I, as hereinbefore defined, to kill clinically latent microorganisms. In one embodiment, the use according to this aspect of the invention is an ex vivo use.

In addition to killing clinically latent microorganisms, the inventors have discovered that compounds of formula I are able to kill microorganisms of many different phenotypes, including growing microorganisms.

In this respect, fourth, fifth and sixth aspects of the invention provide, respectively:
(a) the use of a compound of formula I, as hereinbefore defined, for the preparation of a medicament for the treatment of a microbial infection;
(b) a method of treating or preventing a microbial infection in a mammal, the method comprising administering to said mammal an antimicrobially effective amount of a compound of formula I, as hereinbefore defined;
(c) use (e.g. ex vivo use) of a compound of formula I to kill microorganisms.

For the avoidance of doubt, as used herein, the term "treatment" includes therapeutic and/or prophylactic treatment.

In the fourth to sixth aspects of the invention, it is preferred that the compound of formula I is not:
(i) 1,4-dimethyl-2,3-dihydro-1H-pyrrolo[3,2-c]quinoline;
(ii) 1-[2-hydroxyethyl]-4-methyl-2,3-dihydro-1H-pyrrolo[3,2-c]quinoline;
(iii) 4-methyl-1-phenyl-2,3-dihydro-1H-pyrrolo[3,2-c]quinoline;
(iv) 4-methyl-1-(4-methylphenyl)-2,3-dihydro-1H-pyrrolo[3,2-c]quinoline;
(v) 4-methyl-1-(4-methoxyphenyl)-2,3-dihydro-1H-pyrrolo[3,2-c]quinoline;
(vi) 4-methyl-1-(2-chlorophenyl)-2,3-dihydro-1H-pyrrolo[3,2-c]quinoline;
(vii) 6-methoxy-4-methyl-1-phenyl-2,3-dihydro-1H-pyrrolo[3,2-c]quinoline;
(viii) 6-hydroxy-1,4-dimethyl-2,3-dihydro-1H-pyrrolo[3,2-c]quinoline;
(ix) 6-hydroxy-1-[2-hydroxyethyl]-4-methyl-2,3-dihydro-1H-pyrrolo[3,2-c]quinoline; or
(x) 6-hydroxy-4-methyl-1-phenyl-2,3-dihydro-1H-pyrrolo[3,2-c]quinoline.

As mentioned above, the uses according to the third and sixth aspects of the invention may be ex vivo uses, such as the use of a compound of formula I, as hereinbefore defined:
(a) as a sterilising agent; or
(b) as a preservative.

Conversely, the compounds of formula I may be employed in methods of sterilisation or preservation, such as:
(i) a method of sterilising an object, the method comprising applying to said object a compound of formula I, as hereinbefore defined; or
(ii) a method of preserving an inorganic or, preferably, an organic material, said method comprising contacting, combining or mixing said material with a compound of formula I, as hereinbefore defined.

In relation to the method described at (i) above, the object is preferably other than a human or animal body. Further, the materials that may be preserved according to the method described at (ii) above include polymers, lubricants, paints, fibres, leather, paper, foodstuffs, water and aqueous mixtures and solutions.

When used to kill clinically latent microorganisms or to treat a microbial infection, the compounds of formula I may be used either alone (i.e. as sole microbicidal or antimicrobial agents) or in combination with any one or more of the conventional antimicrobial agents described above.

Further, when used as a sterilising agent, the compounds of formula I may be used either alone or in combination with a conventional sterilising agent. The term "conventional sterilising agent", when used herein, includes references to alcohols (e.g. industrial methylated spirits or ethanol), sodium chloride, thymol, chlorhexidine, cationic surfactants (e.g. cetrimide), iodine (optionally combined with povidone), phenolics (e.g. triclosan), oxidants (e.g. hydrogen peroxide, potassium permanganate or sodium hypochlorite) and any one or more of the conventional antimicrobial agents described above.

Thus, according to seventh and eighth aspects of the invention, there is provided, respectively:
(i) a combination product comprising
  (A) a compound of formula I, as hereinbefore defined, and
  (B) a conventional antibiotic agent, as hereinbefore defined, wherein each of components (A) and (B) is formulated in admixture with a pharmaceutically-acceptable adjuvant, diluent or carrier; and
(b) a formulation comprising a compound of formula I, as hereinbefore defined and a conventional sterilising agent, as hereinbefore defined, or a salt and/or solvate thereof.

The combination product according to the seventh aspect of the invention provides for the administration of component (A) in conjunction with component (B), and may thus be presented either as separate formulations, wherein at least one of those formulations comprises component (A) and at least one comprises component (B), or may be presented (i.e. formulated) as a combined preparation (i.e. presented as a single formulation including component (A) and component (B)).

Thus, there is further provided:
(1) a pharmaceutical formulation including a compound of formula I, as hereinbefore defined and a conventional antimicrobial agent, as hereinbefore defined, or a pharmaceutically-acceptable derivative thereof, in admixture with a pharmaceutically-acceptable adjuvant, diluent or carrier (which formulation is hereinafter referred to as a "combined preparation"); and
(2) a kit of parts comprising components:
  (I) a pharmaceutical formulation including a compound of formula I, as hereinbefore defined, in admixture with a pharmaceutically-acceptable adjuvant, diluent or carrier; and
  (II) a pharmaceutical formulation including a conventional antimicrobial agent, as hereinbefore defined, or a pharmaceutically-acceptable derivative thereof, in admixture with a pharmaceutically-acceptable adjuvant, diluent or carrier,
  which components (I) and (II) are each provided in a form that is suitable for administration in conjunction with the other.

Component (I) of the kit of parts is thus component (A) in admixture with a pharmaceutically-acceptable adjuvant, diluent or carrier. Similarly, component (II) is component (B) in admixture with a pharmaceutically-acceptable adjuvant, diluent or carrier.

According to a ninth aspect of the invention, there is provided a method of making a kit of parts as defined above, which method comprises bringing a component (I), as defined above, into association with a component (II), as defined above, thus rendering the two components suitable for administration in conjunction with each other.

By bringing the two components "into association with" each other, we include that components (I) and (II) of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Thus, there is further provided a kit of parts comprising:
(1) one of components (I) and (II) as defined herein; together with
(2) instructions to use that component in conjunction with the other of the two components.

The kits of parts described herein may comprise more than one formulation including an appropriate quantity/dose of component (A), and/or more than one formulation including an appropriate quantity/dose of component (B), in order to provide for repeat dosing. If more than one formulation (comprising either active compound) is present, such formulations may be the same, or may be different in terms of the dose of component (A) or component (B), chemical composition and/or physical form.

The combination product according to the seventh aspect of the invention may be used to kill clinically latent microorganisms and/or treat a microbial infection. Thus, further aspects of the invention provide:
(i) the use of a combination product according to the seventh aspect of the invention for the preparation of a medicament for killing clinically latent microorganisms;
(ii) a method of killing clinically latent microorganisms in a mammal, the method comprising administering to said mammal a microbicidally effective amount of a combination product according to the seventh aspect of the invention;
(iii) the use of a combination product according to the seventh aspect of the invention for the preparation of a medicament for treating a microbial infection; and
(iv) a method of treating or preventing a microbial infection in a mammal, the method comprising administering to said mammal an antimicrobially effective amount of a combination product according to the seventh aspect of the invention.

The method of (iv) above provides for the advantage that the amount of conventional antimicrobial agent required to treat the microbial infection is reduced compared to that required in the absence of a compound of formula I.

When used herein, the terms "bacteria" (and derivatives thereof, such as "bacterial infection") includes references to organisms (or infections due to organisms) of the following classes and specific types:

Gram-positive cocci, such as
- Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*) and
- Streptococci (e.g.
  - beta-haemolytic, pyogenic streptococci (such as *Strept. agalactiae, Strept. canis, Strept. dysgalactiae dysgalactiae, Strept. dysgalactiae equisimilis, Strept. equi equi, Strept. equi zooepidemicus, Strept. iniae, Strept. porcinus* and *Strept. pyogenes*),
  - microaerophilic, pyogenic streptococci (*Streptococcus "milleri"*, such as *Strept. anginosus, Strept. constellatus constellatus, Strept. constellatus pharyngidis* and *Strept. intermedius*),
  - oral streptococci of the "*mitis*" (alpha-haemolytic—*Streptococcus "viridans"*, such as *Strept. mitis, Strept. oxalis, Strept. sanguinis, Strept. cristatus, Strept. gordonii* and *Strept. parasanguinis*), "*salivarius*" (non-haemolytic, such as *Strept. salivarius* and *Strept. vestibularis*) and "*mutans*" (tooth-surface streptococci, such as *Strept. criceti, Strept. mutans, Strept. ratti* and *Strept. sobrinus*) groups,
  - *Strept. acidominimus, Strept. bovis, Strept. faecalis, Strept. equinus, Strept. pneumoniae* and *Strept. suis,*
  - or Streptococci alternatively classified as Group A, B, C, D, E, G, L, P, U or V *Streptococcus*);
- Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri;*
- Bacillaceae, such as *Bacillus anthracis, Bacillus subtilis, Bacillus thuringiensis, Bacillus stearothermophilus* and *Bacillus cereus;*
- Enterobacteriaceae, such as
  - *Escherichia coli,*
  - Enterobacter (e.g. *Enterobacter aerogenes, Enterobacter agglomerans* and *Enterobacter cloacae*)
  - Citrobacter (such as *Citrob. freundii* and *Citrob. diversinis*),
  - Hafnia (e.g. *Hafnia alvei*),
  - Erwinia (e.g. *Erwinia persicinus*),
  - *Morganella morganii,*
  - Salmonella (*Salmonella enterica* and *Salmonella typhi*),
  - Shigella (e.g. *Shigella dysenteriae, Shigella flexneri, Shigella boydii* and *Shigella sonnei*),
  - Klebsiella (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*),
  - Proteus (e.g. *Pr. mirabilis, Pr. rettgeri* and *Pr. vulgaris*),
  - Providencia (e.g. *Providencia alcalifaciens, Providencia rettgeri* and *Providencia stuartii*),
  - Serratia (e.g. *Serratia marcescens* and *Serratia liquifaciens*), and
  - Yersinia (e.g. *Yersinia enterocolitica, Yersinia pestis* and *Yersinia pseudotuberculosis*);
- Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*);
- Helicobacter (e.g. *Helicobacter pylori, Helicobacter cinaedi* and *Helicobacter fennelliae*);
- Acinetobacter (e.g. *A. baumanii, A. calcoaceticus, A. haemolyticus, A. johnsonii, A. junii, A. lwoffi* and *A. radioresistens*);
- Pseudomonas (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzeri*);
- *Bacteriodes fragilis;*
- Peptococcus (e.g. *Peptococcus niger*);
- *Peptostreptococcus;*
- Clostridium (e.g. *C. perfringens, C. difficile, C. botulinum, C. tetani, C. absonum, C. argentinense, C. baratii, C. bifermentans, C. beijerinckii, C. butyricum, C. cadaveris, C. carnis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tertium*);
- Mycoplasma (e.g. *M. pneumoniae, M. hominis, M. genitalium* and *M. urealyticum*);
- Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae,*

*Mycobacterium szulgai, Mycobacterium terse, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*);

*Haemophilus* (e.g. *Haemophilus influenzae, Haemophilus ducreyi, Haemophilus aegyptius, Haemophilus parainfluenzae, Haemophilus haemolyticus* and *Haemophilus parahaemolyticus*);

*Actinobacillus* (e.g. *Actinobacillus actinomycetemcomitans, Actinobacillus equuli, Actinobacillus hominis, Actinobacillus lignieresii, Actinobacillus suis* and *Actinobacillus ureae*);

*Actinomyces* (e.g. *Actinomyces israelii*);

*Brucella* (e.g. *Brucella abortus, Brucella canis, Brucella melintensis* and *Brucella suis*);

*Campylobacter* (e.g. *Campylobacter jejuni, Campylobacter coli, Campylobacter lari* and *Campylobacter fetus*);

*Listeria monocytogenes;*

*Vibrio* (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*);

*Erysipelothrix rhusopathiae;*

Corynebacteriaceae (e.g. *Corynebacterium diphtheriae, Corynebacterium jeikeum* and *Corynebacterium urealyticum*);

Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*);

*Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*);

*Bordetella* (e.g. *Bordetella bronchiseptica, Bordetella hinzii, Bordetella holmseii, Bordetella parapertussis, Bordetella pertussis* and *Bordetella trematum*);

Nocardiaceae, such as *Nocardia* (e.g. *Nocardia asteroides* and *Nocardia brasiliensis*);

*Rickettsia* (e.g. Ricksettsii or *Coxiella burnetii*);

*Legionella* (e.g. *Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israelensis, Legionalla jordanis, Legionalla lansingensis, Legionalla longbeachae, Legionalla maceachernii, Legionalla micdadei, Legionalla oakridgensis, Legionalla pneumophila, Legionalla sainthelensi, Legionalla tucsonensis* and *Legionalla wadsworthii*);

*Moraxella catarrhalis;*

*Stenotrophomonas maltophilia;*

*Burkholderia cepacia;*

*Francisella tularensis;*

*Gardnerella* (e.g. *Gardneralla vaginalis* and *Gardneralla mobiluncus*);

*Streptobacillus moniliformis;*

Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*);

*Bartonella* (*Bartonella bacilliformis, Bartonella clarridgeiae, Bartonella elizabethae, Bartonella henselae, Bartonella quintana* and *Bartonella vinsonii arupensis*);

*Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*);

*Spirillium* (e.g. *Spirillum minus*);

*Baceteroides* (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*);

*Prevotella* (e.g. *Prevotella bivia, Prevotella buccae, Prevotella corporis, Prevotella dentalis* (*Mitsuokella dentalis*), *Prevotella denticola, Prevotella disiens, Prevotella enoeca, Prevotella heparinolytica, Prevotella intermedia, Prevotella loeschii, Prevotella melaminogenica, Prevotella nigrescens, Prevotella oxalis, Prevotella oris, Prevotella oulora, Prevotella tannerae, Prevotella venoralis* and *Prevotella zoogleoformans*);

*Porphyromonas* (e.g. *Porphyromonas asaccharolytica, Porphyromonas cangingivalis, Porphyromonas canons, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*);

*Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);

*Chlamydia* (e.g. *Chlamydia trachomatis*);

*Chlamydophila* (e.g. *Chlamydophila abortus* (*Chlamydia psittaci*), *Chlamydophila pneumoniae* (*Chlamydia pneumoniae*) and *Chlamydophila psittaci* (*Chlamydia psittaci*));

*Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*);

*Gemella* (e.g. *Gemella bergeri, Gemella haemolysans, Gemella morbillorum* and *Gemella sanguinis*); and

*Ureaplasma* (e.g. *Ureaplasma parvum* and *Ureaplasma urealyticum*).

In one embodiment of the invention, the term "bacteria" includes references to any of the above classes or specific types of organisms, except for *Shigella* (e.g. *Shigella flexneri*) or *Salmonella* (e.g. *Salmonella typhi*).

When used herein, the terms "fungi" (and derivatives thereof, such as "fungal infection") includes references to organisms (or infections due to organisms) of the following classes and specific types:

Absidia (e.g. *Absidia corymbifera*);
Ajellomyces (e.g. *Ajellomyces capsulatus* and *Ajellomyces dermatitidis*);
Arthroderma (e.g. *Arthroderma benhamiae, Arthroderma fulvum, Arthroderma gypseum, Arthroderma incurvatum, Arthroderma otae* and *Arthroderma vanbreuseghemii*);
Aspergillus (e.g. *Aspergillus flavus, Aspergillus fumigatus* and *Aspergillus niger*);
Blastomyces (e.g. *Blastomyces dermatitidis*);
Candida (e.g. *Candida albicans, Candida glabrata, Candida guilliermondii, Candida krusei, Candida parapsilosis, Candida tropicalis* and *Candida pelliculosa*);
Cladophialophora (e.g. *Cladophialophora carrionii*);
Coccidioides (e.g. *Coccidioides immitis*);
Cryptococcus (e.g. *Cryptococcus neoformans*);
Cunninghamella (e.g. *Cunninghamella* sp.)
Epidermophyton (e.g. *Epidermophyton floccosum*);
Exophiala (e.g. *Exophiala dermatitidis*);
Filobasidiella (e.g. *Filobasidiella neoformans*);
Fonsecaea (e.g. *Fonsecaea pedrosoi*);
Fusarium (e.g. *Fusarium solani*);
Geotrichum (e.g. *Geotrichum candidum*);
Histoplasma (e.g. *Histoplasma capsulatum*);
Hortaea (e.g. *Hortaea werneckii*);
Issatschenkia (e.g. *Issatschenkia orientalis*);
Madurella (e.g. *Madurella grisae*);
Malassezia (e.g. *Malassezia furfur, Malassezia globosa, Malassezia obtusa, Malassezia pachydermatis, Malassezia restricta, Malassezia slooffiae* and *Malassezia sympodialis*);
Microsporum (e.g. *Microsporum canis, Microsporum fulvum* and *Microsporum gypseum*);
Mucor (e.g. *Mucor circinelloides*);
Nectria (e.g. *Nectria haematococca*);
Paecilomyces (e.g. *Paecilomyces variotii*);
Paracoccidioides (e.g. *Paracoccidioides brasiliensis*);
Penicillium (e.g. *Penicillium marneffei*);
Pichia (e.g. *Pichia anomala* and *Pichia guilliermondii*);
Pneumocystis (e.g. *Pneumocystis jiroveci (Pneumocystis carinii)*);
Pseudallescheria (e.g. *Pseudallescheria boydii*);
Rhizopus (e.g. *Rhizopus oryzae*);
Rhodotorula (e.g. *Rhodotorula rubra*);
Scedosporium (e.g. *Scedosporium apiospermum*);
Schizophyllum (e.g. *Schizophyllum commune*);
Sporothrix (e.g. *Sporothrix schenckii*);
Trichophyton (e.g. *Trichophyton mentagrophytes, Trichophyton rubrum, Trichophyton verrucosum* and *Trichophyton violaceum*); and
Trichosporon (e.g. *Trichosporon asahii, Trichosporon cutaneum, Trichosporon inkin* and *Trichosporon mucoides*).

Thus, compounds of formula I, or combination products comprising compounds of formula I, may be used to kill any of the above-mentioned bacterial or fungal organisms (clinically latent or otherwise).

Particular bacteria that may be mentioned in this respect include:

Staphylococci, such as *Staph. aureus* (either Methicillin-sensitive (i.e. MSSA) or Methicillin-resistant (i.e. MRSA)) and *Staph. epidermidis*;
Streptococci, such as *Strept. agalactiae* and *Strept. pyogenes;*
Bacillaceae, such as *Bacillus anthracis;*
Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*); *Haemophilis influenzae;*
Enterococci, such as *Enterococcus faecalis* and *Enterococcus faecium*; and
Mycobacteria, such as *Mycobacterium tuberculosis.*

Particular fungi that may also be mentioned in this respect include *Aspergillus fumigatus, Candida albicans, Cryptococcus neoformans, Histoplasma capsulatum* and *Pneumocystis jiroveci.*

Particular bacterial or fungal infections that may be mentioned in relation to (i) the use according to the fourth aspect of the invention,
(ii) the method according to the sixth aspect of the invention and
(iii) the above-described use and method involving the combination product according to the seventh aspect of the invention (i.e. use (iii) above or method (iv) above), include infections with Staph. aureus (either Methicillin-sensitive (i.e. MSSA) or Methicillin-resistant (i.e. MRSA)) and *Staph. epidermidis,*
Streptococci, such as *Strept. agalactiae* and *Strept. pyogenes,*
Bacillaceae, such as *Bacillus anthracis,*
Enterobacteriaceae, such as *Escherichia coli, Klebsiella* (e.g. *Klebs. pneumoniae* and *Klebs.* oxytoca) and *Proteus* (e.g. *Pr. mirabilis, Pr. rettgeri* and *Pr. vulgaris*), *Haemophilis influenzae,*
Enterococci, such as *Enterococcus faecalis* and *Enterococcus faecium,*
Mycobacteria, such as *Mycobacterium tuberculosis* or fungi such as *Aspergillus fumigatus, Candida albicans, Cryptococcus neoformans, Histoplasma capsulatum* and *Pneumocystis jiroveci.*

In this respect, particular conditions that the compounds of formula I, or combination products comprising compounds of formula I, can be used to treat include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, actinomycosis, bacilliary dysentry, bacterial conjunctivitis, bacterial keratitis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, empymea, endocarditis, endometritis, enteric fever, enteritis, epididymitis, epiglottitis, erysipclas, erysipeloid, erythrasma, eye infections, furuncles, *Gardnerella* vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, Ritter's disease, salmonellosis, salpingitis, septic arthritis, septic infections, septicameia, sinusitis, skin infections (e.g. skin granulomas), syphilis, systemic infections, tonsillitis, toxic shock syndrome, trachoma, tularaemia, typhoid, typhus (e.g. epidemic typhus, murine typhus, scrub typhus and spotted fever), urethritis, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea capitis, tinea cruris, tinea pedis and tinea unguium), onychomycosis, pityriasis versicolor, ringworm and sporotrichosis.

Further conditions that may be mentioned in this respect include infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilus influenzae, Enterococcus faecalis* or *Enterococcus faecium.*

Specific compounds of formula I that may be mentioned in relation to the above-described aspects of the invention include the following compounds:
(a) 6,8-dimethoxy-1-(4-iso-propylphenyl)-4-methyl-2,3-dihydro-1H-pyrrolo[3,2-c]quinoline;
(b) 6-methoxy-1-(4-phenoxyphenyl)-4-methyl-2,3-dihydro-1H-pyrrolo[3,2-c]quinoline;
(c) 6-methoxy-1-(4-iso-propylphenyl)-4-methyl-2,3-dihydro-1H-pyrrolo[3,2-c]quinoline;
(d) 6,8-dimethoxy-1-(4-phenoxyphenyl)-4-methyl-2,3-dihydro-1H-pyrrolo[3,2-c]quinoline;
(e) 4-methyl-8-phenoxy-1-(4-phenoxyphenyl)-2,3-dihydro-1H-pyrrolo[3,2-c]quinoline;
(f) 1-(4-iso-propylphenyl)-6-phenoxy-4-methyl-2,3-dihydro-1H-pyrrolo[3,2-c]quinoline; and
(g) 4,6-dimethyl-1-(4-methylphenyl)-2,3-dihydro-1H-pyrrolo[3,2-c]quinoline,
as well as, particularly, the compounds of Examples 1 to 8 below.

The use of certain compounds of formula I in medicine, including compounds of formula I (and Ia), as hereinbefore defined, is, to the knowledge of the inventors, novel.

For the avoidance of doubt, references herein to compounds of formula I include references to all embodiments described above in relation to compounds of formulae I and Ia.

In this respect, a further aspect of the invention provides a compound of formula Ib for use in medicine, wherein compounds of formula Ib take the same definition as compounds of formula I, as hereinbefore defined, except that the compound is not:
(a) of the following formula

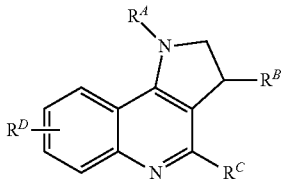

in which
(i) $R^A$ represents methyl, benzyl or $CH_2CH_2N(C_{1-2}$ alkyl$)_2$,
$R^B$ represents H,
$R^C$ represents H or methyl and
$R^D$ represents H or one or two substituents selected from Cl, OH,
$C_{1-2}$ alkoxy and $C(O)N(H)CH_3$, (ii) $R^A$ represents $CH(C_2H_5)_2$ or $CH(C_2H_5)(CH_2OCH_3)$,
$R^B$ represents H,
$R^C$ represents methyl or 2,4,6-trimethylphenyl and
$R^D$ represents a single substituent selected from 2,4,6-trimethylphenyl and iodo,
(iii) $R^A$ represents benzyl, 1-phenylethyl or phenyl, which latter group is substituted at the 2-position by methyl or methoxy and is optionally further substituted at the 4-position by fluoro, OH, methyl, methoxy or benzyloxy, or at the 6-position by methyl,
$R^B$ represents H, $C_{1-3}$ alkyl (e.g. methyl, ethyl or iso-propyl) or $C_{1-2}$ alkyl terminated by OH,
$R^C$ represents H, methyl or hydroxymethyl and
$R^D$ represents H or a single substituent (e.g. at the 6-position) selected from F, OH, methyl, methoxy, trifluoromethoxy, $OCH_2CH_2OH$ or $OCH_2CF_3$,
(iv) $R^A$ represents methyl, 2-hydroxyethyl or phenyl, which latter group is optionally singly substituted in the 2-position by chloro or in the 4-position by methyl or methoxy,
$R^B$ represents H,
$R^C$ represents methyl and
$R^D$ represents H or a single substituent (e.g. at the 6-position) selected from OH and methoxy,
(v) $R^A$ represents phenyl substituted by a single OH or methoxy group,
$R^B$ represents H,
$R^C$ represents methyl and
$R^D$ represents H or
(vi) $R^A$ represents H or phenyl optionally substituted by a single substituent (e.g. at the 4-position) selected from methyl, chloro or fluoro, or by a single trifluoromethyl substituent (e.g. at the 3-position),
$R^B$ represents H,
$R^C$ represents methyl and
$R^D$ represents a single chloro or fluoro substituent (e.g. at the 8-position) or two substituents (e.g. at the 6- and 8- or 6- and 9-positions) which are both either chloro or methoxy; or
(b) of the following formula

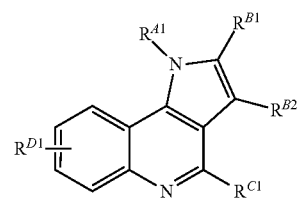

in which
(i) $R^{A1}$ represents 2-ethoxyethyl or $CH(R^{alk1})(R^{alk2})$, wherein $R^{alk1}$ and
$R^{alk2}$ independently represent ethyl, n-propyl or methoxymethyl,
$R^{B1}$ and $R^{B2}$ both represent H,
$R^{C1}$ represents methyl or 2,4,6-trimethylphenyl and
$R^{D1}$ represents a single substituent (e.g. at the 6- or 7-position) that is selected from iodo, methyl, aryl or Het$^6$, wherein aryl and Het$^6$ are as hereinbefore defined, or $R^{D1}$ represents a methyl substituent at the 6-position and a mesityl substituent at the 7-position,
(ii) $R^{A1}$ represents $C_{1-2}$ alkyl, 1-phenylethyl or phenyl, which latter group is substituted at the 2-position by methyl or methoxy and is optionally further substituted at the 4-position by F, OH, methoxy, acetoxy or benzyloxy,
$R^{B1}$ represents H,
$R^{B2}$ represents H, $C_{1-3}$ alkyl or $C_{1-2}$ alkyl terminated by OH,
$R^{C1}$ represents H or methyl and
$R^{D1}$ represents a single substituent (e.g. at the 6-position) that is selected from Cl, OH, methoxy, trifluoromethoxy, $OCH_2CH_2OH$ or $OCH_2CF_3$,
(iii) $R^{A1}$ represents methyl, n-butyl, benzyl or phenyl, which latter group is substituted at the 2-position by methyl and is optionally further substituted at the 4-position by F, methoxy, OC(O)O-1-butyl or OC(O)-i-butyl,
$R^{B1}$ represents H, methyl, hydroxymethyl, n-propyl or phenyl,
$R^{B2}$ represents H, $C_{1-3}$ alkyl, hydroxymethyl or phenyl,
$R^{C1}$ represents H or methyl and
$R^{D1}$ represents a single substituent (e.g. at the 6-position) that is selected from Cl and methoxy,
(iv) $R^{A1}$ represents phenyl, which group is optionally substituted by F or methoxy,
$R^{B1}$, $R^{B2}$ and $R^{C1}$ all represent trifluoromethyl and
$R^{D1}$ represents H or a single substituent that is selected from F and methoxy,
(v) $R^{A1}$, $R^{B1}$, $R^{B2}$ and $R^{C1}$ all represent methyl and
$R^{D1}$ represents one or two substituents selected from Cl, methyl and methoxy,
(vi) $R^{A1}$ represents methyl, ethyl, 2-ethoxyethyl, 2-isopropoxyethyl, 3-methoxypropyl, n-butyl or phenyl,
$R^{B1}$ represents methyl, hydroxymethyl or n-propyl,
$R^{B2}$ represents H or phenyl,
$R^{C1}$ represents H or methyl and
$R^{D1}$ represents a single substituent (e.g. at the 6-position) that is selected from Cl, methoxy and 2,4,6-trimethylphenyl or
(vii) $R^{A1}$ represents phenyl,
$R^{B1}$ and $R^{B2}$ both represent H,
$R^{C1}$ represents methyl and
$R^{D1}$ represents H or a single methoxy substituent (e.g. at the 8-position).

The use of compounds of formula Ib in medicine includes their use as pharmaceuticals. The invention therefore further provides for the use of a compound of formula Ib as a pharmaceutical.

Specific compounds of formula Ib that may be mentioned include the following compounds:
(a) 6,8-dimethoxy-1-(4-iso-propylphenyl)-4-methyl-2,3-dihydro-1H-pyrrolo[3,2-c]quinoline;
(b) 6-methoxy-1-(4-phenoxyphenyl)-4-methyl-2,3-dihydro-1H-pyrrolo[3,2-c]quinoline;
(c) 6-methoxy-1-(4-iso-propylphenyl)-4-methyl-2,3-dihydro-1H-pyrrolo[3,2-c]quinoline;
(d) 6,8-dimethoxy-1-(4-phenoxyphenyl)-4-methyl-2,3-dihydro-1H-pyrrolo[3,2-c]quinoline;
(e) 4-methyl-8-phenoxy-1-(4-phenoxyphenyl)-2,3-dihydro-1H-pyrrolo[3,2-c]quinoline;
(f) 1-(4-iso-propylphenyl)-6-phenoxy-4-methyl-2,3-dihydro-1H-pyrrolo[3,2-c]quinoline; and
(g) 4,6-dimethyl-1-(4-methylphenyl)-2,3-dihydro-1H-pyrrolo[3,2-c]quinoline,
as well as, particularly, the compounds of Examples 1 to 8 below.

Certain compounds of formula I, Ia and Ib are to the knowledge of the inventors, novel per se. Thus, in a still further aspect of the invention, there is provided a compound of formula Ic, wherein compounds of formula Ic take the same definition as compounds of formula Ib, as hereinbefore defined, except that the compound is not:
(a) of the following formula

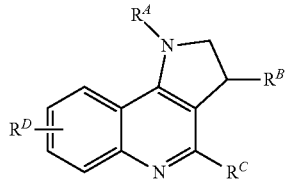

in which
(i) $R^A$ represents 2-(dimethylamino)ethyl,
$R^B$ represents H,
$R^C$ represents methyl and
$R^D$ represents one or two substituents selected from Cl, OH and methoxy,
(ii) $R^A$ represents phenyl substituted by one or two substituents consisting of an ethyl group at the 4-position or one or two methoxy groups at the 2- and/or 4-positions,
$R^B$ represents H,
$R^C$ represents methyl and
$R^D$ represents one or two substituents, at the 6- and/or 8-positions, selected from trifluoromethyl and methoxy or
(iii) $R^A$ represents methyl or phenyl, which latter group is optionally substituted by a single substituent selected from Cl, F, methyl, trifluoromethyl and methoxy, or by two methyl groups (e.g. at the 2- and 6-positions),
$R^B$ represents H,
$R^C$ represents H or methyl and
$R^D$ represents H or one or two substituents selected from Cl, F, methyl and methoxy; or
(b)
(i) 7,9-dibromo-6-hydroxy-4-methyl-1-phenyl-2,3-dihydro-1H-pyrrolo[3,2-c]quinoline,
(ii) 6-methoxy-4,5-dimethyl-1-(2-methylphenyl)-2,3-dihydro-1H-pyrrolo[3,2-c]quinolinium iodide;
(iii) 1-ethyl-5-methyl-2,3-dihydro-1H-pyrrolo[3,2-c]quinolinium hexafluorophosphate;
(iv) 6,8-dimethoxy-1-(4-iso-propylphenyl)-4-methyl-2,3-dihydro-1H-pyrrolo[3,2-c]quinoline,
(v) 6-methoxy-1-(4-phenoxyphenyl)-4-methyl-2,3-dihydro-1H-pyrrolo[3,2-c]quinoline,
(vi) 6-methoxy-1-(4-iso-propylphenyl)-4-methyl-2,3-dihydro-1H-pyrrolo[3,2-c]quinoline,
(vii) 6,8-dimethoxy-1-(4-phenoxyphenyl)-4-methyl-2,3-dihydro-1H-pyrrolo[3,2-c]quinoline,
(viii) 6,8-dimethoxy-1-(4-hydroxyphenyl)-4-methyl-2,3-dihydro-1H-pyrrolo[3,2-c]quinoline,
(ix) 6,9-dimethoxy-1,2,3,4-tetramethyl-1H-pyrrolo[3,2-c]quinoline,
(x) 6,9-dimethoxy-1,2,3,4,8-pentamethyl-1H-pyrrolo[3,2-c]quinoline,
(xi) 2,3-difluoro-1-phenyl-2,3,4-tris(trifluoromethyl)-2,3-dihydro-1H-pyrrolo[3,2-c]quinoline or
(xii) 6,9-dimethoxy-2,3,4,8-tetramethyl-2,3-dihydro-1H-pyrrolo[3,2-c]quinoline.

Compounds of formula Ic that may be mentioned include those that either (a) are, or (b) are not:
(xi) 1-(4-methoxyphenyl)-4-methyl-8-phenoxy-2,3-dihydro-1H-pyrrolo[3,2-c]quinoline, (xii) 4-methyl-8-phenoxy-1-(4-phenoxyphenyl)-2,3-dihydro-1H-pyrrolo[3,2-c]quinoline,
(xiii) 1-(4-iso-propylphenyl)-8-phenoxy-4-methyl-2,3-dihydro-1H-pyrrolo[3,2-c]quinoline,
(xiv) 1-(4-iso-propylphenyl)-6-phenoxy-4-methyl-2,3-dihydro-1H-pyrrolo[3,2-c]quinoline,
(xv) 6-phenoxy-1-(4-phenoxyphenyl)-4-methyl-2,3-dihydro-1H-pyrrolo[3,2-c]quinoline, or
(xvi) 6-phenoxy-1-(4-trifluoromethoxyphenyl)-4-methyl-2,3-dihydro-1H-pyrrolo[3,2-c]quinoline.

Particular compounds of formulae Ib and Ic that may be mentioned include those in which:
(a) $R^1$ is other than H;
(b) $R^2$ is other than H; and
(c) $R^1$ and $R^2$ are both other than H.

Compounds of formula Ic that may be mentioned include those in which:
(1) X represents —CH$_2$—CH$_2$—;
(2) $R^1$ represents
  (a) $C_{1-12}$ alkenyl, $C_{1-12}$ alkynyl, $C_{3-12}$ cycloalkyl or $C_{4-12}$ cycloalkenyl, which latter four groups are optionally substituted by one or more substituents selected from halo, nitro, CN, $C_{1-6}$ alkyl, $C_{1-6}$ alkenyl, $C_{1-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), OR$^{5a}$, S(O)$_p$R$^{5b}$, S(O)$_2$N(R$^{5c}$)(R$^{5d}$), N(R$^{5e}$)S(O)$_2$R$^{5f}$, N(R$^{5g}$)(R$^{5h}$), B$^3$—C(O)—B$^4$—R$^{5i}$, aryl and Het$^3$, and which $C_{3-12}$ cycloalkyl or $C_{4-12}$ cycloalkenyl groups may additionally be substituted by =O,
  (b) aryl substituted as defined above in respect of aryl groups, except that the substituents include at least one OR$^{10a}$ group in which R$^{10a}$ is other than H or $C_{1-12}$ alkyl (which latter group is optionally substituted as defined above in respect of R$^{10a}$) or
  (c) Het$^2$;
(3) $R^1$ represents
  (a) $C_{3-12}$ cycloalkyl, which latter groups is optionally fused to a benzene ring and is optionally substituted by one or more substituents selected from halo, nitro, CN, $C_{1-6}$ alkyl, $C_{1-6}$ alkenyl, $C_{1-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), OR$^{5a}$, =O, S(O)$_p$R$^{5b}$, S(O)$_2$N(R$^{5c}$)(R$^{5d}$), N(R$^{5e}$) S(O)$_2$R$^{5f}$, N(R$^{5g}$)(R$^{5h}$), B$^3$—C(O)—B$^4$—R$^{5i}$, aryl and Het$^3$,
  (b) phenyl substituted as defined above in respect of aryl groups, except that the substituents include at least one OR$^{10a}$ group in which R$^{10a}$ is phenyl (which latter group is optionally substituted by one or more substituents selected from OH, halo, methyl and methoxy) or
  (c) Het$^2$;
(4) $R^1$ represents
  (a) $C_{4-5}$ cycloalkyl fused to a benzene ring and optionally substituted by one or more substituents selected from halo, $C_{1-4}$ alkyl, OH and $C_{1-4}$ alkoxy or
  (b) phenyl substituted as defined above in respect of aryl groups, except that the substituents include at least one OR$^{10a}$ group in which R$^{10a}$ is phenyl (which latter group is optionally substituted by one or more substituents selected from OH, halo, methyl and methoxy);
(5) $R^3$ represents one to four substituents on the fused benzene ring, as defined above in respect of $R^3$, except that the substituents include at least one OR$^{7a}$ in which R$^{7a}$ is other than H or $C_{1-10}$ alkyl (which latter group is optionally substituted as defined above in respect of R$^{7a}$);
(6) $R^3$ represents one to four (e.g. one or two) substituents on the fused benzene ring, as defined above in respect of $R^3$, except that the substituents include at least one OR$^{7a}$ in which R$^{7a}$ is phenyl (which latter group is optionally substituted by one or more substituents selected from OH, halo, methyl and methoxy);
(7) $R^2$ represents unsubstituted $C_{1-3}$ alkyl, such as methyl.

Further, specific compounds of formula Ic that may be mentioned include compounds of Examples 1 to 8 below. Still further compounds of formula Ic that may be mentioned include compounds of Examples 1 to 8 below, except for the following compounds:
(1) 1-(4-methoxyphenyl)-4-methyl-8-phenoxy-2,3-dihydro-1H-pyrrolo[3,2-c]quinoline;
(2) 4-methyl-8-phenoxy-1-(4-iso-propylphenyl)-2,3-dihydro-1H-pyrrolo[3,2-c]quinoline; and
(3) 6,8-dimethoxy-1-(4-hydroxyphenyl)-4-methyl-2,3-dihydro-1H-pyrrolo[3,2-c]quinoline.

When used herein, the term "compounds of Examples 1 to 8 below" refers to the title compounds of those examples, i.e.:
(1) 6,8-dimethoxy-4-methyl-1-(3-phenoxyphenyl)-2,3-dihydro-1H-pyrrolo[3,2-c]-quinoline;
(2) 6,8-dimethoxy-4-methyl-1-(2-phenoxyethyl)-2,3-dihydro-1H-pyrrolo[3,2-c]-quinoline;
(3) 1-cyclopropyl-6,8-dimethoxy-4-methyl-2,3-dihydro-1H-pyrrolo[3,2-c]-quinoline;
(4) 8-methoxy-4-methyl-1-(4-phenoxyphenyl)-2,3-dihydro-1H-pyrrolo[3,2-c]-quinoline;
(5) {2-[4-(8-methoxy-4-methyl-2,3-dihydro-1H-pyrrolo[3,2-c]quinolin-1-yl)-phenyoxy]ethyl}dimethylamine;
(6) 8-methoxy-4-methyl-1-[4-(pyridin-3-yloxy)phenyl]-2,3-dihydro-1H-pyrrolo[3,2-c]quinoline;
(7) 4-methyl-8-phenoxy-1-phenyl-2,3-dihydro-1H-pyrrolo [3,2-c]quinoline;
(8) 1-benzyl-4-methyl-8-phenoxy-2,3-dihydro-1H-pyrrolo [3,2-c]quinoline
(9) 1-(indan-2-yl)-4-methyl-8-phenoxy-2,3-dihydro-1H-pyrrolo[3,2-c]quinoline
(10) 4-methyl-6-phenoxy-1-phenyl-2,3-dihydro-1H-pyrrolo [3,2-c]quinoline;
(11) 1-benzyl-4-methyl-6-phenoxy-2,3-dihydro-1H-pyrrolo [3,2-c]quinoline;
(12) 1-(indan-2-yl)-4-methyl-6-phenoxy-2,3-dihydro-1H-pyrrolo[3,2-c]quinoline;
(13) 4-methyl-1-(2-phenylethyl)-8-phenoxy-2,3-dihydro-1H-pyrrolo[3,2-c]-quinoline;
(14) 8-methoxy-4-methyl-1-(2-phenylethyl)-2,3-dihydro-1H-pyrrolo[3,2-c]-quinolin-6-ol;
(15) 1-(1-benzyl-piperidin-4-yl)-4-methyl-8-phenoxy-2,3-dihydro-1H-pyrrolo[3,2-c]quinoline;
(16) 1-(indan-1-yl)-4-methyl-8-phenoxy-2,3-dihydro-1H-pyrrolo[3,2-c]quinoline;
(17) 1-(benzodioxan-2-ylmethyl)-4-methyl-8-phenoxy-2,3-dihydro-1H-pyrrolo[3,2-c]quinoline;
(18) 4-methyl-8-phenoxy-1-(1,2,3,4-tetrahydronaphthalen-1-yl)-2,3-dihydro-1H-pyrrolo[3,2-c]quinoline;
(19) 1-cyclohexyl-4-methyl-8-phenoxy-2,3-dihydro-1H-pyrrolo[3,2-c]quinoline;
(20) 8-ethoxy-4-methyl-1-(4-phenoxyphenyl)-2,3-dihydro-1H-pyrrolo[3,2-c]-quinoline;
(21) 1-(4-methoxyphenyl)-4-methyl-8-phenoxy-2,3-dihydro-1H-pyrrolo[3,2-c]-quinoline;
(22) 4-methyl-1-(4-phenoxyphenyl)-2,3-dihydro-1H-pyrrolo[3,2-c]quinoline;
(23) 4-methyl-1-(2-methylphenyl)methyl-8-phenoxy-2,3-dihydro-1H-pyrrolo[3,2-c]quinoline;

(24) 4-methyl-8-phenoxy-1-(4-iso-propylphenyl)-2,3-dihydro-1H-pyrrolo[3,2-c]-quinoline;
(25) 4-methyl-8-phenoxy-1-(1-phenylethyl)-2,3-dihydro-1H-pyrrolo[3,2-c]-quinoline;
(26) 8-methoxy-4-methyl-1-(2-phenylethyl)-2,3-dihydro-1H-pyrrolo[3,2-c]-quinoline;
(27) 6,8-dimethoxy-1-(4-hydroxyphenyl)-4-methyl-2,3-dihydro-1H-pyrrolo[3,2-c]quinoline;
(28) 6,8-dimethoxy-1-(3-hydroxyphenyl)-4-methyl-2,3-dihydro-1H-pyrrolo[3,2-c]quinoline;
(29) 6,8-dimethoxy-1-(3-hydroxy-5-methylphenyl)-4-methyl-2,3-dihydro-1H-pyrrolo[3,2-c]quinoline;
(30) 8-methoxy-1-(4-methoxyphenyl)-4-methyl-2,3-dihydro-1H-pyrrolo[3,2-c]-quinoline;
(31) 8-trifluoromethoxy-1-(4-phenoxyphenyl)-4-methyl-2,3-dihydro-1H-pyrrolo[3,2-c]-quinoline;
(32) 6,8-dimethoxy-4-methyl-1-[4-(pyridin-3-yloxy)phenyl]-2,3-dihydro-1H-pyrrolo[3,2-c]quinoline;
(33) 1-benzyl-6,8-dimethoxy-4-methyl-2,3-dihydro-1H-pyrrolo[3,2-c]quinoline;
(34) 6,8-dimethoxy-4-methyl-1-(2-phenylethyl)-2,3-dihydro-1H-pyrrolo[3,2-c]-quinoline;
(35) 4-methyl-1-(2-phenylethyl)-8-trifluoromethoxy-2,3-dihydro-1H-pyrrolo[3,2-c]-quinoline;
(36) 6,8-dimethoxy-1-(indan-1-yl)-4-methyl-2,3-dihydro-1H-pyrrolo[3,2-c]-quinoline;
(37) 6,8-dimethoxy-4-methyl-1-[(6-phenoxy)pyridin-3-yl]-2,3-dihydro-1H-pyrrolo[3,2-c]quinoline;
(38) 6,8-dimethoxy-1-[(6-methoxy)pyridin-3-yl]-4-methyl-2,3-dihydro-1H-pyrrolo[3,2-c]quinoline;
(39) 1-(benzodioxol-5-ylmethyl)-6,8-dimethoxy-4-methyl-2,3-dihydro-1H-pyrrolo[3,2-c]quinoline;
(40) 6,8-dimethoxy-4-methyl-1-(3-methylbutyl)-2,3-dihydro-1H-pyrrolo[3,2-c]-quinoline;
(41) 1-cyclopropylmethyl-6,8-dimethoxy-4-methyl-2,3-dihydro-1H-pyrrolo[3,2-c]quinoline;
(42) 4-methyl-8-(morpholin-4-yl)-1-(4-phenoxyphenyl)-2,3-dihydro-1H-pyrrolo[3,2-c]quinoline;
(43) 8-methoxy-4-methyl-1-(1,2,3,4-tetrahydronaphthalen-1-yl)-2,3-dihydro-1H-pyrrolo[3,2-c]quinoline;
(44) 4-methyl-1-(2-phenylethyl)-2,3-dihydro-1H-pyrrolo[3,2-c]quinoline;
(45) 4,6-dimethyl-1-(2-methylphenyl)-2,3-dihydro-1H-pyrrolo[3,2-c]quinoline;
(46) 4,6-dimethyl-1-(2-phenylethyl)-2,3-dihydro-1H-pyrrolo[3,2-c]quinoline;
(47) 4-methyl-8-(piperidin-1-yl)-1-[4-(piperidin-1-yl)phenyl]-2,3-dihydro-1H-pyrrolo[3,2-c]quinoline;
(48) 4-methyl-8-(piperidin-1-yl)-1-(3-phenoxyphenyl)-2,3-dihydro-1H-pyrrolo[3,2-c]quinoline;
(49) 1-{4-[2-(N,N-dimethylamino)ethoxy]phenyl}-4-methyl-8-phenoxy-2,3-dihydro-1H-pyrrolo[3,2-c]quinoline;
(50) 1-[4-(4-fluorophenoxy)phenyl]-8-methoxy-4-methyl-2,3-dihydro-1H-pyrrolo[3,2-c]quinoline;
(51) 1-(benzodioxan-2-ylmethyl)-8-methoxy-4-methyl-2,3-dihydro-1H-pyrrolo[3,2-c]quinoline;
(52) 1-cyclohexyl-8-methoxy-4-methyl-2,3-dihydro-1H-pyrrolo[3,2-c]quinoline;
(53) 8-methoxy-4-methyl-1-phenyl-2,3-dihydro-1H-pyrrolo[3,2-c]quinoline;
(54) 4-methyl-8-phenoxy-1-[4-(3-pyridyl)phenyl]-2,3-dihydro-1H-pyrrolo[3,2-c]-quinoline;
(55) 4-methyl-8-phenoxy-1-[2-(3-pyridyl)ethyl]-2,3-dihydro-1H-pyrrolo[3,2-c]-quinoline;
(56) 4-methyl-8-phenoxy-1-(2-pyridylmethyl)-2,3-dihydro-1H-pyrrolo[3,2-c]-quinoline;
(57) 4-methyl-1-(5-methylpyrazin-2-ylmethyl)-8-phenoxy-2,3-dihydro-1H-pyrrolo[3,2-c]quinoline;
(58) 8-chloro-4-methyl-1-(2-phenylethyl)-2,3-dihydro-1H-pyrrolo[3,2-c]-quinoline;
(59) methyl 4-methyl-1-(2-phenylethyl)-2,3-dihydro-1H-pyrrolo[3,2-c]quinoline-8-carboxylate;
(60) 4-methyl-8-(morpholin-1-yl)-1-(2-phenylethyl)-2,3-dihydro-1H-pyrrolo[3,2-c]quinoline;
(61) ethyl[4-methyl-1-(2-phenylethyl)-2,3-dihydro-1H-pyrrolo[3,2-c]quinoline-8-yl]acetate;
(62) 1-[3-(4-methyl-8-phenoxy-2,3-dihydro-1H-pyrrolo[3,2-c]quinolin-1-yl)propyl]-pyrrolidin-2-one;
(63) 4-methyl-8-phenoxy-1-[2-(2-pyridyl)ethyl]-2,3-dihydro-1H-pyrrolo[3,2-c]quinoline;
(64) ethyl 3-(8-methoxy-4-methyl-2,3-dihydro-1H-pyrrolo[3,2-c]quinoline-1-yl)propionate;
(65) ethyl 4-(4-methyl-8-phenoxy-2,3-dihydro-1H-pyrrolo[3,2-c]quinoline-1-yl)butanoate;
(66) methyl 4-(4-methyl-8-phenoxy-2,3-dihydro-1H-pyrrolo[3,2-c]quinoline-1-yl)butanoate;
(67) ethyl (4-methyl-8-phenoxy-2,3-dihydro-1H-pyrrolo[3,2-c]quinoline-1-yl)acetate;
(68) 4-methyl-1-(1-methylpiperidin-4-yl)-8-phenoxy-2,3-dihydro-1H-pyrrolo[3,2-c]quinoline;
(69) 1-(1-benzylpyrrolidin-3-yl)-8-methoxy-4-methyl-2,3-dihydro-1H-pyrrolo[3,2-c]quinoline;
(70) methyl 3-(4-methyl-8-phenoxy-2,3-dihydro-1H-pyrrolo[3,2-c]quinoline-1-yl)propionate;
(71) 1-((S)-indan-1-yl)-4-methyl-8-phenoxy-2,3-dihydro-1H-pyrrolo[3,2-c]-quinoline;
(72) 1-((R)-indan-1-yl)-4-methyl-8-phenoxy-2,3-dihydro-1H-pyrrolo[3,2-c]-quinoline;
(73) 1-(3-methoxypropyl)-4-methyl-8-phenoxy-2,3-dihydro-1H-pyrrolo[3,2-c]-quinoline;
(74) 4-methyl-8-phenoxy-1-(tetrahydrofuran-2-ylmethyl)-2,3-dihydro-1H-pyrrolo[3,2-c]quinoline;
(75) 1-[2-(4-chlorophenyl)ethyl]-4-methyl-8-phenoxy-2,3-dihydro-1H-pyrrolo[3,2-c]quinoline;
(76) 1-[2-(4-methoxyphenyl)ethyl]-4-methyl-8-phenoxy-2,3-dihydro-1H-pyrrolo[3,2-c]quinoline;
(77) 4-methyl-8-phenoxy-1-(2-phenylpropyl)-2,3-dihydro-1H-pyrrolo[3,2-c]-quinoline;
(78) 8-cyano-4-methyl-1-(2-phenylethyl)-2,3-dihydro-1H-pyrrolo[3,2-c]quinoline;
(79) 8-hydroxy-4-methyl-1-(2-phenylethyl)-2,3-dihydro-1H-pyrrolo[3,2-c]-quinoline;
(80) 8-phenoxy-1-(2-phenylethyl)-2,3-dihydro-1H-pyrrolo[3,2-c]quinoline;
(81) 6,8-dimethoxy-1-(4-hydroxyphenyl)-4-methylpyrrolo[3,2-c]quinoline;
(82) 8-methoxy-4-methyl-1-[4-(4-methylpiperazin-1-yl)-3-fluorophenyl]-2,3-dihydro-1H-pyrrolo[3,2-c]quinoline;
(83) 4-methyl-8-phenylamino-1-(2-phenylethyl)-2,3-dihydro-1H-pyrrolo[3,2-c]-quinoline;
(84) [4-methyl-1-(2-phenylethyl)-2,3-dihydro-1H-pyrrolo[2,3-c]quinoline-8-oyl]-piperidine, and pharmaceutically-acceptable salts and/or solvates thereof.

As well as having activity against fungi and bacteria, compounds of formulae Ib and Ic may also have activity against other organisms, such as protozoa. Therefore, according to further aspects of the invention, there is provided:

(i) the use of a compound of formula Ib or Ic, as hereinbefore defined, for the preparation of a medicament for the treatment of a protozoal disease;

(ii) a method of treating a protozoal disease in a mammal, the method comprising administering to said mammal an effective amount of a compound of formula Ib or Ic, as hereinbefore defined;

(iii) use (e.g. ex vivo use) of a compound of formula Ib or Ic for killing protozoa.

When used herein, the terms "protozoa" (and derivatives thereof, such as "protozoal disease") includes references to organisms (or infections due to organisms) of the following classes and specific types:

Leishmania (e.g. *Leishmania donovanii*);
Plasmodium spp.;
Trypanosoma spp.;
Giardia lamblia;
coccidia (e.g. *Cryptosporidium parvum*, *Isospora belli*);
Toxoplasma (e.g. *Toxoplasma gondii*);
Balantidium coli;
amoeba (e.g. *Entamoeba*, such as *Entamoeba histolytica*, *Entamoeba coli*, *Entamoeba hartmanni* and *Entamoeba polecki*); and
Microsporidia (e.g. *Enterocylozoon bieneusi*, *Encephalitozoon hellem*, *Encephalitozoon cuniculi* and *Septata intestinalis*).

Particular conditions that the compounds of formula Ib or Ic can be used to treat include Leishmaniasis, malaria, trypanosomiasis, toxoplasmosis, giardiasis, balantidiasis, amoebiasis (amoebic dysentery), cryptosporidiosis, isosporiasis and microsporidiosis.

In addition, compounds of formula I and Ia may be employed in the use or method at (i) and (ii) above when the protozoal disease is other than malaria or amoebiasis. Further, compounds of formula I and Ia may be employed in the use at (iii) above when the protozoa are other than *Plasmodium* spp. or amoeba.

Compounds of formula I (including compounds of formulae Ia, Ib and Ic) may be prepared in accordance with techniques known to those skilled in the art, for example as described hereinafter.

Thus, according to a further aspect of the invention there is provided a process for the preparation of a compound of formula I (e.g. a compound of formula Ic), which comprises:

(a) for compounds of formula I in which X represents $-C(R^{8a})(R^{8b})-C(R^{8c})(R^{8d})-$, reaction of a compound of formula II,

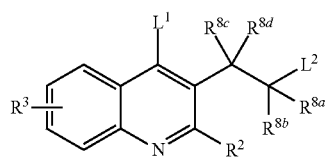

wherein $L^1$ and $L^2$ independently represent a suitable leaving group (e.g. halo) and $R^2$, $R^3$, $R^{8a}$, $R^{8b}$, $R^{8c}$ and $R^{8d}$ are as hereinbefore defined, with a compound of formula III,

wherein $R^1$ is as hereinbefore defined, for example under conditions known to those skilled in the art (e.g. by reaction at elevated temperature (such as 70 to 225° C.) and/or pressure (i.e. above 1 atmosphere) in the presence of a suitable organic solvent, such as a $C_{1-4}$ alcohol (e.g. ethanol or n-butanol) (for example, the reaction may be performed by reaction of the compound of formula II with between 1 and 3 equivalents (e.g. from 1.5 to 2 equivalents) of the compound of formula III at elevated temperature (e.g. above 120° C., such as from 150 to 200° C. or, particularly, from 175 to 185° C. (e.g. 180° C.)), wherein the reaction mixture is optionally heated by use of microwaves, in the presence of a suitable high-boiling solvent (e.g. an alkylene glycol, such as ethylene glycol) or, when the compound of formula III is liquid at the reaction temperature, in the presence of excess compound of formula III); or (b) for compounds of formula I in which X represents $-C(R^{8e})=C(R^{8f})-$, dehydrogenation of a corresponding compound of formula I in which X represents $-C(H)(R^{8a})-C(H)(R^{8c})-$, for example under conditions known to those skilled in the art (such as reaction at elevated temperature (e.g. from 70 to 225° C.) in the presence of a (de)hydrogenation catalyst (e.g. palladium supported on carbon) and a suitable, reaction-inert solvent (e.g. diphenylether)).

In the formation of compounds of formula I in which X represents $-C(R^{8a})(R^{8b})-C(R^{8c})(R^{8d})-$ (e.g. as outlined at (a) above), elimination of extraneous oxidants (e.g. atmospheric oxygen), may be utilised in order to minimise the formation of corresponding compounds of formula I in which X represents $-C(R^{8e})=C(R^{8f})-$. This may be effected, for example, by degassing reaction solvents and/or reagents, or by use of an antioxidant (e.g. at a low level, such as 0.5 mol. %) such as butylated hydroxytoluene ("BHT").

Compounds of formula II in which $L^1$ and $L^2$ both represent halo may be prepared according to methods known to those skilled in the art, for example by reaction of a corresponding compound of formula IV,

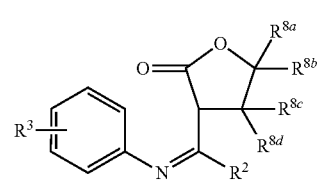

wherein $R^2$, $R^3$, $R^{8a}$, $R^{8b}$, $R^{8c}$ and $R^{8d}$ are as hereinbefore defined, with a combined dehydrating/halogenating agent (e.g. $P(O)Cl_3$), for example under conditions know to those skilled in the art (e.g. at elevated temperature, optionally in the presence of a suitable organic solvent). For example, the reaction may be performed by reaction at elevated temperature (e.g. from 75 to 120° C., such as from 90 to 100° C.) of the compound of formula IV with from 1 to 5 (e.g. 2) equivalents of $P(O)Cl_3$, optionally (and preferably) in the presence of a suitable solvent (e.g. acetonitrile or, particularly, toluene).

Compounds of formula IV may be prepared by reaction of a corresponding compound of formula V,

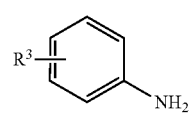

wherein $R^3$ is as hereinbefore defined, with a compound of formula VI,

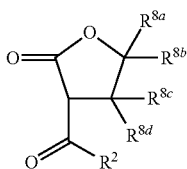

VI wherein $R^2$, $R^3$, $R^{8a}$, $R^{8b}$, $R^{8c}$ and $R^{8d}$ are as hereinbefore defined, for example under conditions know to those skilled in the art (e.g. at elevated temperature, such as from 100 to 180° C.). For example, the reaction may be performed by reaction at elevated temperature (e.g. from 75 to 120° C., such as from 100 to 118° C.) of the compound of formula V with from 1 to 1.5 equivalents (e.g. 1 or 1.1 equivalents) of the compound of formula VI in the presence of a suitable solvent (e.g. a high-boiling, water-immiscible hydrocarbon, such as toluene) and optionally in the presence of a suitable catalyst (e.g. an acid, such as acetic acid or, particularly, an acidic polymer resin (ion exchange resin), such as a polysulfonated polymer of styrene or copolymer of styrene and divinylbenzene (e.g. Amberlyst 15)). In this instance, the reaction may be performed in the presence of a dehydrating agent (such as molecular sieves) or in such a way that water generated by the condensation reaction is removed whilst the reaction is in progress (e.g. by use of a water-immiscible solvent such as toluene and a Dean-Stark apparatus, as known to those skilled in the art).

Compounds of formulae III, V and VI are either commercially available, are known in the literature, or may be obtained by analogy with the processes described herein, or by conventional synthetic procedures, in accordance with standard techniques, from readily available starting materials using appropriate reagents and reaction conditions.

Substituents on alkyl, alkenyl, alkynyl, cycloalkyl, cycloalkenyl, aryl and heterocyclic groups in compounds of formulae I, II, III, IV, V and VI may be introduced and/or interconverted using techniques well known to those skilled in the art by way of standard functional groups interconversions, in accordance with standard techniques, from readily available starting materials using appropriate reagents and reaction conditions. For example, hydroxy may be converted to alkoxy, phenyl may be halogenated to give halophenyl, halo may be displaced by cyano, etc.

Compounds of formula I may be isolated from their reaction mixtures using conventional techniques. For example, compounds of formula I may be isolated by conversion to an acid (e.g. hydrochloric acid) salt (e.g. by way of addition of acid to the crude product) and then recrystallisation of the salt from a suitable solvent (e.g. methanol or, particularly, ethanol). Alternatively, the salt can simply be washed with or slurried in the presence such a suitable solvent in order to isolate the pure acid salt of the compound of formula I.

In accordance with the present invention, pharmaceutically acceptable derivatives of compounds of formula I also include "protected" derivatives, and/or compounds that act as prodrugs, of compounds of formula I.

Compounds of formula I may exhibit tautomerism. All tautomeric forms and mixtures thereof are included within the scope of the invention.

Compounds of formula I may also contain one or more asymmetric carbon atoms and may therefore exhibit optical and/or diastereoisomerism. Diastereoisomers may be separated using conventional techniques, e.g. chromatography.

The various stereoisomers may be isolated by separation of a racemic or other mixture of the compounds using conventional, e.g. HPLC techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

It will be appreciated by those skilled in the art that in the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters.

The protection and deprotection of functional groups may take place before or after coupling, or before or after any other reaction in the above-mentioned schemes.

Protecting groups may be removed in accordance with techniques that are well known to those skilled in the art and as described hereinafter.

Persons skilled in the art will appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", 3$^{rd}$ edition, T. W. Greene & P. G. M. Wutz, Wiley-Interscience (1999).

Protected derivatives of compounds of formula I may be converted chemically to compounds of the invention using standard deprotection techniques (e.g. hydrogenation). The skilled person will also appreciate that certain compounds of formula I may also be referred to as being "protected derivatives" of other compounds of formula I.

Those skilled in the art will also appreciate that certain compounds of formula I will be useful as intermediates in the synthesis of certain other compounds of formula I.

When used in the above-described method of treatment, the compounds of formula Ib and Ic may be formulated for administration to a patient. In this respect, according to a still further aspect of the invention there is provided a pharmaceutical formulation including a compound of formula Ib or Ic, in admixture with a pharmaceutically acceptable adjuvant, diluent or carrier.

The above-mentioned medicaments, (components of) combination products and pharmaceutical formulations may be prepared according to methods known to those skilled in the art, for example by mixing the compounds of formulae I, Ia, Ib or Ic with excipient or excipients.

When formulated with excipients, the compounds of formulae I, Ia, Ib or Ic may be present in the above-mentioned medicaments, (components of) combination products and pharmaceutical formulations in a concentration from 0.1 to 99.5% (such as from 0.5 to 95%) by weight of the total mixture.

When administered to patients by way of any of the above-mentioned medicaments, (components of) combination products and pharmaceutical formulations, compounds of formulae I, Ia, Ib or Ic will normally be administered orally, by any parenteral route or via inhalation.

In the case of animals, compounds of formulae I, Ia, Ib or Ic can also be administered by incorporation of the compound of formulae I, Ia, Ib or Ic into feed or drinking water.

Preferred route of administration of compounds of the invention are oral.

Suitable daily doses of the compounds of the invention in prophylactic and/or therapeutic treatment of mammals (e.g. humans) include, for example, 0.001-100 mg/kg body weight at peroral administration and 0.001-50 mg/kg body weight at parenteral administration.

In a particular embodiment of the invention, compounds of formulae I, Ia, Ib or Ic are administered topically. Thus, according to the invention there is provided:
(I) a topical pharmaceutical composition comprising a compounds of formula I, Ia, Ib or Ic in admixture with a pharmaceutically acceptable adjuvant, diluent or carrier;
(II) a combination product for topical administration comprising
  (A) a compound of formula I, as hereinbefore defined, and
  (B) a conventional antibiotic agent, as hereinbefore defined,
  wherein each of components (A) and (B) is formulated in admixture with a pharmaceutically-acceptable adjuvant, diluent or carrier.

In relation to (II) above, the combination product provides for the administration of component (A) in conjunction with component (B), and may thus be presented either as separate topical formulations, wherein at least one of those formulations comprises component (A) and at least one comprises component (B), or may be presented (i.e. formulated) as a combined topical preparation (i.e. presented as a single topical formulation including component (A) and component (B)).

Topical compositions, which are useful for treating disorders of the skin or of membranes accessible by digitation (such as membrane of the mouth, vagina, cervix, anus and rectum), include creams, ointments, lotions, sprays, gels and sterile aqueous solutions or suspensions. As such, topical compositions include those in which the active ingredient(s) is (are) dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components selected from the following list:

a solubilising agent or solvent (e.g. a β-cyclodextrin, such as hydroxypropyl β-cyclodextrin, or an alcohol or polyol such as ethanol, propylene glycol or glycerol);
a thickening agent (e.g. hydroxyethylcellulose, hydroxypropylcellulose, carboxymethylcellulose or carbomer);
a gelling agent (e.g. a polyoxyethylene-polyoxypropylene copolymer);
a preservative (e.g. benzyl alcohol, benzalkonium chloride, chlorhexidine, chlorbutol, a benzoate, potassium sorbate or EDTA or salt thereof); and
pH buffering agent(s) (such as a mixture of dihydrogen phosphate and hydrogen phosphate salts, or a mixture of citric acid and a hydrogen phosphate salt).

The amount of compound of formulae I, Ia, Ib or Ic used in topical compositions or combination products will depend, inter alia, upon the particular nature of the composition or combination product, as well as its intended use. In any event, those skilled in the art will be able to determine, by routine and non-inventive methods, amounts of compound of formulae I, Ia, Ib or Ic that can be employed. Typically, however, the compound of formulae I, Ia, Ib or Ic will be present in the topical composition or combination product at from 0.01 to 25% by weight (e.g. from 0.1 to 10% by weight, such as from 0.1 to 5% by weight or, particularly, from 0.5 to 3% (e.g. 2%) by weight) of the composition or product.

Methods of producing topical pharmaceutical compositions such as creams, ointments, lotions, sprays and sterile aqueous solutions or suspensions are well known in the art. Suitable methods of preparing topical pharmaceutical compositions are described, for example in WO 95/10999, U.S. Pat. No. 6,974,585, WO 2006/048747, as well as in documents cited in any of these references.

Topical pharmaceutical compositions and combination products according to the present invention may be used to treat a variety of skin or membrane disorders, such as infections of the skin or membranes (e.g. e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria, fungi described hereinbefore, (e.g. any of the Staphylococci, Streptococci, Mycobacteria or *Pseudomonas* organisms mentioned hereinbefore, such as *S. aureus* (e.g. Methicillin resistant *S. aureus* (MRSA))).

Particular bacterial conditions that may be treated by topical pharmaceutical compositions and combination products according to the present invention also include the skin- and membrane-related conditions disclosed hereinbefore, as well as: acne vulgaris; rosacea (including erythematotelangiectatic rosacea, papulopustular rosacea, phymatous rosacea and ocular rosacea); erysipelas; erythrasma; eethyma; eethyma gangrenosum; impetigo; paronychia; cellulitis; folliculitis (including hot tub folliculitis); furunculosis; carbunculosis; staphylococcal scalded skin syndrome; surgical scarlet fever; streptococcal peri-anal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii*, *M. malmoense*, *M. szulgai*, *M. simiae*, *M. gordonae*, *M. haemophilum*, *M. avium*, *M. intracellulare*, *M. chelonae* (including *M. abscessus*) or *M. fortuitum* infections, swimming pool (or fish tank)

granuloma, lymphadenitis and Buruli ulcer (Bairnsdale ulcer, Searles' ulcer, Kakerifu ulcer or Toro ulcer)); as well as infected eczma, burns, abrasions and skin wounds.

Particular fungal conditions that may be treated by topical pharmaceutical compositions and combination products according to the present invention also include the skin- and membrane-related conditions disclosed hereinbefore, as well as: candidiasis; sporotrichosis; ringworm (e.g. tinea pedis, tinea cruris, tinea capitis, tinea unguium or tinea corporis); tinea versicolor; and infections with *Trichophyton*, *Microsporum*, *Epidermophyton* or *Pityrosporum ovale* fungi.

When employed to treat a microbial infection, the compounds of formulae I, Ia, Ib or Ic, whether administered on their own or in combination with a conventional antimicrobial agent, are preferably administered in a smaller number of doses than is necessary for the treatment of the same microbial infection utilising conventional antimicrobial agents only (e.g. in less than 7, 6, 5, 4, or 3 doses, such as in 2 doses or, particularly, 1 dose).

In this respect, a still further aspect of the invention provides a method of reducing the dose of conventional antimicrobial agent required to treat a microbial infection, the method comprising co-administering a compound of formula I, Ia, Ib or Ic.

Compounds of formulae I, Ia, Ib and Ic have the advantage that they may be used to kill clinically latent microorganisms. Further, in treating microbial infections, compounds of formulae I, Ia, Ib and Ic may possess the further advantage that they allow for a shorter period of therapy (either alone or in combination with a conventional antimicrobial agent), thus increasing patient compliance (through, for example, the need to take fewer or smaller doses of antimicrobial agents) and/or minimising the risk of generating sub-populations of microorganisms that are (genetically) resistant to conventional antimicrobial agents.

Additionally, compounds according to the invention may have the advantage that they may be more efficacious than, be less toxic than, have a broader range of activity than, be more potent than, produce fewer side effects than, or have other useful pharmacological properties over compounds known in the prior art.

Biological Tests

Test procedures that may be employed to determine the biological (e.g. bactericidal or antibacterial) activity of the compounds of formulae I, Ia, Ib and Ic include those known to persons skilled in the art for determining:
(a) bactericidal activity against stationary-phase or "persister" bacteria (i.e. "clinically latent" bacteria); and
(b) antibacterial activity against log phase bacteria.

In relation to (b) above, methods for determining activity against log phase bacteria include a determination, under standard conditions (i.e. conditions known to those skilled in the art, such as those descried in WO 2005/014585, the disclosures of which document are hereby incorporated by reference), of Minimum Inhibitory Concentration ("MIC") or Minimum Bactericidal Concentration ("MBC") for a test compound.

In relation to (a) above, methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound. Specific examples of such methods are described below.

Protocol for Pyogenic Bacteria
Bacterial Strains
The strains used for screening are shown in the following table.

| | | |
|---|---|---|
| *Staphylococcus aureus* (Oxford) | Gram positive | Reference strain |
| *Escherichia coli* K12 | Gram negative | Reference strain |
| *Enterococcus* | Gram positive | Clinical isolate |
| *Pseudomonas* | Gram negative | Clinical isolate |
| Methicillin resistant *S. aureus* (MRSA) | Gram positive | Clinical isolate |
| *Klebsiella aerogrenes* | Gram negative | Clinical isolate |
| *E. coli* | Gram negative | Clinical isolate |
| *Streptococcus pneumoniae* | Gram positive | Reference strain |
| *Streptococcus pyogenes* Group A *Streptococci* | Gram positive | Reference strain |
| Group B *streptococci* (*Streptococcus agalactiae*) | Gram positive | Reference strain |
| *Streptococcus viridans* | Gram positive | Reference strain |
| *Haemophilus influenzae* | Gram negative | Reference strain |

Growth of Bacteria

The bacteria (except for streptococci and *H. influenzae*) were grown in 10 mL of nutrient broth (No. 2 (Oxoid)) overnight at 37° C., with continuous shaking at 120 rpm. Streptococci and *H. influenzae* were grown overnight in Todd-Hewitt broth (Sigma) without shaking. The overnight cultures were diluted (1000×) in 100 mL of growth medium and then incubated with or without shaking for 10 days. Viability of the bacteria was estimated by colony forming unit (CFU) counts at 2 hours intervals at the first 24 hours and at 12-24 hours afterwards. From serial 10-fold dilutions of the experimental cultures, 100 µL samples were added to triplicate plates of nutrient agar plates (Oxoid) and blood agar plates (Oxoid). Colony forming units (CFU) were counted after incubation of the plates at 37° C. for 24 hours.

Log-Phase Cultures:

The above-described overnight cultures were diluted (1000×) with iso-sensitest broth. The cultures were then incubated at 37° C. with shaking for 1-2 hours to reach log CFU 6, which served as log-phase cultures.

Stationary Phase Cultures:

Cultures incubated for more than 24 hours are in stationary phase. For drug screening, 5-6 day old stationary phase cultures are used as shown in FIG. 1 (the periods between two arrows).

Measurements of Bactericidal Activity Against Log-Phase Cultures

Different concentrations of each test compound were incubated with the log-phase cultures in 96 well plates for various periods of time (2, 4, 6, 12, 24 hours). Bactericidal activity was then examined by taking a spectrophotometer reading (using a plate reader) of the resulting cultures, as well as by CFU counts as described above.

Measurements of Bactericidal Activity Against Stationary-Phase Cultures

Different concentrations of each test compound were incubated with stationary phase cultures (5-6 day cultures) in 96 well plates for 24 or 48 hours. Bactericidal activity was then determined by taking CFU counts of the resulting cultures, as described above.

Measurements of Bactericidal Activity Against Persistent Bacteria

An antibiotic (e.g. gentamicin) was added to 5-6 day stationary-phase cultures to the final concentration of 50 to 100 µg/mL for 24 hours. After 24 hours of antibiotic treatment, the cells are washed 3 times with phosphate buffered saline (PBS), and then resuspended in PBS. The surviving bacterial cells are used as persisters. Viability is estimated by CFU counts. The persisters were then used in measurements of bactericidal activity for test compounds.

Different concentrations of each test compound were incubated with the (persister) cell suspension in 96 well plates for various periods of time (24 and 48 hours). Bactericidal activity was then determined by taking CFU counts of the resulting cultures, as described above.

Protocol for *M. tuberculosis*

Growth of *M. tuberculosis*

*M. tuberculosis* H37Rv was grown in 10 mL of Middlebrook 7H9 broth containing 0.05% Tween 80 supplemented with 10% ADC without disturbing for up to 100 days. In order to obtain evenly dispersed cultures prior to experimental treatment, clumps in the cultures were broken up by vortexing the cultures in the presence of 2 mm glass beads (Philip Harris Scientific, Staffordshire, UK) for 2 minutes, followed by sonication in a water bath sonicator (Branson Ultrasonic B. V.) for 5 minutes. The numbers of viable *M. tuberculosis* in the cultures were determined by colony forming unit (CFU) counts on Middlebrook 7H11 agar. Serials of 10-fold dilutions of the cultures are made in Middlebrook 7H9 broth with 0.05% (v/v) Tween 80 but without ADC. Then, 100 μL of samples was added to one-third segments of the agar plates in duplicate. The plates were incubated in polyethene bags for 3 weeks at 37° C.

Measurements of Bactericidal Activity Against Log-Phase Cultures

Different concentrations of each test compound were incubated with log-phase cultures (4 day cultures) for various time periods (4, 8, 16, 24 days). Bactericidal activity was then determined by taking CFU counts of the resulting cultures, as described above.

Measurements of Bactericidal Activity Against Stationary-Phase Cultures and Persistent Bacteria Model 1—Stationary-Phase Cultures.

Different concentrations of each test compound were incubated with the sonicated 100-day cultures, each concentration to a separate 10 mL culture. After incubation for 5 days, counts of viable CFU were determined by inoculating a pair of 7H11 plates with 100 μL it of 10-fold serial dilutions of the resulting cultures.

Model 2—Persistent Bacteria Selected by Rifampicin.

Rifampicin (100 mg/L) was added to each of a set of sonicated 100-day cultures, which cultures were then incubated for 5 days. After the first day of incubation, no colonies could be obtained on plates inoculated from the culture. After washing twice with PBS by centrifugation, fresh (and rifampicin-free) 7H9 medium was added to make up the volume to 10 mL and the test compound was added in the same concentrations as in model 1. After further incubation for 7 days, CFU counts were determined by inoculating 1 mL from each container onto a 7H11 plate. These plates were then incubated for 2 weeks and the very small colonies were counted and marked. After a further 2 weeks of incubation, any additional unmarked colonies (i.e. those that grew slowly) were added to the counts. Control studies have shown that plate counts begin to yield colonies on subculture after about 4 days of incubation of the rifampicin-free cultures.

Model 3.

The procedure is similar to model 2, but only different concentrations of the test compound was added to the 100-day culture at three days after the rifampicin treatment. At the end of the 7-day incubation period (4 days with candidate drugs plus rifampicin), all cultures were washed, replacing with medium free of test compound, and then were incubated for a further 7 days before CFU counts were determined.

Skin (Topical) Models

In addition to in vitro testing against stationary- and log-phase bacteria, compounds of formulae I, Ia, Ib and Ic may also be tested in various in vivo models, including those known to those skilled in the art. For example, for determination of compound activity against bacteria in or on the skin, protocols that may be followed include those described in *Antimicrobial Agents and Chemotherapy* 49(8), 3435-41 (2005), as well as the following.

Mouse Superficial Skin Bacterial Model (Intact Skin)

ICR or BALB/c mice aged 6-8 weeks are obtained from Harlan UK. The mice are anesthetized by intraperitoneal injection of 200 μL, of Ketamine hydrochloride/Xylazine solution. Fur on the back of the mouse is removed using an electrical clipper. A 2 $cm^2$ (2 cm×1 cm) area of skin is marked with a marker pen. The marked skin area is swabbed using a disposable swab for 3 times in order to examine the bacterial numbers on the skin. The bacteria on the swab will spread on blood agar plates (Oxoid™).

Log-phase or stationary phase bacterial cultures will be used. The cultures will be concentrated by centrifugation to obtain $10^9$ to $10^{10}$ CFU/mL. The cell pellet will be resuspended with nutrient broth or PBS and glycerol (50%). 15-20 μL, of the cell suspension is added to the skin area (2 $cm^2$) which gives $10^{6-7}$ CFU on the skin. The skin is allowed to dry for about 15 min. Solutions of test compound at different concentrations will be applied on the skin area for different periods of time.

Bacterial numbers on the skin will be estimated as follows: After the mouse has been euthanised, the skin at the marked area will be cut and added into a 2 mL tube containing 1 mL water and glass beads (1 mm). The skin will be homogenised using a reciprocal shaker (Hybaid Ltd, UK) for 45 seconds (speed setting 6.5) or votexing for 1 min. Residual test compound will be removed by washing 3 times with water or PBS (if the test compound precipitates in the buffer system, water alone is used for washing). CFU counts will be performed after a serial of 10 fold dilution of the homogenates. 100 μL samples will be added to one third of blood agar plates (Oxoid™) in duplicate. Colony forming units (CFU) will then be counted using aCoLye (a colony counter) after incubation of the plates at 37° C. for 24 hours.

Mouse Superficial Skin Infection Model (Tape-Stripping Infection Model)

ICR or BALB/c mice aged 6-8 weeks are obtained from Harlan UK. The mice are anesthetized by intraperitoneal injection of 200 μL of Ketamine hydrochloride/Xylazine solution. The fur of the mice on the back will be removed by electric clipper. An area of 2 $cm^2$ skin is tape-stripped using autoclave tape. The skin will be striped 10 times in succession. After this procedure, the skin become visibly damaged and is characterized by reddening and glistening but no regular bleeding. Buprenorphine will be given during the anaesthetic period and every 12 hours for up to 3 days to reduce prolonged pain. After stripping of the skin, a bacterial infection is initiated by placing a 10 μL of bacterial cell suspension containing $10^7$ cells from overnight or stationary phase cultures on the damaged skin area. At 0 and 4 hours after infection, 3 mice will be killed to estimate the CFU counts on the skin. After 24 hours, solutions of test compound at different concentrations will be applied on the skin area for different periods of time. The experiments will be terminated 18 h after the last topical treatment.

Bacterial numbers of the wounds will be estimated as follow: After the mouse has been euthanised, the wounds, approximately 2 cm² will be cut and added to a 2 mL tube containing 1 mL water and glass beads (1 mm). The skin will be homogenised using a reciprocal shaker (Hybaid Ltd, UK) for 45 seconds (speed setting 6.5). Residual test compound will be removed by washing 3 times with water. CFU counts will be performed after a serial of 10 fold dilution of the homogenises. 100 µL samples are added to one third of blood agar plates (Oxoid™) in duplicate. Colony forming units (CFU) are counted using aCoLye (a colony counter) after incubation of the plates at 37° C. for 24 hours.

The invention is illustrated, but in no way limited, by the following examples and by reference to the figures, which present data relating, inter alia, to the biological studies described above.

Figure 1:
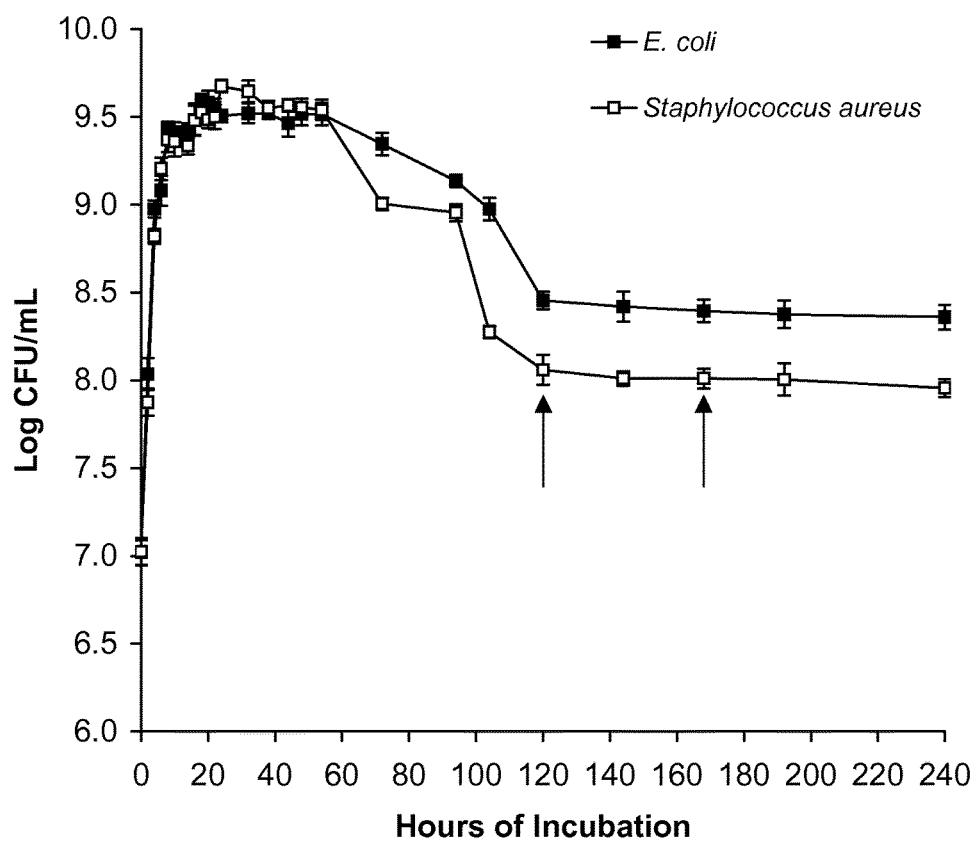
FIG. 1 illustrates typical growth curves for *S. aureus* and *E. coli*.
Figure 2:
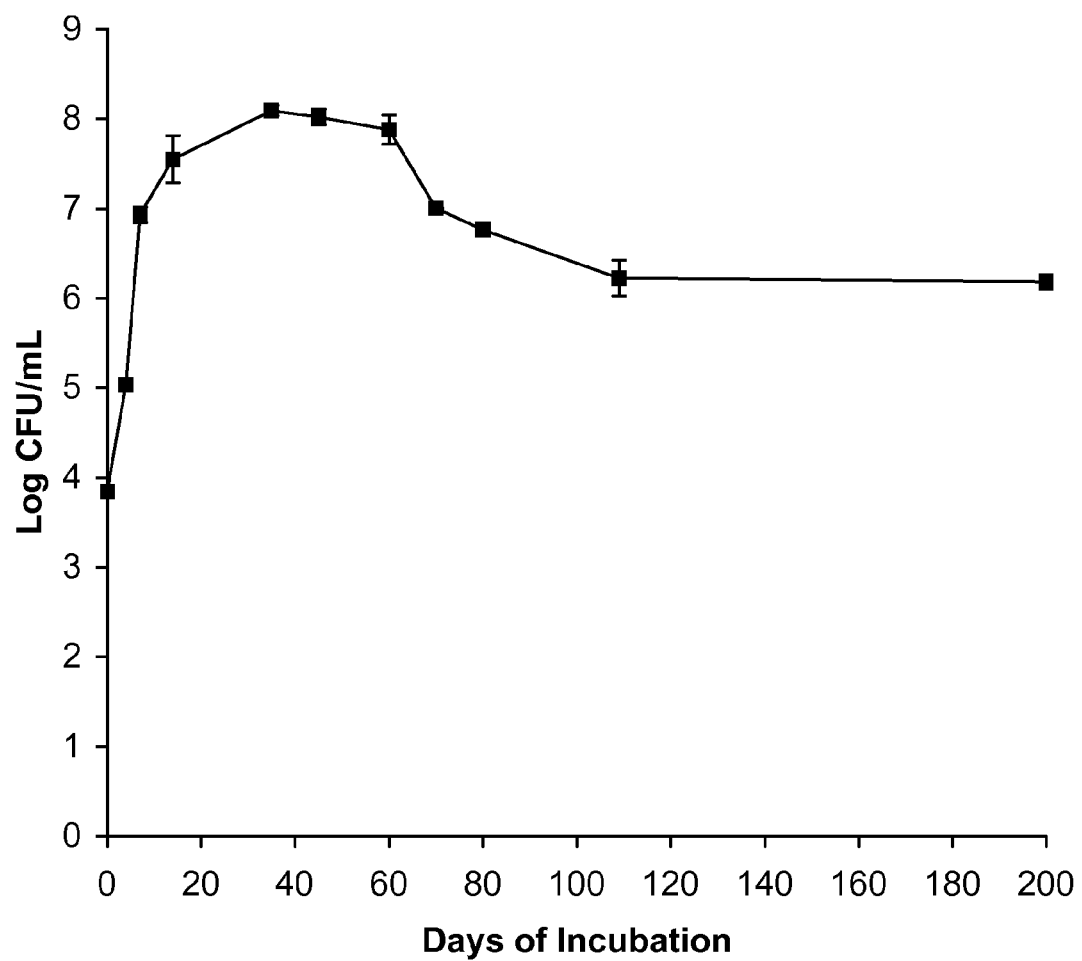
FIG. 2 illustrates a typical growth curve for *M. tuberculosis* H37R$^v$.
Figure 3:
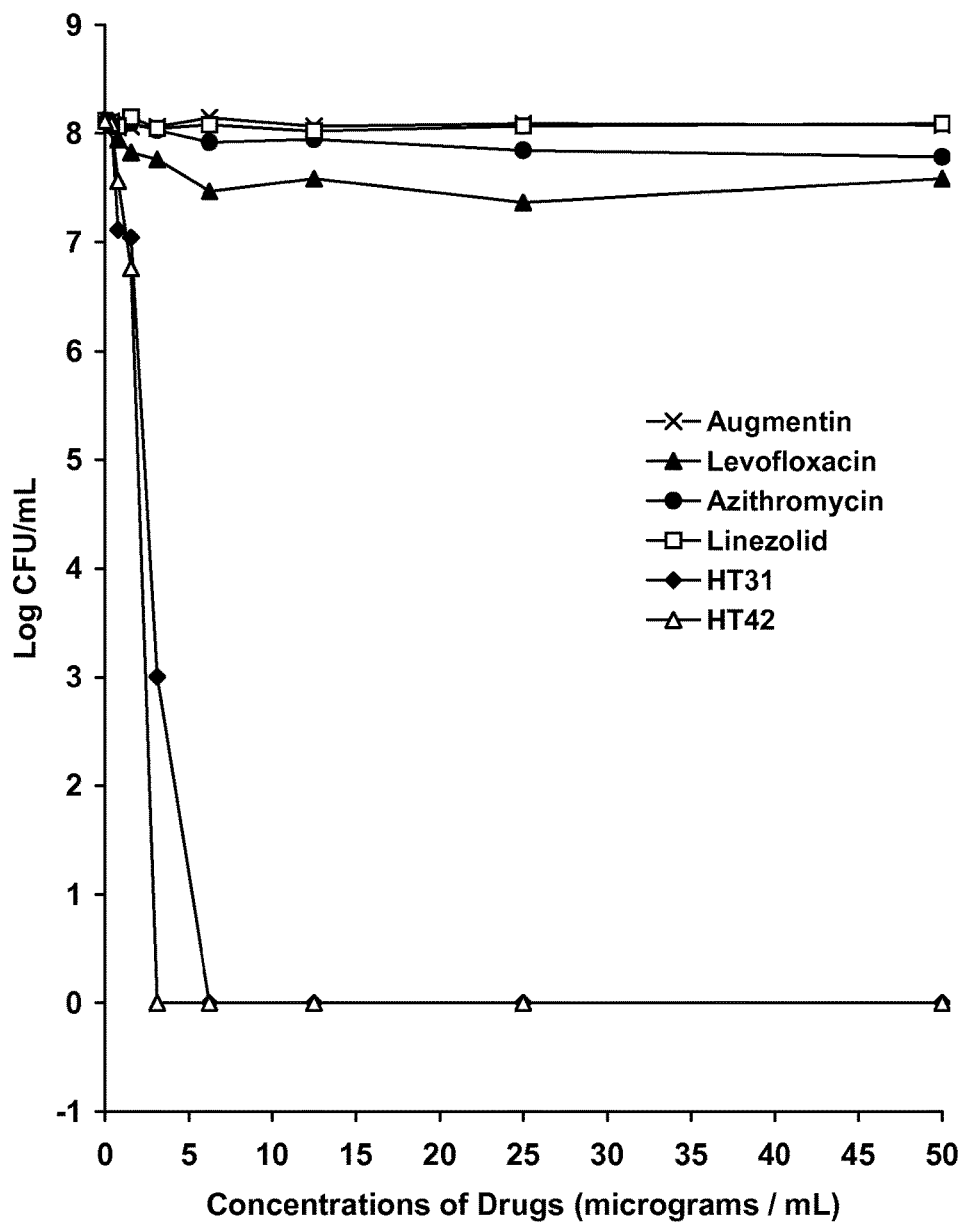

FIG. 3 illustrates the effects of various known antibiotics (Augmentin™, levofloxacin, azithromycin and linezolid), and of certain compounds of the present invention, against stationary phase *Staphylococcus aureus*. The bacterium was grown in nutrient broth medium with shaking for 5 days. The drugs were incubated with the bacterium for 24 hours. CFU counts were then performed on the drug treated cells and the control (drug free) cells.

Figure 4:
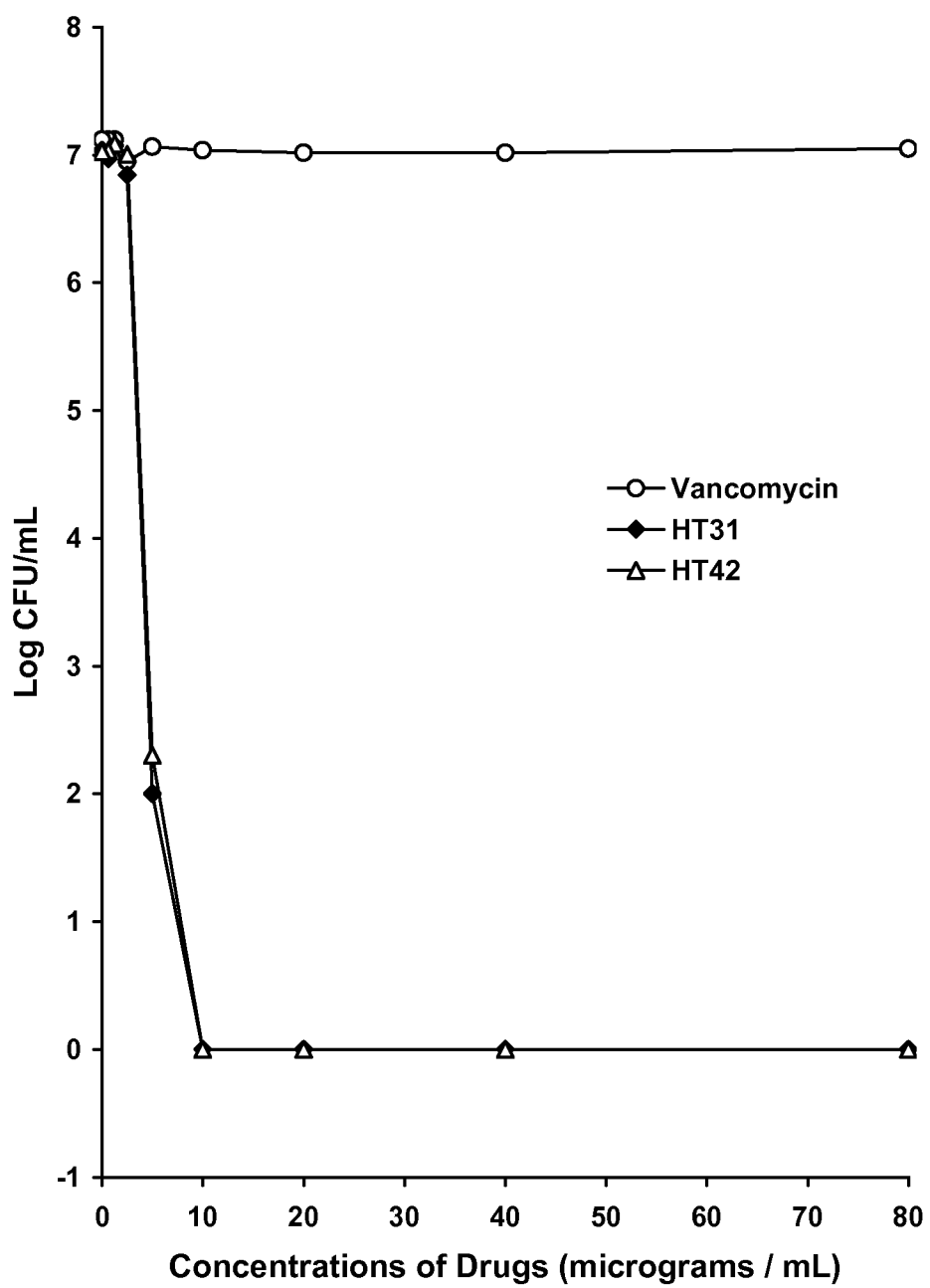

FIG. 4 illustrates the effects of vancomycin and certain compounds of the present invention against stationary phase stationary phase Methicillin Resistant *Staphylococcus aureus* (MRSA). The bacterium was grown in nutrient broth medium with shaking for 5 days. The drugs were incubated with the bacterium for 24 hours. CFU counts were performed on the drug treated cells and the control (drug free) cells.

KEY (FIGS. 3 AND 4)

HT31:
1-(Indan-2-yl)-4-methyl-8-phenoxy-2,3-dihydro-1H-pyrrolo[3,2-c]quinoline.
HT42:
4-Methyl-2-phenylethyl-8-phenoxy-2,3-dihydro-1H-pyrrolo[3,2-d]quinoline.

EXAMPLES

General Experimental Procedure

Analytical LC-MS data were obtained using either Method A or Method B as indicated.

Method A: A Hewlett Packard HP1100 LC system using a 30×4.6 mm 3 micron Phenomenex Luna C18 column eluting at 2 mL/min with a gradient (5-95% over 4 minutes) of MeCN/water (+0.1% formic acid). Detection by mass spectrometry used a Micromass Platform LC quadrupole instrument in both positive and negative electrospray mode. Detection was also performed using a Sedex 65 evaporative light scattering detector and an HP1100 Diode array detector.

Method B: A Hewlett Packard 1050 LC system using a 100×3 mm 5 micron Higgins Clipeus C18 column eluting at 2 mL/min with a gradient (5 to 95% over 15 minutes) of MeCN/water (+0.1% formic acid). Detection by mass spectrometry used a Finnigan TSQ700 triple quadrupole instrument in positive electrospray mode. Detection was also performed by UV absorption at 254 nm.

Starting Materials

The following, commercially available compounds may be employed in the syntheses described below.

| List 1 | |
|---|---|
| 2,4-Dimethoxyaniline. | 4-Chloroaniline. |
| 4-Methoxyaniline. | 4-(Morpholin-4-yl)aniline. |
| 4-Phenoxyaniline. | Ethyl 4-aminophenylacetate. |
| 2-Phenoxyaniline. | Methyl 4-aminobenzoate. |
| 4-Ethoxyaniline. | 4-Cyanoaniline. |
| 4-Trifluoromethoxyaniline. | 4-Hydroxyaniline. |
| 4-(Piperidin-1-yl)aniline. | |

| List 2 | |
|---|---|
| Cyclopropylamine. | Aniline. |
| 3-Phenoxyaniline. | 4-Phenoxyaniline. |
| 4-(2-Dimethylaminoethoxy)aniline. | 4-(Pyridin-3-yloxy)aniline. |
| 1-Benzyl-piperidin-4-ylamine. | Indan-2-ylamine. |
| Benzylamine. | 2-Phenylethylamine. |
| 2-Phenoxyethylamine. | 4-Hydroxyaniline. |
| 4-Methoxyaniline. | 3-Hydroxyaniline. |
| 3-Hydroxy-5-methylaniline. | 5-Amino-2-phenoxypyridine. |
| Indan-1-ylamine. | 3,4-Methylenedioxaniline. |
| 3-Methylbutylamine. | 5-Amino-2-methoxypyridine. |
| 4-iso-Propylaniline. | Cyclopropylmethylamine. |
| 4-Bromo-3-fluoroaniline. | Benzodioxan-2-ylmethylamine. |
| 1-Amino-1,2,3,4-tetrahydronaphthalene. | Cyclohexylamine. |
| | 2-Methylbenzylamine. |
| 1-Phenylethylamine. | 4-(4-Fluorophenoxy)aniline. |
| 4-(Piperidin-1-yl)aniline. | 2-Pyridylmethylamine. |
| 2-(3-Pyridyl)ethylamine. | 1-(3-Aminopropyl)pyrrolidin-2-one. |
| (5-Methylpyrazin-2-yl)methylamine. | |
| 2-(2-Pyridyl)ethylamine. | Ethyl 3-aminopropionate |
| Ethyl 4-aminobutanoate. | Methyl 3-aminopropionate. |
| Methyl 4-aminobutanoate. | Ethyl aminoacetate. |
| 4-Amino-1-methylpiperidine. | 1-Benzyl-3-aminopyrrolidine. |
| 3-Methoxypropylamine. | Tetrahydrofuran-2-ylmethylamine. |
| 2-(4-Chlorophenyl)ethylamine. | 2-(4-Methoxyphenyl)ethylamine. |
| 2-Phenylpropylamine. | |

PREPARATIONS

Preparation 1

The compounds listed below were prepared by the following general method.

The relevant aniline (0.05 mol; see List 1) and 2-acetyl-5-butyrolactone (0.05 mol) were heated to 120° C. for one hour, and then heated to 160° C. for two hours. After cooling to room temperature, phosphoryl chloride (50 mL) was added and the mixture heated at reflux for one hour. After cooling to room temperature again, the mixture was poured onto crushed ice (100 g) and neutralised with sodium carbonate (added as a solid). The resulting oily product was extracted into dichloromethane (50 mL) and the organic solution washed with water (25 mL), then brine (25 mL) and dried with anhydrous magnesium sulphate. Filtration and evaporation gave a brown solid, recrystallisation of which from ethanol gave the target substituted 4-chloro-3-(2-chloroethyl)-2-methylquinoline as a colourless or off-white solid.

(a) 4-Chloro-3-(2-chloroethyl)-6,8-dimethoxy-2-methylquinoline

LCMS (Method A): Rt=3.17 min, m/z=300.06 [M+H]$^+$; $C_{14}H_{15}Cl_2NO_2$, Mono-isotopic mass=299.1.

(b) 4-Chloro-3-(2-chloroethyl)-6-methoxy-2-methylquinoline

LCMS (Method A): Rt=3.16 min, m/z=269.98 [M+H]$^+$; C$_{13}$H$_{13}$Cl$_2$NO, Mono-isotopic mass=269.0.

(c) 4-Chloro-3-(2-chloroethyl)-2-methyl-6-phenoxyquinoline

LCMS (Method A): Rt=4.38 min, m/z=332.00 [M+H]$^+$; C$_{18}$H$_{15}$Cl$_2$NO, Mono-isotopic mass=331.05.

(d) 4-Chloro-3-(2-chloroethyl)-2-methyl-8-phenoxyquinoline

LCMS (Method A): Rt=4.27 min, m/z=332.01 [M+H]$^+$; C$_{18}$H$_{15}$Cl$_2$NO, Mono-isotopic mass=331.05.

(e) 4-Chloro-3-(2-chloroethyl)-6-ethoxy-2-methylquinoline

LCMS (Method A): Rt=3.54 min, m/z=284.16 [M+H]$^+$; C$_{14}$H$_{15}$Cl$_2$NO, Mono-isotopic mass=283.05.

(f) 4-Chloro-3-(2-chloroethyl)-2-methyl-6-(morpholin-4-yl)quinoline $^1$H NMR (400 Mz, D$_6$DMSO) δ 7.82 (d, J=9.3 Hz, 1H), 7.65 (dd, J=9.3, 2.7 Hz 1H), 7.23 (d, J=2.7 Hz, 1H), 3.88 (t, J=6.7 Hz, 2H), 3.79 (m, 4H), 3.41 (t, J=6.7 Hz, 2H), 3.28 (m, 4H), 2.70 (s, 3H).

(g) 4-Chloro-3-(2-chloroethyl)-2-methyl-6-trifluoromethoxyquinoline

LCMS (method A): Rt=4.39 min, m/z=323.89 [M+H]$^+$; C$_{13}$H$_{10}$Cl$_2$F$_3$NO, Mono-isotopic mass=323.01.

(h) 4-Chloro-3-(2-chloroethyl)-2-methylquinoline

LCMS (method A): Rt=3.14 min, m/z=240.13 [M+H]$^+$; C$_{12}$H$_{11}$Cl$_2$N, Mono-isotopic mass=239.03.

(i) 4-Chloro-3-(2-chloroethyl)-2,8-dimethylquinoline

LCMS (method A): Rt=4.53 min, m/z=253.98 [M+H]$^+$; C$_{13}$H$_{13}$Cl$_2$N, Mono-isotopic mass=253.04.

(j) 4-Chloro-3-(2-chloroethyl)-2-methyl-6-(piperidin-1-yl)quinoline

Used directly without purification.

(k) 3-(2-Chloroethyl)-4,6-dichloro-2-methylquinoline $^1$H NMR (400 Mz, D$_6$DMSO) δ 8.13 (d, J=2.2 Hz, 1H), 8.00 (d, J=9.0 Hz, 1H), 7.82 (dd, J=9.0 Hz, 2.2 Hz, 1H), 3.92 (t, J=7.6 Hz, 2H), 3.45 (t, J=7.6 Hz, 2H), 2.78 (s, 3H).

(l) Methyl 4-chloro-3-(2-chloroethyl)-2-methylquinolin-6-carboxylate

LCMS (method A): Rt=3.80 min, m/z=298.05 [M+H]$^+$; C$_{14}$H$_{13}$Cl$_2$NO$_2$, Mono-isotopic mass=297.03.

(m) Ethyl 4-chloro-3-(2-chloroethyl)-2-methylquinolin-6-ylacetate

LCMS (method A): Rt=3.47 min, m/z=326.13 [M+H]$^+$; C$_{16}$H$_{17}$Cl$_2$NO$_2$, Mono-isotopic mass=325.06.

(n) 4-Chloro-3-(2-chloroethyl)-6-cyano-2-methylquinoline

LCMS (method A): Rt=3.69 min, m/z=264.95 [M+H]$^+$; C$_{13}$H$_{10}$Cl$_2$N$_2$, Mono-isotopic mass=264.02.

(o) 4-Chloro-3-(2-chloroethyl)-6-hydroxy-2-methylquinoline

Used directly without purification.

(p) 6-Bromo-4-chloro-3-(2-chloroethyl)-2-methylquinoline $^1$H NMR (400 Mz, CDCl$_3$) δ 8.98 (d, J=9.1 Hz, 1H), 8.54 (d, J=2.4 Hz, 1H), 8.07 (dd, J=9.1, 2.4 Hz, 1H), 3.92 (t, J=6.1 Hz, 2H), 3.59 (t, J=6.1 Hz, 2H), 3.31 (s, 3H).

Preparation 2

4-Chloro-3-(2-chloroethyl)-6-phenoxyquinoline (i) Sodium (2-oxodihydrofuran-3-ylidene)methoxide A solution of ethyl formate (4.51 g) and γ-butyrolactone (5.0 g) in diethyl ether (50 mL) was added dropwise to a suspension of sodium hydride (60% oil dispersion, 2.56 g) in diethyl ether (100 mL) containing methanol (0.2 mL) at such a rate as to maintain gentle reflux. The resultant mixture was then stirred at room temperature for 48 hours. The mixture was evaporated to dryness and the residue was triturated with cyclohexane and the solid was collected by filtration to give the sub-title compound (7.46 g) as a white powder.

$^1$H NMR (400 Mz, D$_2$O) δ 8.35 (m, 1H), 4.25 (m, 2H), 2.70 (m, 2H).

(ii) 3-[1-(4-Phenoxyphenylamino)methylidene]dihydrofuran-2-one

A mixture of sodium (2-oxodihydrofuran-3-ylidene)methoxide (1.0 g; see step (i) above) and 4-phenoxyaniline hydrochloride (1.62 g) in methanol (20 mL) was stirred and heated at reflux for 30 minutes. The resultant cooled mixture was poured into water and the solid was collected by filtration and washed with water and ethyl acetate. The resultant solid was purified by chromatography on silica eluting with a mixture of methanol and dichloromethane (0:100 increasing to 1:20) to give the sub-title compound (0.69 g) as a white solid.

$^1$H NMR (400 Mz, D$_6$-DMSO) δ 9.06 (d, J=13.7 Hz, 1H), 7.62 (dt, J=13.4, 2.1 Hz, 1H), 7.36 (m, 2H), 7.19 (d, J=8.7 Hz, 2H), 7.09 (m, 1H), 6.96 (m, 4H), 4.29 (t, J=7.6, 2H), 2.86 (td, J=7.6, 2.1 Hz, 2H).

(iii) 4-Chloro-3-(2-chloroethyl)-6-phenoxyquinoline

A mixture of 3-[1-(4-phenoxyphenylamino)methylidene]dihydrofuran-2-one (0.2 g; see step (ii) above) and phosphorus oxychloride was stirred and heated at reflux for 30 minutes. The resultant cooled mixture was added carefully to water with ice cooling as required and extracted with diethyl ether. The organic phase was washed with aqueous brine solution, dried (MgSO$_4$) and filtered. The filtrate was evaporated to dryness and the residue was purified by chromatography eluting with a mixture of ethyl acetate and cyclohexane (1:3) to give the title compound (0.116 g) as a pale yellow oil.

$^1$H NMR (400 Mz, CDCl$_3$) δ 8.69 (s, 1H), 8.09 (d, J=9.2 Hz, 1H), 7.67 (d, J=2.6 Hz, 1H), 7.49 (dd, J=9.2, 2.6 Hz, 1H), 7.41 (m, 2H), 7.21 (m, 1H), 7.11 (m, 2H), 3.83 (t, J=7.1, 2H), 3.40 (t, J=7.1 Hz, 2H).

Preparation 3

3-[1-(4-Phenoxyphenylamino)ethylidene]dihydrofuran-2-one

Large Scale Process Outline.

| Step No. | Operation | Charges |
|---|---|---|
| 1 | Set-up 10 L flange flask equipped with Dean-Stark separator (250 mL volume). | |
| 2 | Charge to flask 4-phenoxyaniline (1 eq). | 1100 g |
| 3 | Charge to flask 2-acetylbutyrolactone (1.1 eq). | 703 mL |
| 4 | Charge to flask Amberlyst 15 ion exchange resin. | 110 g |
| 5 | Charge to flask toluene (3 volumes) and agitate. | 3300 mL |
| 6 | Heat reaction vessel to reflux. (Reflux temperature initially ~100° C. and as water is removed reflux temperature will increase to ~118° C.) | |
| 7 | The reaction was stirred at reflux overnight. (When ~200 mL of water has collected in Dean-Stark trap remove sample concentrate in vacuo and analyse using $^1$H NMR) | |
| 8 | Reaction allowed to cool to 50° C. | |
| 9 | The reaction mixture was filtered to remove the resin. Some precipitation of the product will occur in the Büchner flask. Addition of DCM will dissolve the material. Combine DCM mixture with toluene filtrate for concentration. | |
| 10 | Concentrate the reaction mixture in vacuo. Divide the reaction mixture between several RB flasks. | |
| 11 | Dry the crude solid in a vacuum oven overnight at 50° C. | |
| 12 | The crude solid was recrystallised from absolute EtOH (8 volumes). (Dissolved at 65-70° C. and on cooling precipitated at ~50° C.) | 8800 mL |

Preparation 4

4-Chloro-3-(2-chloroethyl)-2-methyl-6-phenoxyquinoline

Large Scale Process Outline.

| Step No. | Operation | Charges |
|---|---|---|
| 1 | Set-up 10 L flange flask equipped with HCl scrubber. | |
| 2 | Charge to flask 3-[1-(4-phenoxyphenylamino)-ethylidene]dihydrofuran-2-one (1 eq.; see Preparation 3 above). | 709 g |
| 3 | Charge to flask toluene (5 volumes). | 3550 mL |
| 4 | Charge to flask phosphorus oxychloride (2 eq). | 448 mL |
| 5 | The reaction flask was heated to 70° C. and then gradually to 90° C. at which point a slow exotherm increased the reaction temperature to reflux. | |
| 6 | The reaction temperature was maintained at 100° C. for 2 h, monitored for completion using LC analysis. Reaction deemed complete when <1% of 3-[1-(4-phenoxy-phenylamino)ethylidene]dihydrofuran-2-one present. Longer stir out if >1%. NB Gas evolution observed at this stage. | |
| 7 | The reaction was allowed to cool to 50° C. and added water dropwise initially (5 volumes). Reaction will exotherm and can be controlled by addition of water. NB Gas evolution observed at this stage. | 3550 mL |
| 8 | The reaction mixture was neutralised by addition of potassium carbonate. | ~1150 g |
| 9 | The reaction mixture was filtered to remove inorganic solids. | |
| 10 | The toluene layer was separated, dried over MgSO$_4$ and concentrated in vacuo to yield the crude product. NB Concentrate in batches of 1 L and remove solid from the flask before concentrating any further toluene. | |
| 11 | Dry the crude solid in a vacuum oven overnight at 50° C. | |
| 12 | Grind the crude solid into a powder using a pestle and mortar. | |
| 13 | The crude solid was slurried in MeOH (5 volumes) for 2 h at reflux, allowed to cool to room temperature and filtered to give the title compound, which was dried in a vacuum oven at 50° C. to constant weight. | 3550 mL |

Synthesis of Compounds of Formula I

Example 1

The compounds listed below were prepared by any one of the following three general methods. The crude compounds were then purified by any one of the purification methods described below.

General Method 1

The relevant substituted 4-chloro-3-(2-chloroethyl)-2-methylquinoline (0.5 mmol; see Preparation 1 above) and the desired primary amine or aniline (1.0 mmol; see List 2 above) were heated at reflux in butanol for 48 hours. The solvent was then evaporated prior to purification of the residue.

General Method 2

The relevant substituted 4-chloro-3-(2-chloroethyl)-2-methylquinoline (0.2 mmol; see Preparation 1 above) and the desired primary amine or aniline (0.4 mmol; see List 2 above) were dissolved in ethanol or n-butanol and heated to 170° C. in a sealed tube for up to 48 hours. The solvent was then evaporated prior to purification of the residue.

General Method 3

The relevant substituted 4-chloro-3-(2-chloroethyl)-2-methylquinoline (0.55 mmol; see Preparation 1 above), and the desired primary amine or aniline (0.55 mmol; see List 2 above) were dissolved in n-butanol or ethoxyethanol and heated to 220° C., using microwave irradiation, for 20 min. The solvent was then evaporated prior to purification of the residue.

Purification Method 1

The crude substituted 4-methyl-2,3-dihydro-1H-pyrrolo[3,2-c]quinoline (obtained by any one of the three general methods described above) was purified by preparative HPLC using a 150×20.6 mm 7 micron Genesis C18 column eluting at 10 mL/min with a gradient of water/MeCN (+0.1% trifluoroacetic acid or 0.1% formic acid). The fractions containing the desired product were concentrated in vacuo to give the desired product as a trifluoroacetate or formate salt.

Purification Method 2

The crude substituted 4-methyl-2,3-dihydro-1H-pyrrolo[3,2-c]quinoline (obtained by any one of the three general methods described above) was purified by automated preparative HPLC using a 250×10 mm 10 micron Luna C18 column eluting at 8 mL/min with a gradient of MeCN/water (+0.1% formic acid). The fractions containing the desired product were concentrated in vacuo to give the desired product as a formic acid salt.

Purification Method 3

The crude substituted 4-methyl-2,3-dihydro-1H-pyrrolo[3,2-c]quinoline (obtained by any one of the three general methods described above) was purified by flash chromatography eluting with dichloromethane/methanol/acetic acid/water (240:70:3:2). The fractions containing the desired product were concentrated in vacuo to give the desired product as the free base.

Purification Method 4

The crude substituted 4-methyl-2,3-dihydro-1H-pyrrolo[3,2-c]quinoline (obtained by any one of the three general methods described above) was purified by flash chromatography eluting with a mixture of methanol and dichloromethane (from 1:99 up to 1:4). The fractions containing the desired product were concentrated in vacuo to give the desired product as the free base.

(a) 6,8-Dimethoxy-4-methyl-1-(3-phenoxyphenyl)-2,3-dihydro-1H-pyrrolo[3,2-c]quinoline trifluoroacetate Prepared using General Method 1 and Purification Method 1.

LCMS (Method B): Rt=8.62 min, m/z=413.12 [M+H]$^+$; $C_{26}H_{24}N_2O_3$, Mono-isotopic mass=412.18.

$^1$H-NMR (400 MHz, $D_6$-DMSO): δ 12.95 (s, 1H), 7.60 (t, J=8.1 Hz, 1H), 7.41 (m, 2H), 7.31 (ddd, J=8.1, 2.2, 0.9 Hz, 1H), 7.24 (t, J=2.2 Hz, 1H), 7.18 (m, 1H), 7.13 (ddd, J=8.1, 2.2, 0.9 Hz, 1H), 7.09 (d, J=2.4 Hz, 1H), 7.06 (m, 2H), 5.97 (d, J=2.4 Hz, 1H), 4.39 (t, J=9.4 Hz, 2H), 4.06 (s, 3H), 3.46 (s, 3H), 3.31 (t, J=9.4 Hz, 2H), 2.61 (s, 3H).

(b) 6,8-Dimethoxy-4-methyl-1-(2-phenoxyethyl)-2,3-dihydro-1H-pyrrolo[3,2-c]quinoline trifluoroacetate Prepared using General Method 2 and Purification Method 1.

LCMS (Method B): Rt=7.77 min, m/z=365.12 [M+H]$^+$; $C_{22}H_{24}N_2O_3$, Mono-isotopic mass=364.18.

$^1$H-NMR (400 MHz, $D_6$-DMSO): δ 12.5 (s, 1H), 7.32 (d, J=2.3 Hz, 1H), 7.27 (m, 2H), 7.15 (d, J=2.3 Hz, 1H), 6.94 (m, 1H), 6.90 (m, 2H), 4.42 (t, J=5.5 Hz, 2H), 4.35 (t, J=5.5 Hz, 2H), 4.19 (t, J=9.7 Hz, 2H), 4.07 (s, 3H), 3.87 (s, 3H), 3.15 (t, J=9.7 Hz, 2H), 2.51 (s, 3H).

(c) 1-Cyclopropyl-6,8-dimethoxy-4-methyl-2,3-dihydro-1H-pyrrolo[3,2-c]quinoline trifluoroacetate Prepared using General Method 2 and Purification Method 1.

LCMS (Method B): Rt=6.42 min, m/z=285.12 [M+H]$^+$; $C_{17}H_{20}N_2O_2$, Mono-isotopic mass=284.15.

$^1$H-NMR (400 MHz, $D_6$-DMSO): δ 12.54 (s, 1H), 7.83 (d, J=2.4 Hz, 1H), 7.15 (d, J=2.4 Hz, 1H), 4.06 (s, 3H), 4.03 (t, J=9.4 Hz, 2H), 3.91 (s, 3H), 3.43 (m, 1H), 3.06 (t, J=9.4 Hz, 2H), 2.50 (s, 3H), 1.12 (m, 2H), 1.06 (m, 2H).

(d) 8-Methoxy-4-methyl-1-(4-phenoxyphenyl)-2,3-dihydro-1H-pyrrolo[3,2-c]quinoline trifluoroacetate Prepared using General Method 3 and Purification Method 1.

LCMS (Method B): Rt=8.48 min, m/z=383.11 [M+H]$^+$; $C_{25}H_{22}N_2O_2$, Mono-isotopic mass=382.17.

$^1$H-NMR (400 MHz, $D_4$-methanol): δ 7.70 (d, J=9.5 Hz, 1H), 7.53 (m, 2H), 7.43 (m, 3H), 7.21 (m, 1H), 7.2 (m, 2H), 7.07 (m, 2H), 6.50 (d, J=2.8 Hz, 1H), 4.42 (t, J=9.5 Hz, 2H), 3.48 (s, 3H), 3.40 (t, J=9.5 Hz, 2H), 2.60 (s, 3H).

(e) {2-[4-(8-Methoxy-4-methyl-2,3-dihydro-1H-pyrrolo[3,2-c]quinolin-1-yl)phenoxy]ethyl}dimethylamine hydrochloride Prepared using General Method 2 and Purification Method 1. The product was then converted to the hydrochloride salt by the addition of 1 N hydrochloric acid followed by evaporation.

LCMS (Method B): Rt=4.63 min, m/z=378.18 [M+H]$^+$; $C_{23}H_{27}N_3O_2$, Mono-isotopic mass=377.21.

$^1$H-NMR (400 MHz, $D_4$-methanol): δ 7.72 (d, J=9.3 Hz, 1H), 7.55 (m, 2H), 7.42 (dd, J=9.3, 2.7 Hz, 1H), 7.29 (m, 2H), 6.44 (d, J=2.7 Hz, 1H), 4.47 (t, J=4.9 Hz, 2H), 4.40 (t, J=9.4 Hz, 2H), 3.67 (t, J=4.9 Hz, 2H), 3.41 (s, 3H), 3.40 (t, J=9.4 Hz, 2H), 3.02 (s, 6H), 2.61 (s, 3H).

(f) 8-Methoxy-4-methyl-1-[4-(pyridin-3-yloxy)phenyl]-2,3-dihydro-1H-pyrrolo[3,2-c]quinoline trifluoroacetate Prepared using General Method 3 and Purification Method 1.

LCMS (Method B): Rt=6.60 min, m/z=384.12 [M+H]$^+$; $C_{24}H_{21}N_3O_2$, Mono-isotopic mass=383.16

$^1$H-NMR (400 MHz, $D_4$-methanol): δ 8.54 (d, J=2.9 Hz, 1H), 8.51 (dd, J=5, 1.3 Hz, 1H), 7.86 (ddd, J=8.6, 2.9, 1.3 Hz, 1H), 7.75 (d, J=9.4 Hz, 1H), 7.75 (ddd, J=8.6, 5.0, 0.6 Hz, 1H), 7.65 (m, 2H), 7.45 (dd, J=9.4, 2.8 Hz, 1H), 7.38 (m, 2H), 6.50 (d, J=2.8 Hz, 1H), 4.45 (t, J=9.5 Hz, 2H), 3.50 (s, 3H), 3.43 (t, J=9.5 Hz, 2H), 2.63 (s, 3H).

(g) 4-Methyl-8-phenoxy-1-phenyl-2,3-dihydro-1H-pyrrolo[3,2-c]quinoline hydrochloride Prepared using General Method 2 and Purification Method 3.

LCMS (Method B): Rt=7.95 min, m/z=353.10 [M+H]$^+$; $C_{24}H_{20}N_2O$, Mono-isotopic mass=352.16.

$^1$H-NMR (400 MHz, $D_6$-DMSO): δ 14.26 (s, 1H), 8.03 (d, J=9.2 Hz, 1H), 7.60 (dd, J=9.2, 2.6 Hz, 1H), 7.32 (m, 7H), 7.18 (m, 1H), 6.85 (m, 2H), 6.29 (d, J=2.6 Hz, 1H), 4.28 (t, J=9.5 Hz, 2H), 3.30 (t, J=9.5 Hz, 2H), 2.60 (s, 3H).

(h) 1-Benzyl-4-methyl-8-phenoxy-2,3-dihydro-1H-pyrrolo[3,2-c]quinoline

Prepared using General Method 2 and Purification Method 3. LCMS (Method B): Rt=8.17 min, m/z=367.13 [M+H]$^+$; $C_{25}H_{22}N_2O$, Mono-isotopic mass=366.17.

$^1$H-NMR (400 MHz, $D_6$-DMSO): δ 7.97 (d, J=9.3 Hz, 1H), 7.58 (dd, J=9.3, 2.4 Hz, 1H), 7.33 (m, 3H), 7.27 (m, 3H), 7.17 (m, 1H), 7.07 (m, 2H), 6.90 (m, 2H), 4.97 (s, 2H), 4.12 (t, J=9.6 Hz, 2H), 3.23 (t, J=9.6 Hz, 2H), 2.53 (s, 3H).

(i) 1-(Indan-2-yl)-4-methyl-8-phenoxy-2,3-dihydro-1H-pyrrolo[3,2-c]quinoline Prepared using General Method 2 and Purification Method 3.
LCMS (Method B): Rt=8.87 min, m/z=393.17 [M+H]$^+$; $C_{27}H_{24}N_2O$, Mono-isotopic mass=392.19.
$^1$H-NMR (400 MHz, D$_6$-DMSO): δ 7.95 (d, J=9.3 Hz, 1H), 7.75 (d, J=2.5 Hz, 1H), 7.56 (dd, J=9.3, 2.5 Hz, 1H), 7.39 (m, 2H), 7.24 (m, 2H), 7.19 (m, 2H), 7.14 (m, 1H), 7.10 (m, 2H), 5.24 (m, 1H), 3.78 (t, J=9.5 Hz, 2H), 3.18 (dd, J=16.2, 5.7 Hz, 2H), 3.11 (dd, J=16.2, 7.5 Hz, 2H), 3.02 (t, J=9.5 Hz, 2H), 2.45 (s, 3H).

(j) 4-Methyl-6-phenoxy-1-phenyl-2,3-dihydro-1H-pyrrolo[3,2-c]quinoline hydrochloride Prepared using General Method 2 and Purification Method 3.
LCMS (Method B): Rt=8.11 min, m/z=353.12 [M+H]$^+$; $C_{24}H_{20}N_2O$, Mono-isotopic mass=352.16.
$^1$H-NMR (400 MHz, D$_6$-DMSO): δ 13.15 (s, 1H), 7.60 (m, 5H), 7.51 (m, 2H), 7.30 (m, 1H), 7.21 (m, 2H), 7.16 (dd, J=8.5, 7.9 Hz, 1H), 7.08 (dd, J=7.9, 1.3 Hz, 1H), 6.68 (dd, J=8.5, 1.3 Hz, 1H), 4.44 (t, J=9.5 2H), 3.39 (t, J=9.5 2H), 2.68 (s, 3H).

(k) 1-Benzyl-4-methyl-6-phenoxy-2,3-dihydro-1H-pyrrolo[3,2-c]quinoline hydrochloride Prepared using General Method 2 and Purification Method 3.
LCMS (Method B): Rt=8.28 min, m/z=367.16 [M+H]$^+$; $C_{25}H_{22}N_2O$, Mono-isotopic mass=366.17
$^1$H-NMR (400 MHz, D$_6$-DMSO): δ 12.84 (s, 1H), 7.75 (dd, J=8.8, 0.9 Hz, 1H), 7.49 (m, 2H), 7.39 (m, 4H), 7.30 (m, 3H), 7.19 (m, 2H), 7.10 (dd, J=7.9, 0.9 Hz, 1H), 5.24 (s, 2H), 4.18 (t, J=9.6 Hz, 2H), 3.27 (t, J=9.6 Hz, 2H), 2.58 (s, 3H).

(l) 1-(Indan-2-yl)-4-methyl-6-phenoxy-2,3-dihydro-1H-pyrrolo[3,2-c]quinoline hydrochloride Prepared using General Method 2 and Purification Method 3.
LCMS (Method B): Rt=8.95 min, m/z=393.17 [M+H]$^+$; $C_{27}H_{24}N_2O$, Mono-isotopic mass=392.19.
$^1$H-NMR (400 MHz, D$_6$-DMSO): δ 12.75 (s, 1H), 8.20 (d, J=8.9 Hz, 1H), 7.49 (m, 3H), 7.31 (m, 3H), 7.22 (m, 5H), 5.61 (m, 1H), 3.94 (t, J=9.4 Hz, 2H), 3.42 (dd, J=16.3, 7.5 Hz, 2H), 3.32 (dd, J=16.3, 5.5 Hz, 2H), 3.10 (t, J=9.4 Hz, 2H), 2.53 (s, 3H).

(m) 4-Methyl-1-(2-phenylethyl)-8-phenoxy-2,3-dihydro-1H-pyrrolo[3,2-c]quinoline hydrochloride Prepared using General Method 2 and Purification Method 3. The product was then converted to the hydrochloride salt by addition of 1 N hydrochloric acid, followed by evaporation.
LCMS (Method B): Rt=8.58 min, m/z=381.11 [M+H]$^+$; $C_{26}H_{24}N_2O$, Mono-isotopic mass=380.19.
$^1$H-NMR (400 MHz, D$_6$-DMSO): δ 13.91 (s, 1H) 8.03 (d, J=9.3 Hz, 1H), 7.67 (dd, J=9.3, 2.4 Hz, 1H), 7.56 (d, J=2.4 Hz, 1H), 7.45 (m, 2H), 7.21 (m, 4H), 7.14 (m, 2H), 7.02 (m, 2H), 3.96 (t, J=9.6 Hz, 2H), 3.89 (t, J=7.6 Hz, 2H), 3.08 (t, J=9.6 Hz, 2H), 2.89 (t, J=7.6 Hz, 2H), 2.49 (s, 3H)

(n) 8-Methoxy-4-methyl-1-(4-phenoxyphenyl)-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.
LCMS Method B; Rt=8.48 min, M+=383.15 [M+H]+; $C_{25}H_{22}N_2O_2$, Mono-isotopic mass=382.17.
$^1$H-NMR (400 MHz, D$_6$-DMSO): δ 14.22 (s, 1H), 7.97 (d, J=9.3 Hz, 1H), 7.60 (m, 2H), 7.51 (dd, J=9.3, 2.7 Hz, 1H), 7.46 (m, 2H), 7.22 (m, 3H), 7.07 (m, 2H), 6.36 (d, J=2.7 Hz, 1H), 4.38 (t, J=9.5 Hz, 2H), 3.45 (s, 3H), 3.34 (t, J=9.5 Hz, 2H), 2.61 (s, 3H).

(o) 8-Methoxy-4-methyl-1-(2-phenylethyl)-2,3-dihydro-1H-pyrrolo[3,2-c]quinolin-6-ol trifluoroacetate Prepared using General Method 2 and Purification Method 1 (a side-product from the preparation of Example 3 (viii) below).
LCMS (Method B): Rt=7.42 min, m/z=335.12 [M+H]$^+$; $C_{21}H_{22}N_2O_2$, Mono-isotopic mass=334.17.
$^1$H-NMR (400 MHz, D$_6$-DMSO): δ 12.45 (s, 1H), 11.79 (s, 1H), 7.32 (m, 4H), 7.23 (m, 1H), 6.89 (d, J=2.4 Hz, 1H), 6.86 (d, J=2.4 Hz, 1H), 4.14 (t, J=7.5 Hz, 2H), 4.00 (t, J=9.7 Hz, 2H), 3.81 (s, 3H), 3.11 (t, J=7.5 Hz, 2H), 3.08 (t, J=9.7 Hz, 2H), 2.49 (s, 3H).

(p) 1-(1-Benzyl-piperidin-4-yl)-4-methyl-8-phenoxy-2,3-dihydro-1H-pyrrolo[3,2-c]quinoline bis-trifluoroacetate Prepared using General Method 2 and Purification Method 1.
LCMS (Method B): Rt=5.90 min, m/z=450.22 [M+H]$^+$; $C_{30}H_{31}N_3O$, Mono-isotopic mass=449.25
1H-NMR (400 MHz, D$_6$-DMSO, NaOD): δ 7.79 (d, J=9.2 Hz, 1H), 7.46 (m, 2H), 7.35 (m, 3H), 7.27 (m, 5H), 7.14 (m, 2H), 3.71 (m, 1H), 3.64 (t, J=9.4 Hz, 2H), 3.40 (s, 2H), 2.97 (t, J=9.4 Hz, 2H), 2.74 (d, br, J=10.6 Hz, 2H), 2.36 (s, 3H), 1.63 (m, 6H).

(q) 1-(Indan-1-yl)-4-methyl-8-phenoxy-2,3-dihydro-1H-pyrrolo[3,2-c]quinoline hydrochloride Prepared using General Method 2 and Purification Method 3.
LCMS (Method B): Rt=9.05 min, m/z=393.09 [M+H]$^+$; $C_{27}H_{24}N_{20}$, Mono-isotopic mass=392.19.
$^1$H-NMR (400 MHz, D$_6$-DMSO): δ 13.92 (s, 1H), 8.04 (d, J=9.3 Hz, 1H), 7.77 (s, 1H), 7.67 (dd, J=9.3, 1.8 Hz, 1H), 7.41 (m, 2H), 7.32 (m, 2H), 7.24 (m, 2H), 7.18 (m, 1H), 7.11 (m, 2H), 6.00 (t, J=7.0 Hz, 1H), 3.72 (m, 1H), 3.57 (m, 1H), 3.05 (m, 3H), 2.83 (m, 1H), 2.50 (s, 3H), 2.22 (m, 2H)

(r) 1-(Benzodioxan-2-ylmethyl)-4-methyl-8-phenoxy-2,3-dihydro-1H-pyrrolo[3,2-c]quinoline hydrochloride Prepared using General Method 2 and Purification Method 3.
LCMS (Method B): Rt=8.57 min, m/z=425.10[M+H]$^+$; $C_{27}H_{24}N_2O_3$, Mono-isotopic mass=424.18.
$^1$H-NMR (400 MHz, D$_6$-DMSO): δ 13.99 (s, 1H), 8.02 (d, J=9.3 Hz, 1H), 7.72 (d, J=2.4 Hz, 1H), 7.67 (dd, J=9.3, 2.4

Hz, 1H), 7.27 (m, 2H), 7.11 (m, 1H), 7.05 (m, 2H), 6.88 (dd, J=8.0, 1.7 Hz, 1H), 6.83 (ddd, J=8.0, 7.1, 1.7 Hz, 1H), 6.77 (ddd, J=8.0, 7.1, 1.7 Hz, 1H), 6.57 (dd, J=8.0, 1.7 Hz, 1H), 4.57 (m, 1H), 4.25 (dd, J=11.5, 2.3 Hz, 1H), 4.18 (m, 1H), 4.02 (m, 2H), 3.92 (dd, J=15.8, 3.7 Hz, 1H), 3.72 (dd, J=11.5, 7.3 Hz, 1H), 3.17 (m, 2H), 2.52 (s, 3H).

(s) 4-Methyl-8-phenoxy-1-(1,2,3,4-tetrahydronaphthalen-1-yl)-2,3-dihydro-1H-pyrrolo[3,2-c]quinoline hydrochloride Prepared using General Method 2 and Purification Method 3.
LCMS (Method B): Rt=9.12 min, m/z=407.20 [M+H]$^+$; $C_{28}H_{26}N_2O$, Mono-isotopic mass=406.20
$^1$H-NMR (400 MHz, $D_6$-DMSO): δ 13.90 (s, br, 1H), 8.02 (d, J=9.3 Hz, 1H), 7.67 (d, br, J=9.3 Hz, 1H), 7.48 (s, br, 1H), 7.36 (m, 2H), 7.13 (m, 7H), 5.53 (s, br, 1H), 3.90 (s, br, 1H), 3.56 (s, br, 1H), 3.10 (t, J=9.6 Hz, 2H), 2.73 (m, br, 2H), 2.52 (s, 3H), 1.99 (m, br, 2H), 1.90 (m, 1H), 1.68 (m, 1H).

(t) 1-Cyclohexyl-4-methyl-8-phenoxy-2,3-dihydro-1H-pyrrolo[3,2-c]quinoline

Prepared using General Method 3 and Purification Method 4.
LCMS (Method B): Rt=8.83 min, m/z=359.17 [M+H]$^+$; $C_{24}H_{26}N_2O$, Mono-isotopic mass=358.20.
$^1$H-NMR (400 MHz, $D_6$-DMSO): δ 13.80 (s, 1H), 8.02 (d, J=9.4 Hz, 1H), 7.72 (dd, J=9.4, 2.6 Hz, 1H), 7.50 (m, 2H), 7.39 (d, J=2.6 Hz, 1H), 7.27 (m, 1H), 7.21 (m, 2H), 3.98 (t, J=9.6 Hz, 2H), 3.96 (m, 1H), 3.07 (t, J=9.6 Hz, 2H), 2.47 (s, 3H), 1.75 (d, J=12.0 Hz, 2H), 1.57 (m, 5H), 1.07 (m, 1H), 0.87 (m, 2H).

(u) 8-Ethoxy-4-methyl-1-(4-phenoxyphenyl)-2,3-dihydro-1H-pyrrolo[3,2-c]quinoline formate Prepared using General Method 2 and Purification Method 2,
LCMS (Method B): Rt=8.94 min, m/z=397.15 [M+H]$^+$; $C_{26}H_{24}N_2O_2$, Mono-isotopic mass=396.18.
$^1$H-NMR (400 MHz, $D_4$-methanol): δ 8.50 (br s, 1H), 7.71 (d, J=9.3 Hz, 1H), 7.57 (t, J=8.1 Hz, 1H), 7.42 (dd, J=9.3, 2.6 Hz, 1H), 7.37 (m, 2H), 7.24 (ddd, J=8.1, 2.2, 0.9 Hz, 1H), 7.16 (m, 1H), 7.12 (ddd, J=8.1, 2.2, 0.9 Hz, 1H), 7.09 (t, J=2.2 Hz, 1H), 7.04 (m, 2H), 6.50 (d, J=2.6 Hz, 1H), 4.39 (t, J=9.5 Hz, 2H), 3.67 (q, J=7.0 Hz, 2H), 3.37 (t, J=9.5 Hz, 2H), 2.59 (s, 3H), 1.28 (t J=7.0 Hz, 3H).

Example 2

The following compounds were prepared, from appropriate intermediates (such as those described hereinbefore), according to or by analogy with methods described herein:

(i) 1-(4-methoxyphenyl)-4-methyl-8-phenoxy-2,3-dihydro-1H-pyrrolo[3,2-c]quinoline trifluoroacetate Prepared using General Method 3 and Purification Method 1.
LCMS (Method B): Rt=8.14 min, m/z=383.11 [M+H]$^+$; $C_{25}H_{22}N_2O_2$, Mono-isotopic mass=382.17.
$^1$H-NMR (400 MHz, $D_4$-methanol): δ 7.77 (d, J=9.2 Hz, 1H), 7.59 (dd, J=9.2, 2.6 Hz, 1H), 7.30 (m, 2H), 7.18 (m, 3H), 6.82 (m, 4H), 6.41 (d, J=2.6 Hz, 1H), 4.27 (t, J=9.5 Hz, 2H), 3.84 (s, 3H), 3.33 (t, J=9.5 Hz, 2H), 2.58 (s, 3H).

(ii) 4-methyl-1-(4-phenoxyphenyl)-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.
LCMS (Method B): Rt=8.34 min, m/z=353.10 [M+H]$^+$; $C_{24}H_{20}N_2O$, Mono-isotopic mass=352.16.
$^1$H-NMR (400 MHz, $D_6$-DMSO): δ 14.0 (s, 1H), 7.99 (d, J=8.7 Hz, 1H), 7.82 (m, 1H), 7.58 (m, 2H), 7.47 (m, 2H), 7.34 (m, 1H), 7.23 (m, 1H), 7.20 (m, 2H), 7.16 (m, 2H), 7.06 (dd, J=8.7, 1.2 Hz, 1H), 4.38 (t, J=9.4 Hz, 2H), 3.34 (t, J=9.4 Hz, 2H), 2.62 (s, 3H).

(iii) 4-methyl-1-(2-methylphenyl)methyl-8-phenoxy-2,3-dihydro-1H-pyrrolo[3,2-d]quinoline hydrochloride Prepared using General Method 2 and Purification Method 1. The Product was then converted to the hydrochloride salt by the addition of 1 N hydrochloric acid, followed by evaporation.
LCMS (Method B): Rt=8.48 min, m/z=381.17 [M+H]$^+$; $C_{26}H_{24}N_2O$, Mono-isotopic mass=380.19.
$^1$H-NMR (400 MHz, $D_6$-DMSO): δ 13.94 (s, br, 1H), 8.01 (d, J=9.2 Hz, 1H), 7.63 (dd, J=9.2, 2.4 Hz, 1H), 7.25 (m, 2H), 7.16 (m, 3H), 7.10 (m, 1H), 7.00 (m, 2H), 6.80 (m, 2H), 4.88 (s, 2H), 4.11 (t, J=9.6 Hz, 2H), 3.26 (t, J=9.6 Hz, 2H), 2.55 (s, 3H), 2.02 (s, 3H).

(iv) 4-methyl-8-phenoxy-1-(4-iso-propylphenyl)-2,3-dihydro-1H-pyrrolo[3,2-c]quinoline hydrochloride Prepared using General Method 2 and Purification Method 3. The product was then converted to the hydrochloride salt by the addition of 1 N hydrochloric acid, followed by evaporation.
LCMS (Method B): Rt=9.29 min, m/z=395.18 [M+H]$^+$; $C_{27}H_{26}N_2O$, Mono-isotopic mass=394.20.
$^1$H-NMR (400 MHz, $D_6$-DMSO): δ 14.1 (s, br, 1H), 8.05 (d, J=9.2 Hz, 1H), 7.64 (dd, J=9.2, 2.6 Hz, 1H), 7.32 (m, 2H), 7.30 (m, 2H), 7.23 (m, 2H), 7.13 (m, 1H), 6.86 (m, 2H), 6.49 (d, J=2.6 Hz, 1H), 4.30 (t, J=9.5 Hz, 2H), 3.31 (t, J=9.5 Hz, 2H), 2.88 (hept, J=7.0 Hz, 1H), 2.61 (s, 3H), 1.16 (d, J=7.0 Hz, 6H).

(v) 4-methyl-8-phenoxy-1-(1-phenylethyl)-2,3-dihydro-1H-pyrrolo[3,2-c]quinoline trifluoroacetate Prepared using General Method 2 and Purification Method 1.
LCMS (Method B): Rt=8.60 min, m/z=381.17 [M+H]$^+$; $C_{26}H_{24}N_2O$, Mono-isotopic mass=380.19.
$^1$H-NMR (400 MHz, $D_6$-DMSO): δ 13.5 (s, br, 1H), 7.86 (d, J=9.2 Hz, 1H), 7.61 (dd, J=9.2, 2.6 Hz, 1H), 7.53 (d, J=2.6 Hz, 1H), 7.41 (m, 2H), 7.29 (m, 3H), 7.23 (m, 1H), 7.16 (m, 2H), 6.97 (m, 2H), 5.69 (q, J=6.8 Hz, 1H), 4.20 (m, 1H), 3.96 (m, 1H), 3.19 (t, J=9.6 Hz, 2H), 2.50 (s, 3H), 1.64 (d, J=6.8 Hz, 3H).

(vi) 8-methoxy-4-methyl-1-(2-phenylethyl)-2,3-dihydro-1H-pyrrolo[3,2-c]quinoline formate Prepared using General Method 1 and Purification Method 2.

LCMS (Method B): Rt=7.44 min, m/z=319.14 [M+H]$^+$; C$_{21}$H$_{22}$N$_2$O, Mono-isotopic mass=318.17.

$^1$H-NMR (400 MHz, D$_4$-methanol): δ 8.45 (s, 1H), 7.69 (d, J=9.2 Hz, 1H), 7.50 (dd, J=9.2, 2.6 Hz, 1H), 7.42 (d, J=2.6 Hz, 1H), 7.29 (m, 4H), 7.22 (m, 1H), 4.22 (t, J=7.2 Hz, 2H), 4.00 (t, J=9.6 Hz, 2H), 3.87 (s, 3H), 3.21 (t, J=7.2 Hz, 2H), 3.14 (t, J=9.6 Hz, 2H), 2.49 (s, 3H).

Example 3

The following compounds were prepared, from appropriate intermediates (such as those described hereinbefore), according to or by analogy with methods described herein:

(i) 6,8-dimethoxy-1-(4-hydroxyphenyl)-4-methyl-2,3-dihydro-1H-pyrrolo[3,2-c]quinoline Prepared using General Method 2 and Purification Method 3.

LCMS (Method B): Rt=6.43 min, m/z=337.13 [M+H]$^+$; C$_{20}$H$_{20}$N$_2$O$_3$, Mono-isotopic mass=336.15.

$^1$H-NMR (400 MHz, D$_6$-DMSO): δ 9.50 (s, br, 1H), 7.07 (m, 2H), 6.81 (m, 2H), 6.53 (d, J=2.6 Hz, 1H), 5.90 (d, J=2.6 Hz, 1H), 3.95 (t, J=9.2 Hz, 2H), 3.84 (s, 3H), 3.32 (s, 3H), 3.16 (t, J=9.2 Hz, 2H), 2.42 (s, 3H).

(ii) 6,8-dimethoxy-1-(3-hydroxyphenyl)-4-methyl-2,3-dihydro-1H-pyrrolo[3,2-c]quinoline formate Prepared using General Method 2 and Purification Method 2.

LCMS (Method B): Rt=6.68 min, m/z=337.09 [M+H]$^+$; C$_{20}$H$_{20}$N$_2$O$_3$, Mono-isotopic mass=336.15.

$^1$H-NMR (400 MHz, D$_6$-DMSO): δ 8.18 (s, 1H), 7.21 (t, J=8.0 Hz, 1H), 6.65 (m, 3H), 6.58 (t, J=2.2 Hz, 1H), 6.04 (d, J=2.5 Hz, 1H), 4.13 (t, J=9.2 Hz, 2H), 3.90 (s, 3H), 3.39 (s, 3H), 3.21 (t, J=9.2 Hz, 2H), 2.48 (s, 3H).

(iii) 6,8-dimethoxy-1-(3-hydroxy-5-methylphenyl)-4-methyl-2,3-dihydro-1H-pyrrolo[3,2-c]quinoline formate Prepared using General Method 2 and Purification Method 2.

LCMS (Method B): Rt=7.14 min, m/z=351.12 [M+H]$^+$; C$_{21}$H$_{22}$N$_2$O$_3$, Mono-isotopic mass=350.16.

$^1$H-NMR (400 MHz, D$_6$-DMSO): δ 8.18 (s, 1 h), 6.64 (d, J=2.5 Hz, 1H), 6.46 (m, 2H), 6.36 (t, J=2.0 Hz, 1H), 6.08 (d, J=2.5 Hz, 1H), 4.11 (t, J=9.2 Hz, 2H), 3.89 (s, 3H), 3.41 (s, 3H), 3.20 (t, J=9.2 Hz, 2H), 2.46 (s, 3H), 2.21 (s, 3H).

(iv) 8-methoxy-1-(4-methoxyphenyl)-4-methyl-2,3-dihydro-1H-pyrrolo[3,2-c]quinoline trifluoroacetate Prepared using General Method 3 and Purification Method 1.

LCMS (Method B): Rt=7.03 min, m/z=321.12 [M+H]$^+$; C$_{20}$H$_{20}$N$_2$O$_2$, Mono-isotopic mass=320.15.

$^1$H-NMR (400 MHz, D$_6$-DMSO): δ 13.55 (s, 1H), 7.79 (d, J=9.3 Hz, 1H), 7.52 (m, 2H), 7.49 (dd, J=9.3, 2.8 Hz, 1H), 7.17 (m, 2H), 6.31 (d, J=2.8 Hz, 1H), 4.35 (t, J=9.5 Hz, 2H), 3.83 (s, 3H), 3.36 (s, 3H), 3.33 (t, J=9.5 Hz, 2H), 2.57 (s, 3H).

(v) 8-trifluoromethoxy-1-(4-phenoxyphenyl)-4-methyl-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (Method B): Rt=8.95 min, m/z=437.10 [M+H]$^+$; C$_{25}$H$_{19}$F$_3$N$_2$O$_2$, Mono-isotopic mass=436.14.

$^1$H-NMR (400 MHz, D$_6$-DMSO): δ 14.4 (s, br, 1H), 8.17 (d, J=9.4 Hz, 1H), 7.86 (dd, J=9.4, 2.6 Hz, 1H), 7.62 (m, 2H), 7.46 (m, 2H), 7.23 (m, 3H), 7.09 (m, 2H), 6.80 (m, 1H), 4.41 (t, J=9.5 Hz, 2H), 3.36 (t, J=9.5 Hz, 2H), 2.64 (s, 3H).

(vi) 6,8-dimethoxy-4-methyl-1-[4-(pyridin-3-yloxy)phenyl]-2,3-dihydro-1H-pyrrolo[3,2-c]quinoline trifluoroacetate Prepared using General Method 2 and Purification Method 1.

LCMS (Method B): Rt=6.82 min, m/z=414.12 [M+H]$^+$; C$_{25}$H$_{23}$N$_3$O$_3$, Mono-isotopic mass=413.17

$^1$H-NMR (400 MHz, D$_6$-DMSO): δ 12.9 (s, 1H), 8.45 (m, 2H), 7.61 (m, 2H), 7.52 (m, 2H), 7.30 (m, 2H), 7.07 (d, J=2.4 Hz, 1H), 5.94 (d, J=2.4 Hz, 1H), 4.39 (t, J=9.5 Hz, 2H), 4.06 (s, 3H), 3.43 (s, 3H), 3.33 (t, J=9.5 Hz, 2H), 2.62 (s, 3H).

(vii) 1-benzyl-6,8-dimethoxy-4-methyl-2,3-dihydro-1H-pyrrolo[3,2-c]quinoline formate Prepared using General Method 2 and Purification Method 2.

LCMS (Method B): Rt=7.39 min, m/z=335.13 [M+H]$^+$; C$_{21}$H$_{22}$N$_2$O$_2$, Mono-isotopic mass=334.17

$^1$H-NMR (400 MHz, D6-DMSO): δ 8.22 (s, 1H), 7.38 (m, 4H), 7.28 (m, 1H), 6.66 (d, J=2.5 Hz, 1H), 6.62 (d, J=2.5 Hz, 1H), 4.93 (s, 2H), 3.92 (t, J=9.5 Hz, 2H), 3.87 (s, 3H), 3.44 (s, 3H), 3.14 (t, J=9.5 Hz, 2H), 2.41 (s, 3H).

(viii) 6,8-dimethoxy-4-methyl-1-(2-phenylethyl)-2,3-dihydro-1H-pyrrolo[3,2-c]quinoline formate Prepared using General Method 2 and Purification Method 2.

LCMS (Method B): Rt=7.82 min, m/z=349.14 [M+H]$^+$; C$_{22}$H$_{24}$N$_2$O$_2$, Mono-isotopic mass=348.18.

$^1$H-NMR (400 MHz, D$_6$-DMSO): δ 8.22 (s, 1H), 7.31 (m, 4H), 7.22 (m, 1H), 6.74 (d, J=2.5 Hz, 1H), 6.72 (d, J=2.5 Hz, 1H), 3.90 (s, 3H), 3.85 (t, J=7.6 Hz, 2H), 3.77 (s, 3H), 3.76 (t, J=9.5 Hz, 2H), 3.03 (t, J=9.5 Hz, 2H), 2.97 (t, J=7.6 Hz, 2H), 2.38 (s, 3H).

(ix) 4-methyl-1-(2-phenylethyl)-8-trifluoromethoxy-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (Method B): Rt=8.09 min, m/z=373.08 [M+H]$^+$; C$_{21}$H$_{19}$F$_3$N$_2$O, Mono-isotopic mass=372.14.

$^1$H-NMR (400 MHz, D6-DMSO): 13.95 (s, br, 1H), 8.06 (d, J=9.5 Hz, 1H), 7.99 (d, J=2.3 Hz, 1H), 7.91 (m, 1H), 7.29

(m, 4H), 7.20 (m, 1H), 4.16 (t, J=7.4 Hz, 2H), 4.06 (t, J=9.5 Hz, 2H), 3.12 (t, J=9.5 Hz, 2H), 3.08 (t, J=7.4 Hz, 2H), 2.50 (s, 3H).

(x) 6,8-dimethoxy-1-(indan-1-yl)-4-methyl-2,3-dihydro-1H-pyrrolo[3,2-c]quinoline formate Prepared using General Method 2 and Purification Method 2, LCMS (Method B): Rt=8.19 min, m/z=361.14 [M+H]$^+$; $C_{23}H_{24}N_2O_2$, Mono-isotopic mass=360.18.

$^1$H-NMR (400 MHz, D$_6$-DMSO): δ 8.20 (s, 1H), 7.32 (d, J=7.4 Hz, 1H), 7.26 (td, J=7.4, 1.5 Hz, 1H), 7.20 (t, J=7.4 Hz, 1H), 7.17 (d, J=7.4 Hz, 1H), 6.99 (d, J=2.4 Hz, 1H), 6.76 (d, J=2.4 Hz, 1H), 6.07 (t, J=7.4 Hz, 1H), 3.92 (s, 3H), 3.80 (s, 3H), 3.50 (q, J=10.0 Hz, 1H), 3.36 (td, J=10.0, 7.4 Hz, 1H), 2.97 (m, 4H), 2.45 (m, 1H), 2.40 (s, 3H), 2.13 (m, 1H).

(xi) 6,8-dimethoxy-4-methyl-1-[(6-phenoxy)pyridin-3-yl]-2,3-dihydro-1H-pyrrolo[3,2-c]quinoline trifluoroacetate Prepared using General Method 2 and Purification Method 1.

LCMS (Method B): Rt=7.86 min, m/z=414.12 [M+H]$^+$; $C_{25}H_{23}N_3O_3$, Mono-isotopic mass=413.17.

$^1$H-NMR (400 MHz, D$_6$-DMSO): δ 13.01 (s, 1H), 8.38 (d, J=2.8 Hz, 1H), 8.10 (d, J=8.7, 2.8 Hz, 1H), 7.47 (m, 2H), 7.28 (d, J=8.7 Hz, 1H), 7.26 (m, 1H), 7.15 (m, 2H), 7.09 (d, J=2.4 Hz, 1H), 5.89 (d, J=2.4 Hz, 1H), 4.38 (t, J=9.5 Hz, 2H), 4.06 (s, 3H), 3.47 (s, 3H), 3.34 (t, 2H), 2.64 (s, 3H).

(xii) 6,8-dimethoxy-1-[(6-methoxy)pyridin-3-yl]-4-methyl-2,3-dihydro-1H-pyrrolo[3,2-c]quinoline trifluoroacetate Prepared using General Method 2 and Purification Method 1.

LCMS (Method B): Rt=6.57 min, m/z=352.13 [M+H]$^+$; $C_{20}H_{21}N_3O_3$, Mono-isotopic mass=351.16.

$^1$H-NMR (400 MHz, D$_6$-DMSO): δ 12.96 (s, 1H), 8.43 (dd, J=2.8, 0.5 Hz, 1H), 7.95 (dd, J=8.8, 2.8 Hz, 1H), 7.08 (d, J=2.4 Hz, 1H), 7.07 (dd, J=8.8, 0.5 Hz, 1H), 5.88 (d, J=2.4 Hz, 1H), 4.36 (t, J=9.4 Hz, 2H), 4.06 (s, 3H), 3.92 (s, 3H), 3.39 (s, 3H), 3.33 (t, J=9.4 Hz, 2H), 2.63 (s, 3H).

(xiii) 1-(benzodioxol-5-ylmethyl)-6,8-dimethoxy-4-methyl-2,3-dihydro-1H-pyrrolo[3,2-c]quinoline formate Prepared using General Method 2 and Purification Method 2.

LCMS (Method B): Rt=7.39 min, m/z=379.16 [M+H]$^+$; $C_{22}H_{22}N_2O_4$, Mono-isotopic mass=378.16

$^1$H-NMR (400 MHz, D$_6$-DMSO): δ 8.21 (s, 1H), 6.94 (d, J=1.7 Hz, 1H), 6.89 (d, J=7.9 Hz, 1H), 6.86 (dd, J=7.9, 1.7 Hz, 1H), 6.67 (m, 2H), 5.99 (s, 2H), 4.81 (s, 2H), 3.88 (s, 3H), 3.87 (t, J=9.5 Hz, 2H), 3.55 (s, 3H), 3.11 (t, J=9.5 Hz, 2H), 2.40 (s, 3H).

Example 4

The following compounds were prepared, from appropriate intermediates (such as those described hereinbefore), according to or by analogy with methods described herein:

(a) 6,8-dimethoxy-4-methyl-1-(3-methylbutyl)-2,3-dihydro-1H-pyrrolo[3,2-c]quinoline formate Prepared using General Method 2 and Purification Method 2.

LCMS (method B): Rt=7.90 min, m/z=315.14[M+H]$^+$; $C_{19}H_{26}N_2O_2$, Mono-isotopic mass=314.20

$^1$H NMR (400 MHz, D$_6$-DMSO) δ 8.21 (s, 1H), 6.83 (d, J=2.5 Hz, 1H), 6.79 (d, J=2.5 Hz, 1H), 3.92 (s, 3H), 3.85 (s, 3H), 3.82 (t, J=9.4 Hz, 2H), 3.66 (m, 2H), 3.04 (t, J=9.4 Hz, 2H), 2.39 (s, 3H), 1.69 (m, 1H), 1.59 (m, 2H), 0.95, (d, J=6.5 Hz, 6H).

(b) 1-cyclopropylmethyl-6,8-dimethoxy-4-methyl-2,3-dihydro-1H-pyrrolo[3,2-c]quinoline trifluoroacetate Prepared using General Method 2 and Purification Method 1.

LCMS (method B): Rt=7.04 min, m/z=299.13[M+H]$^+$; $C_{18}H_{22}N_2O_2$, Mono-isotopic mass=298.17

$^1$H NMR (400 MHz, D$_6$-DMSO) δ 12.40 (br s, 1H), 7.15 (d, J=2.3 Hz, 1H), 7.13 (d, J=2.3 Hz, 1H), 4.15 (t, J=9.5 Hz, 2H), 4.07 (s, 3H), 3.92 (s, 3H), 3.86 (d, J=6.6 Hz, 2H), 3.13 (t, J=9.5/hz, 2H), 2.50 (s, 3H), 1.24 (m, 1H), 0.61 (m, 2H) 0.41 (m, 2H).

(c) 4-methyl-8-(morpholin-4-yl)-1-(4-phenoxyphenyl)-2,3-dihydro-1H-pyrrolo[3,2-c]quinoline formate Prepared using General Method 2 and Purification Method 2.

LCMS (method B): Rt=8.21 min, m/z=438.15[M+H]$^+$; $C_{28}H_{27}N_3O_2$, Mono-isotopic mass=437.21

$^1$H NMR (400 MHz, D$_4$-methanol) δ 8.54 (s, 1H), 7.69 (d, J=9.5 Hz, 1H), 7.58 (dd, J=9.5, 2.6 Hz, 1H), 7.53 (t, J=8.0 Hz, 1H), 7.36 (m, 2H), 7.16 (m, 2H), 7.03 (m, 4H), 6.43 (d, J=2.6 Hz, 1H), 4.34 (t, J=9.3 Hz, 2H), 3.74 (m, 4H), 3.33 (t, J=9.3 Hz, 2H), 2.89 (m, 4H) 2.56 (s, 3H).

(d) 8-methoxy-4-methyl-1-(1,2,3,4-tetrahydronaphthalen-1-yl)-2,3-dihydro-1H-pyrrolo[3,2-c]quinoline formate Prepared using General Method 2 and Purification Method 2.

LCMS (method B): Rt=8.00 min, m/z=345.18[M+H]$^+$; $C_{23}H_{24}N_2O$, Mono-isotopic mass=344.19

$^1$H NMR (400 MHz, D$_4$-methanol) δ 8.54 (s, 1H), 7.74 (d, J=9.5 Hz, 1H), 7.34 (d, J=7.0 Hz, 1H), 7.17 (m, 5H), 5.52 (br s, 1H), 3.67 (br m, 5H), 3.05 (t, J=9.4 Hz, 2H), 2.88 (m, 2H), 2.45 (s, 3H), 2.11 (m, 3H), 1.88 (m, 1H).

(e) 4-methyl-1-(2-phenylethyl)-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=7.25 min, m/z=289.17[M+H]$^+$; $C_{20}H_{20}N_2$, Mono-isotopic mass=288.16

$^1$H NMR (400 MHz, D$_6$-DMSO) δ 13.59 (s, 1H), 8.2 (d, J=8.6 Hz, 1H), 7.92 (dd, J=8.7, 1.4 Hz, 1H), 7.86 (m, 1H), 7.55 (m, 1H), 7.33 (m, 4H), 7.23 (m, 1H), 4.17 (t, J=7.4 Hz, 2H), 3.99 (m, 2H), 3.09 (m, 4H), 2.49 (s, 3H).

(f) 4,6-dimethyl-1-(2-methylphenyl)-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=7.25 min, m/z=289.15[M+H]$^+$; $C_{20}H_{20}N_2$, Mono-isotopic mass=288.16

$^1$H NMR (400 MHz, $D_6$-DMSO) δ 12.06 (s, 1H), 7.66 (dt, j=7.0, 1.1 Hz, 1H), 7.52 (m, 3H), 7.46 (m, 1H), 7.14 (dd, J=8.6, 7.0 Hz, 1H), 6.68 (d, J=8.6 Hz, 1H), 4.33 (m, 2H), 3.40 (m, 2H), 2.71 (s, 3H), 2.67 (s, 3H), 2.18 (s, 3H).

(g) 4,6-dimethyl-1-(2-phenylethyl)-2,3-dihydro-1H-pyrrolo[3,2-d]quinoline hydrochloride Prepared using General Method 2 and Purification Method 1. The product was then converted to the hydrochloride salt by the addition of 1 N hydrochloric acid, followed by evaporation.

LCMS (method B): Rt=7.60 min, m/z=303.19[M+H]$^+$; $C_{21}H_{22}N_2$, Mono-isotopic mass=302.18

$^1$H NMR (400 MHz, $D_6$-DMSO) δ 11.73 (s, 1H), 8.08 (d, J=8.6 Hz, 1H), 7.74 (dt, J=7.2, 1.0 Hz, 1H), 7.47 (dd, J=8.6, 7.2 Hz, 1H), 7.33 (m, 4H), 7.24 (m, 1H), 4.16 (t, J=7.5 Hz, 2H), 4.00 (m, 2H), 3.09 (m, 4H), 2.67 (s, 3H), 2.58 (s, 3H).

(h) 4-methyl-8-(piperidin-1-yl)-1-[4-(piperidin-1-yl)phenyl]-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=8.10 min, m/z=427.17[M+H]$^+$; $C_{28}H_{34}N_4$, Mono-isotopic mass=426.28

$^1$H NMR (400 MHz, $D_4$-methanol) δ 7.92 (m, 4H), 7.73 (m, 2H), 7.15 (br s, 1H), 4.48 (t, J=9.4 Hz, 2H), 3.75 (t, J=5.5 Hz, 4H), 3.44 (t, J=9.4 Hz, 2H), 3.22 (br t, J=5.5 Hz, 4H), 2.66 (s, 3H), 2.12 (m, 4H), 1.83 (m, 6H), 1.66 (m, 2H).

(i) 4-methyl-8-(piperidin-1-yl)-1-(3-phenoxyphenyl)-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=9.32 min, m/z=436.14[M+H]$^+$; $C_{29}H_{29}N_3O$, Mono-isotopic mass=435.23

$^1$H NMR (400 MHz, $D_4$-methanol) δ 7.99 (dd, J=9.5, 2.3 Hz, 1H), 7.90 (d, J=9.5 Hz, 1H), 7.61 (t, J=8.1 Hz, 1H), 7.41 (m, 2H), 7.27 (dd, J=7.9, 1.5 Hz, 1H), 7.20 (m, 2H), 7.16 (m, 2H), 7.10 (m, 2H), 4.46 (t, J=9.4 Hz, 2H), 3.41 (t, J=9.4 Hz, 2H), 3.287 (t, J=5.5 Hz, 4H), 2.63 (s, 3H), 1.88 (m, 4H), 1.70 (m, 2H).

(j) 1-{4-[2-(N,N-dimethylamino)ethoxy]phenyl}-4-methyl-8-phenoxy-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=5.43 min, m/z=440.11[M+H]$^+$; $C_{28}H_{29}N_3O_2$, Mono-isotopic mass=439.23

$^1$H NMR (400 MHz, $D_4$-methanol) δ 7.81 (d, J=9.2 Hz, 1H), 9.57 (dd, J=9.2, 2.6 Hz, 1H), 7.32 (m, 4H), 7.20 (m, 1H), 7.01 (m, 2H), 6.85 (m, 2H), 6.49 (d, J=2.6 Hz, 1H), 4.39 (t, J=5.0 Hz, 2H), 4.30 (t, J=9.4 Hz, 2H), 3.70 (t, J=5.0 Hz, 2H), 3.36 (t, J=9.4 Hz, 2H), 3.03 (s, 6H), 2.61 (s, 3H).

(k) 1-[4-(4-fluorophenoxy)phenyl]-8-methoxy-4-methyl-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=8.43 min, m/z=401.06[M+H]$^+$; $C_{25}H_{21}FN_2O_2$, Mono-isotopic mass=400.16

$^1$H NMR (400 MHz, $D_4$-methanol) δ 7.70 (d, J=9.4 Hz, 1H), 7.53 (m, 2H), 7.43 (dd, J=9.4, 2.7 Hz, 1H), 7.18 (m, 4H), 7.09 (m, 2H), 6.48 (d, J=2.7 Hz, 1H), 4.41 (t, J=9.6 Hz, 2H), 3047 (s, 3H), 3.40 (t, J=9.6 Hz, 2H), 2.61 (s, 3H).

(l) 1-(benzodioxan-2-ylmethyl)-8-methoxy-4-methyl-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=7.31 min, m/z=363.02[M+H]$^+$; $C_{22}H_{22}N_2O_3$, Mono-isotopic mass=362.16

$^1$H NMR (400 MHz, $D_4$-methanol) δ 7.71 (d, J=9.3 Hz, 1H), 7.67 (d, J=2.6 Hz, 1H), 7.50 (dd J=9.3, 2.6 Hz, 1H), 6.88 (dd, J=8.0, 1.6 Hz, 1H), 6.82 (m, 1H), 6.76 (m, 1H), 6.63 (dd, J=8.0, 1.6 Hz, 1H), 4.81 (m, 1H), 4.46 (m, 2H), 4.24 (m, 3H), 4.12 (dd, J=15.8, 4.0 Hz, 1H), 3.83 (s, 3H), 3.25 (t, J=9.7 Hz, 2H), 2.53 (s, 3H).

(m) 1-cyclohexyl-8-methoxy-4-methyl-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=7.38 min, m/z=297.13[M+H]$^+$; $C_{19}H_{24}N_2O$, Mono-isotopic mass=296.19

$^1$H NMR (400 MHz, $D_4$-methanol) δ 7.70 (m, 1H), 7.52 (m, 2H), 4.54 (m, 1H), 4.14 (t, J=9.6 Hz, 2H), 3.96 (s, 3H), 3.16 (t, J=9.6 Hz, 2H), 2.48 (s, 3H), 2.12 (d, J=12.3 Hz, 2H), 1.98 (m, 2H), 1.80 (m, 3H), 1.54 (m, 2H), 1.32 (m, 1H).

(n) 8-methoxy-4-methyl-1-phenyl-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=6.75 min, m/z=291.08[M+H]$^+$; C$_{19}$H$_{18}$N$_2$O, Mono-isotopic mass=290.14
$^1$H NMR (400 MHz, D$_4$-methanol) δ 7.72 (d, J=9.4 Hz, 1H), 7.64 (m, 2H), 7.56 (m, 3H), 7.40 (dd, J=9.4, 2.7 Hz, 1H), 6.38 (d, J=2.7 Hz, 1H), 4.45 (t, J=9.5 Hz, 2H), 3.42 (t, J=9.5 Hz, 2H), 3.33 (s, 3H), 2.62 (s, 3H).

(o) 4-methyl-8-phenoxy-1-[4-(3-pyridyl)phenyl]-2,3-dihydro-1H-pyrrolo[3,2-d]quinoline hydrochloride Prepared using General Method 2 and Purification Method 1. The product was then converted to the hydrochloride salt by the addition of 1 N hydrochloric acid, followed by evaporation.
LCMS (method B): Rt=7.48 min, m/z=446.05[M+H]$^+$; C$_{29}$H$_{23}$N$_3$O$_2$, Mono-isotopic mass=445.18
$^1$H NMR (400 MHz, D$_4$-methanol) δ 8.80 (d, J=2.7 Hz, 1H), 8.67 (d, J=5.7 Hz, 1H), 8.24 (ddd, J=8.8, 2.7, 1.1 Hz, 1H), 8.09 (dd, J=8.8, 5.7 Hz, 1H), 7.86 (d, J=9.2 Hz, 1H), 7.64 (dd, J=9.2, 2.6 Hz, 1H), 7.48 (m, 2H), 7.40 (m, 2H), 7.28 (m, 1H), 7.23 (m, 2H), 6.91 (m, 2H), 6.47 (d, J=2.6 Hz, 1H), 4.38 (t, J=9.5 Hz, 2H), 3.41 (t, J=9.5 Hz, 2H), 2.64 (s, 3H).

(p) 4-methyl-8-phenoxy-1-[2-(3-pyridyl)ethyl]-2,3-dihydro-1H-pyrrolo[3,2-d]quinoline hydrochloride Prepared using General Method 2 and Purification Method 1. The product was then converted to the hydrochloride salt by the addition of 1 N hydrochloric acid, followed by evaporation.
LCMS (method B): Rt=5.48 min, m/z=382.13[M+H]$^+$; C$_{25}$H$_{23}$N$_3$O, Mono-isotopic mass=381.18
$^1$H NMR (400 MHz, D$_4$-methanol) δ 8.78 (d, J=5.9 Hz, 1H), 8.75 (d, J=1.5 Hz, 1H), 8.32 (dt, J=8.1, 1.5 Hz, 1H), 8.02 (dd, J=8.1, 5.9 Hz, 1H), 7.86 (d, J=9.2 Hz, 1H), 7.66 (dd, J=9.2, 2.4 Hz, 1H), 7.56 (d, J=2.4 Hz, 1H), 7.41 (m, 2H), 7.15 (m, 3H), 4.12 (m, 4H), 3.25 (m, 4H), 2.55 (s, 3H).

(q) 4-methyl-8-phenoxy-1-(2-pyridylmethyl)-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.
LCMS (method B): Rt=6.72 min, m/z=368.10[M+H]$^+$; C$_{24}$H$_{21}$N$_3$O, Mono-isotopic mass=367.17
$^1$H NMR (400 MHz, D$_4$-methanol) δ 8.75 (dd, J=5.8, 1.2 Hz, 1H), 8.43 (m, 1H), 7.94 (m, 1H), 7.91 (d, J=9.2 Hz, 1H), 7.83 (d, J=8.0 Hz, 1H), 7.68 (dd, J=9.2, 2.5 Hz., 1H), 7.30 (m, 2H), 7.18 (m, 1H), 6.90 (m, 2H), 6.88 (d, J=2.5 Hz, 1H), 5.33 (s, 2H), 4.22 (t, J=9.5 Hz, 2H), 3.37 (t, J=9.5 Hz, 2H), 2.64 (s, 3H).

(r) 4-methyl-1-(5-methylpyrazin-2-ylmethyl)-8-phenoxy-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.
LCMS (method B): Rt=6.51 min, m/z=383.10[M+H]$^+$; C$_{24}$H$_{22}$N$_4$O, Mono-isotopic mass=382.18
$^1$H NMR (400 MHz, D$_4$-methanol) δ 8.50 (s, 1H), 8.43 (s, 1H), 7.83 (d, J=9.2 Hz, 1H), 7.62 (dd, J=9.2, 2.4 Hz, 1H), 7.30 (m, 3H), 7.15 (m, 1H), 6.92 (m, 2H), 5.13 (s, 2H), 4.20 (t, J=9.5 Hz, 2H), 3.29 (t, J=9.5 Hz, 2H), 2.62 (s, 3H), 2.57 (s, 3H).

(s) 8-chloro-4-methyl-1-(2-phenylethyl)-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.
LCMS (method B): Rt=7.55 min, m/z=323.05[M+H]$^+$; C$_{20}$H$_{19}$ClN$_2$, Mono-isotopic mass=322.12.
$^1$H NMR (400 MHz, D$_6$-DMSO) δ 14.02 (s, 1H), 8.01 (d, J=2.2 Hz, 1H), 7.98 (d, J=9.2 Hz, 1H), 7.88 (dd, J=9.2, 2.2 Hz, 1H), 7.31 (m, 4H), 7.20 (m, 1H), 4.15 (t, J=7.3 Hz, 2H), 4.08 (t, J=9.6 Hz, 2H), 3.10 (m, 4H), 2.49 (s, 3H).

(t) methyl 4-methyl-1-(2-phenylethyl)-2,3-dihydro-1H-pyrrolo[3,2-c]quinoline-8-carboxylate hydrochloride Prepared using General Method 2 and Purification Method 1. The product was then converted to the hydrochloride salt by the addition of 1 N hydrochloric acid, followed by evaporation.
LCMS (method B): Rt=7.17 min, m/z=347.08[M+H]$^+$; C$_{22}$H$_{22}$N$_2$O$_2$, Mono-isotopic mass=346.17
$^1$H NMR (400 MHz, D$_6$-DMSO) δ 14.09 (s, 1H), 8.78 (d, J=1.6 Hz, 1H), 8.29 (dd, J=8.9, 1.6 Hz, 1H), 8.05 (d, J=8.9 Hz, 1H), 7.45 (m, 2H), 7.36 (m, 2H), 7.25 (m, 1H), 4.19 (t, J=9.5 Hz, 2H), 4.12 (t, J=8.0 Hz, 2H), 3.95 (s, 3H), 3.16 (m, 4H), 2.52 (s, 3H).

(u) 4-methyl-8-(morpholin-1-yl)-1-(2-phenylethyl)-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.
LCMS (method B): Rt=7.26 min, m/z=374.14[M+H]$^+$; C$_{24}$H$_{27}$N$_3$O, Mono-isotopic mass=373.22
$^1$H NMR (400 MHz, D$_6$-DMSO) δ 13.66 (s, 1H), 7.85 (d, J=9.5 Hz, 1H), 7.73 (dd, J=9.5, 2.4 Hz, 1H), 7.32 (m, 4H), 7.24 (m, 1H), 7.19 (d, J=2.4 Hz, 1H), 4.16 (t, J=7.5 Hz, 2H), 4.00 (t, J=9.7 Hz, 2H), 3.75 (m, 4H), 3.12 (m, 8H), 2.47 (s, 3H).

(v) ethyl [4-methyl-1-(2-phenylethyl)-2,3-dihydro-1H-pyrrolo[3,2-c]quinoline-8-yl]acetate hydrochloride Prepared using General Method 2 and Purification Method 1. The product was then converted to the hydrochloride salt by the addition of 1 N hydrochloric acid, followed by evaporation.
LCMS (method B): Rt=7.57 min, m/z=375.08[M+H]$^+$; C$_{24}$H$_{26}$N$_2$O$_2$, Mono-isotopic mass=374.20
$^1$H NMR (400 MHz, D$_6$-DMSO) δ 13.67 (s, 1H), 8.05 (d, J=1.6 Hz, 1H), 7.88 (d, J=8.8 Hz, 1H), 7.76 (dd, J=8.8, 1.6 Hz, 1H), 7.34 (m, 2H), 7.29 (m, 2H), 7.21 (m, 1H), 4.16 (t, J=7.5 Hz, 2H), 4.11 (t, J=7.1 Hz, 2H), 4.03 (t, J=9.5 Hz, 2H), 3.89 (s, 2H), 3.09 (m, 4H), 2.48 (s, 3H), 1.19 (t, J=7.1 Hz, 3H).

(w) 1-[3-(4-methyl-8-phenoxy-2,3-dihydro-1H-pyrrolo[3,2-c]quinolin-1-yl)propyl]-pyrrolidin-2-one hydrochloride Prepared using General Method 2 and Purification Method 1. The product was then converted to the hydrochloride salt by the addition of 1 N hydrochloric acid, followed by evaporation.

LCMS (method B): Rt=6.58 min, m/z=402.11[M+H]$^+$; $C_{25}H_{27}N_3O_2$, Mono-isotopic mass=401.21

$^1$H NMR (400 MHz, D$_4$-methanol) δ 7.80 (d, J=9.3 Hz, 1H), 7.61 (dd, J=9.3, 2.5 Hz, 1H), 7.51 (d, J=2.5 Hz, 1H), 7.47 (m, 2H), 7.25 (m, 1H), 7.14 (m, 2H), 4.14 (t, J=9.6 Hz, 2H), 3.72 (t, J=7.8 Hz, 2H), 3.42 (t, J=7.1 Hz, 2H), 3.21 (m, 4H), 2.51 (s, 3H), 2.35 (t, J=8.1 Hz, 2H), 2.03 (m, 2H), 1.90 (m, 2H).

(x) 4-methyl-8-phenoxy-1-[2-(2-pyridyl)ethyl]-2,3-dihydro-1H-pyrrolo[3,2-d]quinoline hydrochloride Prepared using General Method 2 and Purification Method 1. The product was then converted to the hydrochloride salt by the addition of 1 N hydrochloric acid, followed by evaporation.

LCMS (method B): Rt=6.28 min, m/z=382.10[M+H]$^+$; $C_{25}H_{23}N_3O$, Mono-isotopic mass=381.18

$^1$H NMR (400 MHz, D$_4$-methanol) δ 8.78 (dd, J=5.9, 1.3 Hz, 1H), 8.54 (td, J=8.0, 1.3 Hz, 1H), 7.99 (m, 1H), 7.86 (d, J=9.4 Hz, 1H), 7.79 (d, J=8.0 Hz, 1H), 7.65 (dd, J=9.4, 2.5 Hz, 1H), 7.52 (d, J=2.5 Hz, 1H), 7.41 (m, 2H), 7.16 (m, 3H), 4.26 (t, J=7.3 Hz, 2H), 4.07 (t, J=9.6 Hz, 2H), 3.48 (t, J=7.3 Hz, 2H), 3.23 (t, J=9.6 Hz, 2H), 2.56 (s, 3H).

(y) ethyl 3-(8-methoxy-4-methyl-2,3-dihydro-1H-pyrrolo[3,2-c]quinoline-1-yl)propionate hydrochloride Prepared using General Method 2 and Purification Method 1. The product was then converted to the hydrochloride salt by the addition of 1 N hydrochloric acid, followed by evaporation.

LCMS (method B): Rt=6.21 min, m/z=315.07[M+H]$^+$; $C_{18}H_{22}N_2O_3$, Mono-isotopic mass=314.16

$^1$H NMR (400 MHz, D$_6$-DMSO) δ 13.77 (s, 1H), 7.91 (d, J=9.3 Hz, 1H), 7.57 (dd, J=9.3, 2.5 Hz, 1H), 7.50 (d, J=2.5 Hz, 1H), 4.19 (t, J=7.3 Hz, 2H), 4.09 (m, 4H), 3.91 (s, 3H), 3.12 (t, J=9.6 Hz, 2H), 2.91 (t, J=7.3 Hz, 2H), 2.48 (s, 3H), 1.17 (t, J=7.2 Hz, 3H).

(z) ethyl 4-(4-methyl-8-phenoxy-2,3-dihydro-1H-pyrrolo[3,2-c]quinoline-1-yl)butanoate hydrochloride Prepared using General Method 2 and Purification Method 1. The product was then converted to the hydrochloride salt by the addition of 1 N hydrochloric acid, followed by evaporation.

LCMS (method B): Rt=7.67 min, m/z=391.07[M+H]$^+$; $C_{24}H_{26}N_2O_3$, Mono-isotopic mass=390.19

$^1$H NMR (400 MHz, CD$_3$CN) δ 14.80 (s, 1H), 8.37 (d, J=9.3 Hz, 1H), 7.54 (dd, J=9.3, 2.5 Hz, 1H), 7.47 (d, J=2.5 Hz, 1H), 7.43 (m, 2H), 7.22 (m, 1H), 7.12 (m, 2H), 4.06 (q, J=7.1 Hz, 2H), 4.02 (t, J=9.6 Hz, 2H), 3.60 (m, 2H), 3.09 (t, J=9.6 Hz, 2H), 2.55 (s, 3H), 2.14 (t, J=7.3 Hz, 2H), 1.85 (m, 2H), 1.19 (t, J=7.1 Hz, 3H).

(aa) methyl 4-(4-methyl-8-phenoxy-2,3-dihydro-1H-pyrrolo[3,2-c]quinoline-1-yl)butanoate hydrochloride Prepared using General Method 2 and Purification Method 1. The product was then converted to the hydrochloride salt by the addition of 1 N hydrochloric acid, followed by evaporation.

LCMS (method B): Rt=7.26 min, m/z=377.08[M+H]$^+$; $C_{23}H_{24}N_2O_3$, Mono-isotopic mass=376.18

$^1$H NMR (400 MHz, D$_4$-methanol) δ 7.81 (d, J=9.3 Hz, 1H), 7.65 (dd, J=9.3, 2.5 Hz, 1H), 7.53 (d, J=2.5 Hz, 1H), 7.46 (m, 2H), 7.25 (m, 1H), 7.14 (m, 2H), 4.12 (t, J=9.6 Hz, 2H), 3.67 (m, 2H), 3.65 (s, 3H), 3.19 (t, J=9.6 Hz, 2H), 2.50 (s, 3H), 2.18 (t, J=7.2 Hz, 2H), 1.90 (m, 2H).

(ab) ethyl (4-methyl-8-phenoxy-2,3-dihydro-1H-pyrrolo[3,2-c]quinoline-1-yl)acetate hydrochloride Prepared using General Method 2 and Purification Method 1. The product was then converted to the hydrochloride salt by the addition of 1 N hydrochloric acid, followed by evaporation.

LCMS (method B): Rt=7.21 min, m/z=362.99[M+H]$^+$; $C_{22}H_{22}N_2O_3$, Mono-isotopic mass=362.16

$^1$H NMR (400 MHz, CD$_3$CN) δ 14.92 (s, 1H), 8.40 (d, J=9.3 Hz, 1H), 7.54 (dd, J=9.3, 2.5 Hz, 1H), 7.43 (m, 2H), 7.29 (d, J=2.5 Hz, 1H), 7.22 (m, 1H), 7.06 (m, 2H), 4.46 (s, 2H), 4.04 (m, 4H), 3.15 (t, J=9.6 Hz, 2H), 2.60 (s, 3H), 1.13 (t, J=7.0 Hz, 3H).

(ac) 4-methyl-1-(1-methylpiperidin-4-yl)-8-phenoxy-2,3-dihydro-1H-pyrrolo[3,2-c]quinoline dihydrochloride Prepared using General Method 2 and Purification Method 1. The product was then converted to the hydrochloride salt by the addition of 1 N hydrochloric acid, followed by evaporation.

LCMS (method B): Rt=4.68 min, m/z=374.14[M+H]$^+$; $C_{24}H_{27}N_3O$, Mono-isotopic mass=373.22

$^1$H NMR (400 MHz, D$_6$-DMSO) δ 14.04 (s, 1H), 11.05 (s, 1H), 8.06 (d, J=9.2 Hz, 1H), 7.67 (m, 2H), 7.49 (m, 2H), 7.26 (m, 1H), 7.15 (m, 2H), 4.63 (m, 1H), 4.01 (t, J=9.6 Hz, 2H), 3.43 (d, J=12.0 Hz, 2H), 3.14 (t, J=9.6 Hz, 2H), 2.85 (m, 2H), 2.69 (s, 3H), 2.52 (s, 3H), 2.31 (m, 2H), 2.00 (d, J=13.0 Hz, 2H).

(ad) 1-(1-benzylpyrrolidin-3-yl)-8-methoxy-4-methyl-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=4.54 min, m/z=374.16[M+H]$^+$; $C_{24}H_{27}N_3O$, Mono-isotopic mass=373.22

$^1$H NMR (400 MHz, D$_6$-DMSO+TFA-D) δ 7.90 (br d, J=9.0 Hz, 1H), 7.70-7.58 (m, 3H), 7.56-7.40 (m, 4H), 5.80-5.55 (m, 1H), 4.50 (2br s, 2H), 4.16 (m, 2H), 3.98 (2br s, 3H), 3.73 (m, 1H), 3.61 (m, 2H), 3.43 (m, 1H), 3.17 (m, 2H), 2.51 (s, 3H), 2.48 (m, 2H).

(ae) methyl 3-(4-methyl-8-phenoxy-2,3-dihydro-1H-pyrrolo[3,2-c]quinoline-1-yl)propionate hydrochloride Prepared using General Method 2 and Purification Method 1. The product was then converted to the hydrochloride salt by the addition of 1 N hydrochloric acid, followed by evaporation.

LCMS (method B): Rt=7.05 min, m/z=363.07[M+H]$^+$; $C_{22}H_{22}N_2O_3$, Mono-isotopic mass=362.16

$^1$H NMR (400 MHz, D$_4$-methanol) δ 7.83 (d, J=9.3 Hz, 1H), 7.65 (dd, J=9.3, 2.5 Hz, 1H), 7.54 (d, J=2.5 Hz, 1H), 7.45 (m, 2H), 7.24 (m, 1H), 7.14 (m, 2H), 4.13 (t, J=9.6 Hz, 2H), 3.97 (t, J=7.1 Hz, 2H), 3.65 (s, 3H), 3.18 (t, J=9.6 Hz, 2H), 2.66 (t, J=7.1 Hz, 2H), 2.52 (s, 3H).

(af) 1-((S)-indan-1-yl)-4-methyl-8-phenoxy-2,3-dihydro-1H-pyrrolo[3,2-c]quinoline Prepared using General Method 2 and Purification Method 3. The product was isolated as the acetate salt and then converted to the free base by partitioning between aqueous sodium carbonate and dichloromethane followed by evaporation of the organic phase.

LCMS (method B): Rt=8.81 min, m/z=393.06[M+H]$^+$; $C_{27}H_{24}N_2O$, Mono-isotopic mass=392.19

$^1$H NMR (400 MHz, CDCl$_3$) δ 7.97 (d, J=9.2 Hz, 1H), 7.64 (d, J=2.6 Hz, 1H), 7.31 (m, 3H), 7.24 (m, 2H), 7.16 (m, 2H), 7.08 (m, 1H), 7.02 (m, 2H), 5.88 (t, J=7.6 Hz, 1H), 3.46 (m, 2H), 3.00 (m, 3H), 2.85 (m, 1H), 2.52 (s, 3H), 2.32 (m, 1H), 2.11 (m, 1H).

(ag) 1-((R)-indan-1-yl)-4-methyl-8-phenoxy-2,3-dihydro-1H-pyrrolo[3,2-c]quinoline Prepared using General Method 2 and Purification Method 3. The product was isolated as the acetate salt and then converted to the free base by partitioning between aqueous sodium carbonate and dichloromethane followed by evaporation of the organic phase.

LCMS (method B): Rt=8.68 min, m/z=393.11[M+H]$^+$; $C_{27}H_{24}N_2O$, Mono-isotopic mass=392.19

$^1$H NMR (400 MHz, CDCl$_3$) δ 7.98 (d, J=9.2 Hz, 1H), 7.64 (d, J=2.6 Hz, 1H), 7.31 (m, 3H), 7.24 (m, 2H), 7.16 (m, 2H), 7.08 (m, 1H), 7.02 (m, 2H), 5.87 (t, J=7.6 Hz, 1H), 3.45 (m, 2H), 2.99 (m, 3H), 2.84 (m, 1H), 2.52 (s, 3H), 2.32 (m, 1H), 2.11 (m, 1H).

(ah) 1-(3-methoxypropyl)-4-methyl-8-phenoxy-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=7.31 min, m/z=349.13[M+H]$^+$; $C_{22}H_{24}N_2O_2$, Mono-isotopic mass=348.18

$^1$H NMR (400 MHz, D$_6$-DMSO) δ 13.76 (s, 1H), 8.00 (m, 1H), 7.68 (m, 2H), 7.46 (m, 2H), 7.23 (m, 1H), 7.12 (m, 2H), 4.06 (t, J=9.6 Hz, 2H), 3.73 (t, J=7.5 Hz, 2H), 3.22 (t, J=5.8 Hz, 2H), 3.14 (s, 3H), 3.13 (t, J=9.6 Hz, 2H), 2.49 (s, 3H), 1.82 (m, 2H).

(ai) 4-methyl-8-phenoxy-1-(tetrahydrofuran-2-ylmethyl)-2,3-dihydro-1H-pyrrolo[3,2-d]quinoline hydrochloride Prepared using General Method 2 and Purification Method 1. The product was then converted to the hydrochloride salt by the addition of 1 N hydrochloric acid, followed by evaporation.

LCMS (method B): Rt=7.35 min, m/z=361.12[M+H]$^+$; $C_{23}H_{24}N_2O_2$, Mono-isotopic mass=360.16

$^1$H NMR (400 MHz, D$_6$-DMSO) δ 13.83 (s, 1H), 8.01 (d, J=9.2 Hz, 1H), 7.71 (dd, J=9.2, 2.5 Hz, 1H), 7.68 (d, J=2.5 Hz, 1H), 7.48 (m, 2H), 7.25 (m, 1H), 7.16 (m, 2H), 4.15 (td, J=11.3, 7.9 Hz, 1H), 4.03 (m, 2H), 3.73 (d, J=6.0 Hz, 2H), 3.52 (t, J=6.7 Hz, 2H), 3.13 (m, 2H), 2.50 (s, 3H), 1.74 (m, 3H), 1.27 (m, 1H).

(aj) 1-[2-(4-chlorophenyl)ethyl]-4-methyl-8-phenoxy-2,3-dihydro-1H-pyrrolo[3,2-d]quinoline hydrochloride Prepared using General Method 2 and Purification Method 1. The product was then converted to the hydrochloride salt by the addition of 1 N hydrochloric acid, followed by evaporation.

LCMS (method B): Rt=8.91 min, m/z=415.08[M+H]$^+$; $C_{26}H_{23}ClN_2O$, Mono-isotopic mass=414.15.

$^1$H NMR (400 MHz, D$_6$-DMSO) δ 13.82 (2s, 1H), 8.01 (m, 1H), 7.68 (dd, J=9.2, 2.5 Hz, 1H), 7.54 (d, J=2.5 Hz, 1H), 7.45 (m, 2H), 7.26 (m, 2H), 7.21 (m, 1H), 7.14 (m, 2H), 7.06 (m, 2H), 3.98 (t, J=9.6 Hz, 2H), 3.92 (t, J=7.5 Hz, 2H), 3.10 (t, J=9.6 Hz, 2H), 2.90 (t, J=7.5 Hz, 2H), 2.50 (s, 3H).

(ak) 1-[2-(4-methoxyphenyl)ethyl]-4-methyl-8-phenoxy-2,3-dihydro-1H-pyrrolo[3,2-d]quinoline hydrochloride Prepared using General Method 2 and Purification Method 1. The product was then converted to the hydrochloride salt by the addition of 1 N hydrochloric acid, followed by evaporation.

LCMS (method B): Rt=8.44 min, m/z=411.12[M+H]$^+$; $C_{27}H_{26}N_2O_2$, Mono-isotopic mass=410.20

$^1$H NMR (400 MHz, D$_6$-DMSO) δ 13.67 (s, 1H), 7.97 (d, J=9.3 Hz, 1H), 7.69 (dd, J=9.3, 2.5 Hz, 1H), 7.56 (d, J=2.5 Hz, 1H), 7.46 (m, 2H), 7.23 (m, 1H), 7.15 (m, 2H), 6.93 (m, 2H), 6.76 (m, 2H), 3.97 (t, J=9.6 Hz, 2H), 3.87 (t, J=7.4 Hz, 2H), 3.69 (s, 3H), 3.09 (t, J=9.6 Hz, 2H), 2.83 (t, J=7.4 Hz, 2H), 2.49 (s, 3H).

(al) 4-methyl-8-phenoxy-1-(2-phenylpropyl)-2,3-dihydro-1H-pyrrolo[3,2-d]quinoline hydrochloride Prepared using General Method 2 and Purification Method 1. The product was then converted to the hydrochloride salt by the addition of 1 N hydrochloric acid, followed by evaporation.

LCMS (method B): Rt=8.72 min, m/z=395.11[M+H]$^+$; $C_{27}H_{26}N_2O$, Mono-isotopic mass=394.20

$^1$H NMR (400 MHz, D$_6$-DMSO) δ 13.81 (s, 1H), 8.01 (d, J=9.3 Hz, 1H), 7.73 (dd, J=9.3, 2.5 Hz, 1H), 7.51 (m, 2H), 7.44 (d, J=2.5 Hz, 1H), 7.28 (m, 1H), 7.22 (m, 5H), 7.09 (m, 2H), 3.92 (m, 2H), 3.67 (dd, J=15.0, 9.4 Hz, 1H), 3.38 (m, 1H), 3.04 (m, 2H), 2.88 (m, 1H), 2.46 (s, 3H), 1.04 (d, J=7.0 Hz, 3H).

(am) 8-cyano-4-methyl-1-(2-phenylethyl)-2,3-di-hydro-1H-pyrrolo[3,2-d]quinoline hydrochloride Prepared using General Method 2 and Purification Method 1. The product was then converted to the hydrochloride salt by the addition of 1 N hydrochloric acid, followed by evaporation.

LCMS (method B): Rt=6.59 min, m/z=314.12[M+H]$^+$; $C_{21}H_{19}N_3$, Mono-isotopic mass=313.16

$^1$H NMR (400 MHz, $D_6$-DMSO) δ 14.21 (s, 1H), 8.45 (d, J=1.6 Hz, 1H), 8.11 (dd, J=8.9, 1.6 Hz, 1H), 8.05 (d, J=8.9 Hz, 1H), 7.34 (m, 2H), 7.26 (m, 2H), 7.17 (m, 1H), 4.25 (t, J=7.1 Hz, 2H), 4.10 (t, J=9.6 Hz, 2H), 3.12 (m, 4H), 2.50 (s, 3H).

(an) 8-hydroxy-4-methyl-1-(2-phenylethyl)-2,3-dihydro-1H-pyrrolo[3,2-c]quinoline hydrochloride Prepared using General Method 2 and Purification Method 1. The product was then converted to the hydrochloride salt by the addition of 1 N hydrochloric acid, followed by evaporation.

LCMS (method B): Rt=6.75 min, m/z=305.11[M+H]$^+$; $C_{20}H_{20}N_2O$, Mono-isotopic mass=304.16

$^1$H NMR (400 MHz, $D_6$-DMSO) δ 13.51 (s, 1H), 10.44 (s, 1H), 7.82 (d, J=9.2 Hz, 1H), 7.57 (d, J=2.3 Hz, 1H), 7.44 (dd, J=9.2, 2.3 Hz, 1H), 7.33 (m, 4H), 7.24 (m, 1H), 4.07 (t, J=7.4 Hz, 2H), 3.90 (t, J=9.6 Hz, 2H), 3.08 (t, J=7.4 Hz, 2H), 3.04 (t, J=9.6 Hz, 2H), 2.45 (s, 3H).

(ao) 8-phenoxy-1-(2-phenylethyl)-2,3-dihydro-1H-pyrrolo[3,2-c]quinoline hydrochloride Prepared using General Method 3 and Purification Method 4. The product was then converted to the hydrochloride salt by the addition of 1 N hydrochloric acid, followed by evaporation.

LCMS (method B): Rt=8.52 min, m/z=367.08[M+H]$^+$; $C_{25}H_{22}N_2O$, Mono-isotopic mass=366.17

$^1$H NMR (400 MHz, $D_6$-DMSO) δ 13.79 (s, 1H), 8.26 (s, 1H), 7.98 (d, J=9.3 Hz, 1H), 7.72 (dd, J=9.3, 2.5 Hz, 1H), 7.60 (d, J=2.5 Hz, 1H), 7.46 (m, 2H), 7.19 (m, 6H), 7.03 (m, 2H), 3.99 (t, J=9.5 Hz, 2H), 3.94 (t, J=7.6 Hz, 2H), 3.16 (t, J=9.5 Hz, 2H), 2.91 (t, J=7.6 Hz, 2H).

Example 5

6,8-Dimethoxy-1-(4-hydroxyphenyl)-4-methylpyrrolo[3,2-c]quinoline trifluoroacetate A mixture of 6,8-dimethoxy-1-(4-hydroxyphenyl)-4-methyl-2,3-dihydro-1H-pyrrolo[3,2-c]quinoline (0.1 g; see Example 3(i) above), palladium on carbon (10%, 0.1 g) and diphenyl ether (5 mL) was heated at 200° C. for 2 hours. The mixture was cooled to room temperature, diluted with methanol and filtered through Celite™. The filtrate was evaporated to dryness and the residue was purified using Purification Method 1 to give the title compound (0.004 g).

LCMS (Method B): Rt=6.50 min, m/z=335.13 [M+H]$^+$; $C_{20}H_{18}N_2O_3$, Mono-isotopic mass=334.13

$^1$H-NMR (400 MHz, $D_6$-DMSO): δ 10.24 (s, br, 1H), 7.92 (d, J=3.3 Hz, 1H), 7.45 (m, 2H), 7.44 (d, J=3.3 Hz, 1H), 7.08 (d, J=2.4 Hz, 1H), 7.06 (m, 2H), 6.25 (d, J=2.4 Hz, 1H), 4.13 (s, 3H), 3.52 (s, 3H), 3.15 (s, 3H).

Example 6

8-Methoxy-4-methyl-1-[4-(4-methylpiperazin-1-yl)-3-fluorophenyl]-2,3-dihydro-1H-pyrrolo[3,2-c]quinoline hydrochloride (i) 1-(4-Bromo-3-fluorophenyl)-8-methoxy-4-methyl-2,3-dihydro-1H-pyrrolo[3,2-c]quinoline The sub-title compound was prepared from the appropriate intermediates by analogy with General Method 3 (above) and was purified using Purification Method 1.

$^1$H NMR (400 Mz, $D_4$-methanol) δ 7.86 (t, J=8.1 Hz, 1H), 7.77 (d, J=9.3 Hz, 1H), 7.51 (dd, J=9.2, 2.4 Hz, 1H), 7.47 (dd, J=9.3, 2.7 Hz, 1H), 7.31 (m, 1H), 6.42 (d, J=2.7 Hz, 1H), 4.45 (t, J=9.3 Hz, 2H), 3.47 (s, 3H), 3.42 (t, J=9.3 Hz, 2H), 2.64 (s, 3H).

The compound was converted to the free base by partitioning between dichloromethane and aqueous sodium bicarbonate solution, followed by evaporation of the organic phase. The free base was used directly without further purification.

(ii) 8-Methoxy-4-methyl-1-[4-(4-methylpiperazin-1-yl)-3-fluorophenyl]-2,3-dihydro-1H-pyrrolo[3,2-c]quinoline hydrochloride A mixture of 1-(4-bromo-3-fluorophenyl)-8-methoxy-4-methyl-2,3-dihydro-1H-pyrrolo[3,2-c]quinoline (0.075 g; see step (i) above), 1-methylpiperazine (0.023 g), palladium acetate (0.003 g), 2-(di-tert-butylphosphino)biphenyl (0.003 g), sodium tert-butoxide (0.026 g) and toluene (5 mL) was stirred and heated at 80° C. under an atmosphere of nitrogen overnight. The mixture was then stirred and heated at reflux overnight. Further palladium acetate (0.003 g) and 2-(di-tert-butylphosphino)biphenyl (0.003 g) was added and the mixture was stirred and heated at reflux overnight. The mixture was evaporated to dryness and the residue was partitioned between ethyl acetate and aqueous sodium bicarbonate solution. The organic layer was washed with water, aqueous brine solution, dried (MgSO$_4$) and filtered. The filtrate was evaporated to dryness and the residue was purified using Purification Method 1. The product was then converted to the hydrochloride salt by the addition of 1 N hydrochloric acid, followed by evaporation to give the title compound (0.009 g).

LCMS (Method B): Rt=4.79 min, m/z=407.17 [M+H]$^+$; $C_{24}H_{27}FN_4O$, Mono-isotopic mass=406.22

$^1$H-NMR (400 MHz, $D_4$-methanol): δ 7.75 (d, J=9.2 Hz, 1H), 7.45 (dd, J=9.2, 2.7 Hz, 1H), 7.42 (dd, J=12.9, 2.3 Hz, 1H), 7.37 (dd, J=8.4, 2.3 Hz, 1H), 7.34 (t, J=8.4 Hz, 1H), 6.45 (d, J=2.7 Hz, 1H), 4.40 (t, J=9.5 Hz, 2H), 3.68 (s, br, 4H), 3.45 (s, 3H), 3.40 (t, J=9.5 Hz, 2H), 3.40, 3.25 (broad singlets, 4H), 3.00 (s, 3H), 2.62 (s, 3H).

Example 7

4-Methyl-8-phenylamino-1-(2-phenylethyl)-2,3-dihydro-1H-pyrrolo[3,2-c]quinoline formate (i) 8-Bromo-4-methyl-1-(2-phenylethyl)-2,3-dihydro-1H-pyrrolo[3,2-c]quinoline The sub-title compound was prepared from the appropriate intermediates by analogy with General Method 3 (above) and then used without purification.

LCMS (method A): Rt=2.42 min, m/z=367 [M+H]$^+$; C$_{20}$H$_{19}$BrN$_2$, Mono-isotopic mass=367.07

(ii) 4-Methyl-8-phenylamino-1-(2-phenylethyl)-2,3-dihydro-1H-pyrrolo[3,2-c]quinoline formate A mixture of 8-bromo-4-methyl-1-(2-phenylethyl)-2,3-dihydro-1H-pyrrolo[3,2-c]quinoline (0.308 g; see step (i) above), aniline (0.064 mL) 2-dicyclohexyl-phosphino 2'-dimethylamino biphenyl (0.028 g), tris-(dibenzylideneacetone)-dipalladium (0.032 g), sodium tert-butoxide (0.094 g) and toluene (8 mL) was degassed and then heated in the microwave at 140° C. for 30 minutes. The mixture was diluted with water, extracted with ethyl acetate, washed with water, dried (MgSO$_4$) and filtered. The filtrate was evaporated to dryness and the residue was purified using Purification Method 1 to give the title compound (0.08 g).

LCMS (method B): Rt=8.61 min, m/z=380.12[M+H]$^+$; C$_{26}$H$_{25}$N$_3$, Mono-isotopic mass=379.20

$^1$H NMR (400 MHz, D$_6$-DMSO) δ 8.40 (s, 1H), 8.27 (s, 1H), 7.70 (d, J=9.2 Hz, 1H), 7.66 (d, J=2.4 Hz, 1H), 7.35 (dd, J=9.2, 2.4 Hz, 1H), 7.23 (m, 2H), 7.17 (m, 5H), 7.06 (m, 2H), 6.87 (m, 1H), 3.73 (m, 4H), 3.00 (t, J=9.4 Hz, 2H), 2.88 (t, J=7.8 Hz, 2H), 2.38 (s, 3H).

Example 8

[4-Methyl-1-(2-phenylethyl)-2,3-dihydro-1H-pyrrolo[2,3-c]quinoline-8-oyl]piperidine hydrochloride (i) 4-Methyl-1-(2-phenylethyl)-2,3-dihydro-1H-pyrrolo[3,2-c]quinoline-8-carboxylic acid Crude methyl 4-methyl-1-(2-phenylethyl)-2,3-dihydro-1H-pyrrolo[3,2-c]quinoline-8-carboxylate (see Example 4 (t) above) was dissolved in a mixture of methanol (3 mL) and water (3 mL) and sodium hydroxide (0.2 g) was added and the mixture was stirred at room temperature for 1 hour. The mixture was evaporated to dryness and the residue was dissolved in ethyl acetate and washed with aqueous citric acid solution, dried (MgSO$_4$) and filtered. The filtrate was evaporated to dryness and the residue was purified using Purification Method 1. The product (sub-title compound) was used directly without further purification.

(ii) [4-Methyl-1-(2-phenylethyl)-2,3-dihydro-1H-pyrrolo[2,3-c]quinoline-8-oyl]piperidine hydrochloride A mixture of crude 4-methyl-1-(2-phenylethyl)-2,3-dihydro-1H-pyrrolo[3,2-c]quinoline-8-carboxylic acid (0.05 g; see step (i) above), piperidine (0.085 g), ethyl acetate (2 mL), pyridine (0.2 mL) and O-(7-azabenzotriazol-1-yl)-N,N,N',N'-tetramethyluronium hexafluorophosphate (0.051 g) was stirred at room temperature for 2 hours. The resultant mixture was evaporated to dryness and the residue was purified by Purification Method 1. The product was then converted to the hydrochloride salt by the addition of 1 N hydrochloric acid, followed by evaporation to give the title compound (0.023 g).

LCMS (method B): Rt=7.06 min, m/z=400.14[M+H]$^+$; C$_{26}$H$_{29}$N$_3$O, Mono-isotopic mass=399.23

$^1$H NMR (400 MHz, D$_6$-DMSO) δ 13.88 (s, 1H), 8.08 (d, J=1.5 Hz, 1H), 7.99 (d, J=8.8 Hz, 1H), 7.85 (dd, J=8.8, 1.5 Hz, 1H), 7.32 (m, 4H), 7.23 (m, 1H), 4.13 (t, J=7.7 Hz, 2H), 4.07 (t, J=9.5 Hz, 2H), 3.59 (br, 2H), 3.31 (br, 2H), 3.12 (m, 4H), 2.51 (s, 3H), 1.50 (br m, 6H).

Example 9

4-Methyl-1-(2-phenylethyl)-8-phenoxy-2,3-dihydro-1H-pyrrolo[3,2-c]quinoline hydrochloride Large Scale Process Outline.

| Step No. | Operation | Charges |
|---|---|---|
| 1 | Set-up 10 L flange flask and purge with N$_2$. | |
| 2 | Charge to flask stage 4-chloro-3-(2-chloroethyl)-2-methyl-6-phenoxyquinoline (1 eq.; see Preparation 4 above). | 745.3 g |
| 3 | Charge to flask ethylene glycol (5 volumes). | 3700 mL |
| 4 | Nitrogen was bubbled through the reaction mixture for 30 min. | |
| 5 | Phenethylamine (2.0 eq) was added and the flask evacuated and purged with N$_2$ 3x. | 560 mL |
| 6 | The reaction mixture was heated to 180° C. under an atmosphere of N$_2$. | |
| 7 | The reaction was analysed for completion after 2 h by LC analysis and every hour thereafter until reaction complete. The reaction was deemed complete when the level of reaction intermediate at rt 16.8 min <1% . | |
| 8 | The reaction mixture was allowed to cool to room temperature and left to stir overnight. | |
| 9 | Water (5 volumes) was added to the reaction mixture. | 3700 mL |
| 10 | The reaction mixture was acidified to pH 1 using conc. HCl. | ~10 mL |
| 11 | The mixture was extracted using DCM (2 × 5 volumes). | 2 × 3700 mL |
| 12 | The DCM extracts were combined and washed with water (5 volumes). | 3700 mL |
| 13 | The DCM extracts were dried over MgSO$_4$. | |
| 14 | The DCM mixture was distilled under atmospheric pressure until precipitate starts to form. | |
| 15 | Acetone (6 volumes) was added and the remaining amount of DCM removed by distillation until a constant head temperature was reached. Add further amount of acetone to increase mobility of slurry if required. | 4500 mL |
| 16 | The mixture was allowed to cool to room temperature and stirred for 1 h. | |
| 17 | The precipitate was filtered and the solid cake washed with acetone (2 volumes). | 1500 mL |
| 18 | The crude stage 3 was dissolved in EtOH (4 volumes) at reflux. | 3000 mL |
| 19 | The mixture was allowed to cool to 70° C. and a polish and filter carried out transferring to mixture to a 10 L flange flask. | |
| 20 | The filtered mixture was allowed to cool to room temperature resulting in the formation of a precipitate. The precipitate was filtered and the wet cake washed with acetone (2 volumes). A further recrystallisation can be used to improve purity. | 1500 mL |
| 21 | The title compound was dried in a vacuum oven to constant weight at 50° C. | |

Example 10

Compounds of Examples 1 to 8 above may be formulated for topical administration according to any of the following formulations (wherein "active compound" represents any of the compounds of Examples 1 to 8 above).

| Excipient (w/w) | Formulation | | | | | | | |
|---|---|---|---|---|---|---|---|---|
| | A(i) | A(ii) | B(i) | B(ii) | C(i) | C(ii) | D | E |
| Benzyl alcohol | 1.0 | 1.0 | 1.0 | 1.0 | — | — | 2.0 | 2.1 |
| Potassium sorbate | — | — | — | — | 0.04 | 0.1 | — | — |
| EDTA | — | — | — | — | 0.04 | 0.1 | — | — |
| Ethanol | 9.9 | 10 | 7.7 | 7.7 | — | — | 10.2 | 10 |
| Propylene glycol | 15.2 | 15 | 5.7 | 5.7 | — | — | 15.0 | 14.9 |
| Glycerol | — | — | 25.1 | 25 | — | — | — | 10.2 |
| Kleptose ™ | — | — | — | — | 20.1 | 20 | — | — |
| Klucel ™ | — | — | — | — | 2.0 | 2.0 | — | — |
| HEC | 2 | 2 | 2.2 | 2.0 | — | — | 2 | 2.0 |
| Water | — | — | — | — | 75.82 | 75.8 | 68.8 | 58.8 |
| Citrate/phosphate pH 5.5 buffer | 69.8 | 70 | 56.3 | 56.6 | — | — | — | — |
| Active compound | 2.0 | 2.0 | 2.0 | 2.0 | 2.0 | 2.0 | 2.0 | 2.0 |

Alternative formulations include those based upon B(i) and B(ii) above, but having increased propylene glycol concentration (but less than 15% w/w) and decreased glycerol concentration.

Example 11

Compounds of Examples 1 to 8 above were found to possess activity in biological tests described above. Biological activity that was determined included a log kill, at 25, 10 or 5 μg/mL of test compound, of above 0.5 (e.g. from 0.5 to 7) against stationary phase and/or persister bacteria of the types *E. coli*, *Enterococcus*, *Staph. aureus*, *Streptococcus* and *Mycobacterium tuberculosis*.

Indeed, the following compounds had the activity indicated.

(a) The compound of Example 1(a), when tested against *Staph. aureus* stationary phase bacteria at 5 μg/mL of test compound, displayed a log kill of 3.55.

(c) The compound of Example 1(h), when tested against *E. coli* persister bacteria at 25 μg/mL of test compound, displayed a log kill of 3.83.

Abbreviations br=broad (in relation to NMR)
d=doublet (in relation to NMR)
DCM=dichloromethane
DMSO=dimethylsulfoxide
EDTA=ethylenediaminetetraacetic acid
HEC=hydroxyethylcellulose
HPLC=high performance liquid chromatography
LC=liquid chromatography
m=multiplet (in relation to NMR)
MBC=minimum bactericidal concentration
Me=methyl
min.=minute(s)
MIC=minimum inhibitory concentration
MS=mass spectroscopy
NMR=nuclear magnetic resonance
q=quartet (in relation to NMR)
s=singlet (in relation to NMR)
t=triplet (in relation to NMR)

Prefixes n-, s-, i-, t- and tert- have their usual meanings normal, secondary, iso, and tertiary.

The invention claimed is:

1. A method of killing clinically latent bacterial microorganisms in a mammal comprising administering a compound to a mammal in need thereof, wherein the compound is selected from the consisting of:

(1) 6,8-dimethoxy-4-methyl-1-(3-phenoxyphenyl)-2,3-dihydro-1H-pyrrolo[3,2-c]-quinoline;
(2) 6,8-dimethoxy-4-methyl-1-(2-phenoxyethyl)-2,3-dihydro-1H-pyrrolo[3,2-c]-quinoline;
(3) 1-cyclopropyl-6,8-dimethoxy-4-methyl-2,3-dihydro-1H-pyrrolo[3,2-c]-quinoline;
(4) 8-methoxy-4-methyl-1-(4-phenoxyphenyl)-2,3-dihydro-1H-pyrrolo[3,2-c]-quinoline;
(5) {2-[4-(8-methoxy-4-methyl-2,3-dihydro-1H-pyrrolo[3,2-c]quinolin-1-yl)-phenyoxy]ethyl}dimethylamine;
(6) 8-methoxy-4-methyl-1-[4-(pyridin-3-yloxy)phenyl]-2,3-dihydro-1H-pyrrolo[3,2-c]quinoline;
(7) 4-methyl-8-phenoxy-1-phenyl-2,3-dihydro-1H-pyrrolo[3,2-c]quinoline;
(8) 1-benzyl-4-methyl-8-phenoxy-2,3-dihydro-1H-pyrrolo[3,2-c]quinoline;
(9) 1-(indan-2-yl)-4-methyl-8-phenoxy-2,3-dihydro-1H-pyrrolo[3,2-c]quinoline;
(10) 4-methyl-6-phenoxy-1-phenyl-2,3-dihydro-1H-pyrrolo[3,2-c]quinoline;
(11) 1-benzyl-4-methyl-6-phenoxy-2,3-dihydro-1H-pyrrolo[3,2-c]quinoline;
(12) 1-(indan-2-yl)-4-methyl-6-phenoxy-2,3-dihydro-1H-pyrrolo[3,2-c]quinoline;
(13) 4-methyl-1-(2-phenylethyl)-8-phenoxy-2,3-dihydro-1H-pyrrolo[3,2-c]quinoline;
(14) 8-methoxy-4-methyl-1-(2-phenylethyl)-2,3-dihydro-1H-pyrrolo[3,2-c]-quinolin-6-ol;
(15) 1-(1-benzyl-piperidin-4-yl)-4-methyl-8-phenoxy-2,3-dihydro-1H-pyrrolo[3,2-c]quinoline;
(16) 1-(indan-1-yl)-4-methyl-8-phenoxy-2,3-dihydro-1H-pyrrolo[3,2-c]quinoline;
(17) 1-(benzodioxan-2-ylmethyl)-4-methyl-8-phenoxy-2,3-dihydro-1H-pyrrolo[3,2-c]quinoline;
(18) 4-methyl-8-phenoxy-1-(1,2,3,4-tetrahydronaphthalen-1-yl)-2,3-dihydro-1H-pyrrolo[3,2-c]quinoline;
(19) 1-cyclohexyl-4-methyl-8-phenoxy-2,3-dihydro-1H-pyrrolo[3,2-c]quinoline;
(20) 8-ethoxy-4-methyl-1-(4-phenoxyphenyl)-2,3-dihydro-1H-pyrrolo[3,2-c]-quinoline;
(21) 1-(4-methoxyphenyl)-4-methyl-8-phenoxy-2,3-dihydro-1H-pyrrolo[3,2-c]-quinoline;
(22) 4-methyl-1-(2-methylphenyl)methyl-8-phenoxy-2,3-dihydro-1H-pyrrolo[3,2-c]-quinoline;
(23) 4-methyl-8-phenoxy-1-(4-iso-propylphenyl)-2,3-dihydro-1H-pyrrolo[3,2-c]quinoline;
(24) 4-methyl-8-phenoxy-1-(1-phenylethyl)-2,3-dihydro-1H-pyrrolo[3,2-c]-quinoline;
(25) 8-methoxy-4-methyl-1-(2-phenylethyl)-2,3-dihydro-1H-pyrrolo[3,2-c]-quinoline;
(26) 6,8-dimethoxy-1-(4-hydroxyphenyl)-4-methyl-2,3-dihydro-1H-pyrrolo[3,2-c]quinoline;
(27) 6,8-dimethoxy-1-(3-hydroxyphenyl)-4-methyl-2,3-dihydro-1H-pyrrolo[3,2-c]quinoline;
(28) 6,8-dimethoxy-1-(3-hydroxy-5-methylphenyl)-4-methyl-2,3-dihydro-1H-pyrrolo[3,2-c]quinoline;
(30) 8-methoxy-1-(4-methoxyphenyl)-4-methyl-2,3-dihydro-1H-pyrrolo[3,2-c]-quinoline;
(31) 8-trifluoromethoxy-1-(4-phenoxyphenyl)-4-methyl-2,3-dihydro-1H-pyrrolo[3,2-c]quinoline;
(32) 6,8-dimethoxy-4-methyl-1-[4-(pyridin-3-yloxy)phenyl]-2,3-dihydro-1H-pyrrolo[3,2-c]quinoline;

(33) 1-benzyl-6,8-dimethoxy-4-methyl-2,3-dihydro-1H-pyrrolo[3,2-c]quinoline;
(34) 6,8-dimethoxy-4-methyl-1-(2-phenylethyl)-2,3-dihydro-1H-pyrrolo[3,2-c]quinoline;
(35) 4-methyl-1-(2-phenylethyl)-8-trifluoromethoxy-2,3-dihydro-1H-pyrrolo[3,2-c]quinoline;
(36) 6,8-dimethoxy-1-(indan-1-yl)-4-methyl-2,3-dihydro-1H-pyrrolo[3,2-c]quinoline;
(37) 6,8-dimethoxy-4-methyl-1-[(6-phenoxy)pyridin-3-yl]-2,3-dihydro-1H-pyrrolo[3,2-c]quinoline;
(38) 6,8-dimethoxy-1-[(6-methoxy)pyridin-3-yl]-4-methyl-2,3-dihydro-1H-pyrrolo[3,2-c]quinoline;
(39) 1-(benzodioxol-5-ylmethyl)-6,8-dimethoxy-4-methyl-2,3-dihydro-1H-pyrrolo[3,2-c]quinoline;
(40) 6,8-dimethoxy-4-methyl-1-(3-methylbutyl)-2,3-dihydro-1H-pyrrolo[3,2-c]quinoline;
(41) 1-cyclopropylmethyl-6,8-dimethoxy-4-methyl-2,3-dihydro-1H-pyrrolo[3,2-c]quinoline;
(43) 8-methoxy-4-methyl-1-(1,2,3,4-tetrahydronaphthalen-1-yl)-2,3-dihydro-1H-pyrrolo[3,2-c]quinoline;
(49) 1-{4-[2-(N,N-dimethylamino)ethoxy]phenyl}-4-methyl-8-phenoxy-2,3-dihydro-1H-pyrrolo[3,2-c]quinoline;
(50) 1-[4-(4-fluorophenoxy)phenyl]-8-methoxy-4-methyl-2,3-dihydro-1H-pyrrolo[3,2-c]quinoline;
(51) 1-(benzodioxan-2-ylmethyl)-8-methoxy-4-methyl-2,3-dihydro-1H-pyrrolo[3,2-c]quinoline;
(52) 1-cyclohexyl-8-methoxy-4-methyl-2,3-dihydro-1H-pyrrolo[3,2-c]quinoline;
(53) 8-methoxy-4-methyl-1-phenyl-2,3-dihydro-1H-pyrrolo[3,2-c]quinoline;
(54) 4-methyl-8-phenoxy-1-[4-(3-pyridyl)phenyl]-2,3-dihydro-1H-pyrrolo[3,2-c]-quinoline;
(55) 4-methyl-8-phenoxy-1-[2-(3-pyridyl)ethyl]-2,3-dihydro-1H-pyrrolo[3,2-c]-quinoline;
(56) 4-methyl-8-phenoxy-1-(2-pyridylmethyl)-2,3-dihydro-1H-pyrrolo[3,2-c]-quinoline;
(57) 4-methyl-1-(5-methylpyrazin-2-ylmethyl)-8-phenoxy-2,3-dihydro-1H-pyrrolo[3,2-c]quinoline;
(62) 1-[3-(4-methyl-8-phenoxy-2,3-dihydro-1H-pyrrolo[3,2-c]quinolin-1-yl)propyl]-pyrrolidin-2-one;
(63) 4-methyl-8-phenoxy-1-[2-(2-pyridyl)ethyl]-2,3-dihydro-1H-pyrrolo[3,2-c]-quinoline;
(64) ethyl 3-(8-methoxy-4-methyl-2,3-dihydro-1H-pyrrolo[3,2-c]quinoline-1-yl)propionate;
(65) ethyl 4-(4-methyl-8-phenoxy-2,3-dihydro-1H-pyrrolo[3,2-c]quinoline-1-yl)butanoate;
(66) methyl 4-(4-methyl-8-phenoxy-2,3-dihydro-1H-pyrrolo[3,2-c]quinoline-1-yl)butanoate;
(67) ethyl (4-methyl-8-phenoxy-2,3-dihydro-1H-pyrrolo[3,2-c]quinoline-1-yl)acetate;
(68) 4-methyl-1-(1-methylpiperidin-4-yl)-8-phenoxy-2,3-dihydro-1H-pyrrolo[3,2-c]quinoline;
(69) 1-(1-benzylpyrrolidin-3-yl)-8-methoxy-4-methyl-2,3-dihydro-1H-pyrrolo[3,2-c]quinoline;
(70) methyl 3-(4-methyl-8-phenoxy-2,3-dihydro-1H-pyrrolo[3,2-c]quinoline-1-yl)propionate;
(71) 1-((S)-indan-1-yl)-4-methyl-8-phenoxy-2,3-dihydro-1H-pyrrolo[3,2-c]-quinoline;
(72) 1-((R)-indan-1-yl)-4-methyl-8-phenoxy-2,3-dihydro-1H-pyrrolo[3,2-c]-quinoline;
(73) 1-(3-methoxypropyl)-4-methyl-8-phenoxy-2,3-dihydro-1H-pyrrolo[3,2-c]-quinoline;
(74) 4-methyl-8-phenoxy-1-(tetrahydrofuran-2-ylmethyl)-2,3-dihydro-1H-pyrrolo[3,2-c]quinoline;
(75) 1-[2-(4-chlorophenyl)ethyl]-4-methyl-8-phenoxy-2,3-dihydro-1H-pyrrolo[3,2-c]quinoline;
(76) 1-[2-(4-methoxyphenyl)ethyl]-4-methyl-8-phenoxy-2,3-dihydro-1H-pyrrolo[3,2-c]quinoline;
(77) 4-methyl-8-phenoxy-1-(2-phenylpropyl)-2,3-dihydro-1H-pyrrolo[3,2-c]-quinoline;
(80) 8-phenoxy-1-(2-phenylethyl)-2,3-dihydro-1H-pyrrolo[3,2-c]quinoline;
(82) 8-methoxy-4-methyl-1-[4-(4-methylpiperazin-1-yl)-3-fluorophenyl]-2,3-dihydro-1H-pyrrolo[3,2-c]quinoline;
(83) 4-methyl-8-phenylamino-1-(2-phenylethyl)-2,3-dihydro-1H-pyrrolo[3,2-c]-quinoline; or a pharmaceutically-acceptable salt thereof, and
wherein the clinically latent microorganisms are associated with a bacterial infection.

2. A method of treating a microbial infection in a mammal, comprising administering to a mammal in need thereof an effective amount of a compound, wherein the compound is selected from the group consisting of:
(1) 6,8-dimethoxy-4-methyl-1-(3-phenoxyphenyl)-2,3-dihydro-1H-pyrrolo[3,2-c]-quinoline;
(2) 6,8-dimethoxy-4-methyl-1-(2-phenoxyethyl)-2,3-dihydro-1H-pyrrolo[3,2-c]quinoline;
(3) 1-cyclopropyl-6,8-dimethoxy-4-methyl-2,3-dihydro-1H-pyrrolo[3,2-c]-quinoline;
(4) 8-methoxy-4-methyl-1-(4-phenoxyphenyl)-2,3-dihydro-1H-pyrrolo[3,2-c]-quinoline;
(5) {2-[4-(8-methoxy-4-methyl-2,3-dihydro-1H-pyrrolo[3,2-c]quinolin-1-yl)-phenoxy]ethyl}dimethylamine;
(6) 8-methoxy-4-methyl-1-[4-(pyridin-3-yloxy)phenyl]-2,3-dihydro-1H-pyrrolo[3,2-c]quinoline;
(7) 4-methyl-8-phenoxy-1-phenyl-2,3-dihydro-1H-pyrrolo[3,2-c]-quinoline;
(8) 1-benzyl-4-methyl-8-phenoxy-2,3-dihydro-1H-pyrrolo[3,2-c]-quinoline;
(9) 1-(indan-2-yl)-4-methyl-8-phenoxy-2,3-dihydro-1H-pyrrolo[3,2-c]quinoline;
(10) 4-methyl-6-phenoxy-1-phenyl-2,3-dihydro-1H-pyrrolo[3,2-c]-quinoline;
(11) 1-benzyl-4-methyl-6-phenoxy-2,3-dihydro-1H-pyrrolo[3,2-c]-quinoline;
(12) 1-(indan-2-yl)-4-methyl-6-phenoxy-2,3-dihydro-1H-pyrrolo[3,2-c]quinoline;
(13) 4-methyl-1-(2-phenylethyl)-8-phenoxy-2,3-dihydro-1H-pyrrolo[3,2-c]-quinoline;
(14) 8-methoxy-4-methyl-1-(2-phenylethyl)-2,3-dihydro-1H-pyrrolo[3,2-c]-quinolin-6-ol;
(15) 1-(1-benzyl-piperidin-4-yl)-4-methyl-8-phenoxy-2,3-dihydro-1H-pyrrolo[3,2-c]quinoline;
(16) 1-(indan-1-yl)-4-methyl-8-phenoxy-2,3-dihydro-1H-pyrrolo[3,2-c]quinoline;
(17) 1-(benzodioxan-2-ylmethyl)-4-methyl-8-phenoxy-2,3-dihydro-1H-pyrrolo[3,2-c]quinoline;
(18) 4-methyl-8-phenoxy-1-(1,2,3,4-tetrahydronaphthalen-1-yl)-2,3-dihydro-1H-pyrrolo[3,2-c]quinoline;
(19) 1-cyclohexyl-4-methyl-8-phenoxy-2,3-dihydro-1H-pyrrolo[3,2-c]quinoline;
(20) 8-ethoxy-4-methyl-1-(4-phenoxyphenyl)-2,3-dihydro-1H-pyrrolo[3,2-c]-quinoline;
(21) 1-(4-methoxyphenyl)-4-methyl-8-phenoxy-2,3-dihydro-1H-pyrrolo[3,2-c]-quinoline;
(22) 4-methyl-1-(2-methylphenyl)methyl-8-phenoxy-2,3-dihydro-1H-pyrrolo[3,2-c]-quinoline;
(23) 4-methyl-8-phenoxy-1-(4-iso-propylphenyl)-2,3-dihydro-1H-pyrrolo[3,2-c]-quinoline;
(24) 4-methyl-8-phenoxy-1-(1-phenylethyl)-2,3-dihydro-1H-pyrrolo[3,2-c]quinoline;

(25) 8-methoxy-4-methyl-1-(2-phenylethyl)-2,3-dihydro-1H-pyrrolo[3,2-c]-quinoline;
(26) 6,8-dimethoxy-1-(4-hydroxyphenyl)-4-methyl-2,3-dihydro-1H-pyrrolo[3,2-c]quinoline;
(27) 6,8-dimethoxy-1-(3-hydroxyphenyl)-4-methyl-2,3-dihydro-1H-pyrrolo[3,2-c]quinoline;
(28) 6,8-dimethoxy-1-(3-hydroxy-5-methylphenyl)-4-methyl-2,3-dihydro-1H-pyrrolo[3,2-c]quinoline;
(30) 8-methoxy-1-(4-methoxyphenyl)-4-methyl-2,3-dihydro-1H-pyrrolo[3,2-c]-quinoline;
(31) 8-trifluoromethoxy-1-(4-phenoxyphenyl)-4-methyl-2,3-dihydro-1H-pyrrolo[3,2-c]quinoline;
(32) 6,8-dimethoxy-4-methyl-1-[4-(pyridin-3-yloxy)phenyl]-2,3-dihydro-1H-pyrrolo[3,2-c]quinoline;
(33) 1-benzyl-6,8-dimethoxy-4-methyl-2,3-dihydro-1H-pyrrolo[3,2-c]quinoline;
(34) 6,8-dimethoxy-4-methyl-1-(2-phenylethyl)-2,3-dihydro-1H-pyrrolo[3,2-c]quinoline;
(35) 4-methyl-1-(2-phenylethyl)-8-trifluoromethoxy-2,3-dihydro-1H-pyrrolo[3,2-c]quinoline;
(36) 6,8-dimethoxy-1-(indan-1-yl)-4-methyl-2,3-dihydro-1H-pyrrolo[3,2-c]quinoline;
(37) 6,8-dimethoxy-4-methyl-1-[(6-phenoxy)pyridin-3-yl]-2,3-dihydro-1H-pyrrolo[3,2-c]quinoline;
(38) 6,8-dimethoxy-1-[(6-methoxy)pyridin-3-yl]-4-methyl-2,3-dihydro-1H-pyrrolo[3,2-c]quinoline;
(39) 1-(benzodioxol-5-ylmethyl)-6,8-dimethoxy-4-methyl-2,3-dihydro-1H-pyrrolo[3,2-c]quinoline;
(40) 6,8-dimethoxy-4-methyl-1-(3-methylbutyl)-2,3-dihydro-1H-pyrrolo[3,2-c]quinoline;
(41) 1-cyclopropylmethyl-6,8-dimethoxy-4-methyl-2,3-dihydro-1H-pyrrolo[3,2-c]quinoline;
(43) 8-methoxy-4-methyl-1-(1,2,3,4-tetrahydronaphthalen-1-yl)-2,3-dihydro-1H-pyrrolo[3,2-c]quinoline;
(49) 1-{4-[2-(N,N-dimethylamino)ethoxy]phenyl}-4-methyl-8-phenoxy-2,3-dihydro-1H-pyrrolo[3,2-c]quinoline;
(50) 1-[4-(4-fluorophenoxy)phenyl]-8-methoxy-4-methyl-2,3-dihydro-1H-pyrrolo[3,2-c]quinoline;
(51) 1-(benzodioxan-2-ylmethyl)-8-methoxy-4-methyl-2,3-dihydro-1H-pyrrolo[3,2-c]quinoline;
(52) 1-cyclohexyl-8-methoxy-4-methyl-2,3-dihydro-1H-pyrrolo[3,2-c]quinoline;
(53) 8-methoxy-4-methyl-1-phenyl-2,3-dihydro-1H-pyrrolo[3,2-c]quinoline;
(54) 4-methyl-8-phenoxy-1-[4-(3-pyridyl)phenyl]-2,3-dihydro-1H-pyrrolo[3,2-c]quinoline;
(55) 4-methyl-8-phenoxy-1-[2-(3-pyridyl)ethyl]-2,3-dihydro-1H-pyrrolo[3,2-c]quinoline;
(56) 4-methyl-8-phenoxy-1-(2-pyridylmethyl)-2,3-dihydro-1H-pyrrolo[3,2-c]quinoline;
(57) 4-methyl-1-(5-methylpyrazin-2-ylmethyl)-8-phenoxy-2,3-dihydro-1H-pyrrolo[3,2-c]quinoline;
(62) 1-[3-(4-methyl-8-phenoxy-2,3-dihydro-1H-pyrrolo[3,2-c]quinolin-1-yl)propyl]-pyrrolidin-2-one;
(63) 4-methyl-8-phenoxy-1-[2-(2-pyridyl)ethyl]-2,3-dihydro-1H-pyrrolo[3,2-c]quinoline;
(64) ethyl 3-(8-methoxy-4-methyl-2,3-dihydro-1H-pyrrolo[3,2-c]quinoline-1-yl)propionate;
(65) ethyl 4-(4-methyl-8-phenoxy-2,3-dihydro-1H-pyrrolo[3,2-c]quinoline-1-yl)butanoate;
(66) methyl 4-(4-methyl-8-phenoxy-2,3-dihydro-1H-pyrrolo[3,2-c]quinoline-1-yl)butanoate;
(67) ethyl (4-methyl-8-phenoxy-2,3-dihydro-1H-pyrrolo[3,2-c]quinoline-1-yl)acetate;
(68) 4-methyl-1-(1-methylpiperidin-4-yl)-8-phenoxy-2,3-dihydro-1H-pyrrolo[3,2-c]quinoline;
(69) 1-(1-benzylpyrrolidin-3-yl)-8-methoxy-4-methyl-2,3-dihydro-1H-pyrrolo[3,2-c]quinoline;
(70) methyl 3-(4-methyl-8-phenoxy-2,3-dihydro-1H-pyrrolo[3,2-c]quinoline-1-yl)propionate;
(71) 1-((S)-indan-1-yl)-4-methyl-8-phenoxy-2,3-dihydro-1H-pyrrolo[3,2-c]-quinoline;
(72) 1-((R)-indan-1-yl)-4-methyl-8-phenoxy-2,3-dihydro-1H-pyrrolo[3,2-c]-quinoline;
(73) 1-(3-methoxypropyl)-4-methyl-8-phenoxy-2,3-dihydro-1H-pyrrolo[3,2-c]-quinoline;
(74) 4-methyl-8-phenoxy-1-(tetrahydrofuran-2-ylmethyl)-2,3-dihydro-1H-pyrrolo[3,2-c]quinoline;
(75) 1-[2-(4-chlorophenyl)ethyl]-4-methyl-8-phenoxy-2,3-dihydro-1H-pyrrolo[3,2-c]quinoline;
(76) 1-[2-(4-methoxyphenyl)ethyl]-4-methyl-8-phenoxy-2,3-dihydro-1H-pyrrolo[3,2-c]quinoline;
(77) 4-methyl-8-phenoxy-1-(2-phenylpropyl)-2,3-dihydro-1H-pyrrolo[3,2-c]-quinoline;
(80) 8-phenoxy-1-(2-phenylethyl)-2,3-dihydro-1H-pyrrolo[3,2-c]-quinoline;
(82) 8-methoxy-4-methyl-1-[4-(4-methylpiperazin-1-yl)-3-fluorophenyl]-2,3-dihydro-1H-pyrrolo[3,2-c]quinoline;
(83) 4-methyl-8-phenylamino-1-(2-phenylethyl)-2,3-dihydro-1H-pyrrolo[3,2-c]-quinoline, or a pharmaceutically-acceptable salt thereof, wherein the microbial infection is a bacterial infection.

3. A method of treating a mammal afflicted with a disease comprising administering to said afflicted mammal an effective amount of a compound, wherein the compound is selected from the group consisting of:

(1) 6,8-dimethoxy-4-methyl-1-(3-phenoxyphenyl)-2,3-dihydro-1H-pyrrolo[3,2-c]-quinoline;
(2) 6,8-dimethoxy-4-methyl-1-(2-phenoxyethyl)-2,3-dihydro-1H-pyrrolo[3,2-c]-quinoline;
(3) 1-cyclopropyl-6,8-dimethoxy-4-methyl-2,3-dihydro-1H-pyrrolo[3,2-c]-quinoline;
(4) 8-methoxy-4-methyl-1-(4-phenoxyphenyl)-2,3-dihydro-1H-pyrrolo[3,2-c]-quinoline;
(5) {2-[4-(8-methoxy-4-methyl-2,3-dihydro-1H-pyrrolo[3,2-c]quinolin-1-yl)-phenyoxy]ethyl}dimethylamine;
(6) 8-methoxy-4-methyl-1-[4-(pyridin-3-yloxy)phenyl]-2,3-dihydro-1H-pyrrolo[3,2-c]quinoline;
(7) 4-methyl-8-phenoxy-1-phenyl-2,3-dihydro-1H-pyrrolo[3,2-c]quinoline;
(8) 1-benzyl-4-methyl-8-phenoxy-2,3-dihydro-1H-pyrrolo[3,2-c]quinoline;
(9) 1-(indan-2-yl)-4-methyl-8-phenoxy-2,3-dihydro-1H-pyrrolo[3,2-c]quinoline;
(10) 4-methyl-6-phenoxy-1-phenyl-2,3-dihydro-1H-pyrrolo[3,2-c]quinoline;
(11) 1-benzyl-4-methyl-6-phenoxy-2,3-dihydro-1H-pyrrolo[3,2-c]quinoline;
(12) 1-(indan-2-yl)-4-methyl-6-phenoxy-2,3-dihydro-1H-pyrrolo[3,2-c]quinoline;
(13) 4-methyl-1-(2-phenylethyl)-8-phenoxy-2,3-dihydro-1H-pyrrolo[3,2-c]-quinoline;
(14) 8-methoxy-4-methyl-1-(2-phenylethyl)-2,3-dihydro-1H-pyrrolo[3,2-c]-quinolin-6-ol;
(15) 1-(1-benzyl-piperidin-4-yl)-4-methyl-8-phenoxy-2,3-dihydro-1H-pyrrolo[3,2-c]quinoline;
(16) 1-(indan-1-yl)-4-methyl-8-phenoxy-2,3-dihydro-1H-pyrrolo[3,2-c]quinoline;
(17) 1-(benzodioxan-2-ylmethyl)-4-methyl-8-phenoxy-2,3-dihydro-1H-pyrrolo[3,2-c]quinoline;
(18) 4-methyl-8-phenoxy-1-(1,2,3,4-tetrahydronaphthalen-1-yl)-2,3-dihydro-1H-pyrrolo[3,2-c]quinoline;

(19) 1-cyclohexyl-4-methyl-8-phenoxy-2,3-dihydro-1H-pyrrolo[3,2-c]quinoline;
(20) 8-ethoxy-4-methyl-1-(4-phenoxyphenyl)-2,3-dihydro-1H-pyrrolo[3,2-c]-quinoline;
(21) 1-(4-methoxyphenyl)-4-methyl-8-phenoxy-2,3-dihydro-1H-pyrrolo[3,2-c]-quinoline;
(22) 4-methyl-1-(2-methylphenyl)methyl-8-phenoxy-2,3-dihydro-1H-pyrrolo[3,2-c]-quinoline;
(23) 4-methyl-8-phenoxy-1-(4-iso-propylphenyl)-2,3-dihydro-1H-pyrrolo[3,2-c]quinoline;
(24) 4-methyl-8-phenoxy-1-(1-phenylethyl)-2,3-dihydro-1H-pyrrolo[3,2-c]-quinoline;
(25) 8-methoxy-4-methyl-1-(2-phenylethyl)-2,3-dihydro-1H-pyrrolo[3,2-c]-quinoline;
(26) 6,8-dimethoxy-1-(4-hydroxyphenyl)-4-methyl-2,3-dihydro-1H-pyrrolo[3,2-c]quinoline;
(27) 6,8-dimethoxy-1-(3-hydroxyphenyl)-4-methyl-2,3-dihydro-1H-pyrrolo[3,2-c]quinoline;
(28) 6,8-dimethoxy-1-(3-hydroxy-5-methylphenyl)-4-methyl-2,3-dihydro-1H-pyrrolo[3,2-c]quinoline;
(30) 8-methoxy-1-(4-methoxyphenyl)-4-methyl-2,3-dihydro-1H-pyrrolo[3,2-c]-quinoline;
(31) 8-trifluoromethoxy-1-(4-phenoxyphenyl)-4-methyl-2,3-dihydro-1H-pyrrolo[3,2-c]quinoline;
(32) 6,8-dimethoxy-4-methyl-1-[4-(pyridin-3-yloxy)phenyl]-2,3-dihydro-1H-pyrrolo[3,2-c]quinoline;
(33) 1-benzyl-6,8-dimethoxy-4-methyl-2,3-dihydro-1H-pyrrolo[3,2-c]quinoline;
(34) 6,8-dimethoxy-4-methyl-1-(2-phenylethyl)-2,3-dihydro-1H-pyrrolo[3,2-c]quinoline;
(35) 4-methyl-1-(2-phenylethyl)-8-trifluoromethoxy-2,3-dihydro-1H-pyrrolo[3,2-c]quinoline;
(36) 6,8-dimethoxy-1-(indan-1-yl)-4-methyl-2,3-dihydro-1H-pyrrolo[3,2-c]quinoline;
(37) 6,8-dimethoxy-4-methyl-1-[(6-phenoxy)pyridin-3-yl]-2,3-dihydro-1H-pyrrolo[3,2-c]quinoline;
(38) 6,8-dimethoxy-1-[(6-methoxy)pyridin-3-yl]-4-methyl-2,3-dihydro-1H-pyrrolo[3,2-c]quinoline;
(39) 1-(benzodioxol-5-ylmethyl)-6,8-dimethoxy-4-methyl-2,3-dihydro-1H-pyrrolo[3,2-c]quinoline;
(40) 6,8-dimethoxy-4-methyl-1-(3-methylbutyl)-2,3-dihydro-1H-pyrrolo[3,2-c]quinoline;
(41) 1-cyclopropylmethyl-6,8-dimethoxy-4-methyl-2,3-dihydro-1H-pyrrolo[3,2-c]quinoline;
(43) 8-methoxy-4-methyl-1-(1,2,3,4-tetrahydronaphthalen-1-yl)-2,3-dihydro-1H-pyrrolo[3,2-c]quinoline;
(49) 1-{4-[2-(N,N-dimethylamino)ethoxy]phenyl}-4-methyl-8-phenoxy-2,3-dihydro-1H-pyrrolo[3,2-c]quinoline;
(50) 1-[4-(4-fluorophenoxy)phenyl]-8-methoxy-4-methyl-2,3-dihydro-1H-pyrrolo[3,2-c]quinoline;
(51) 1-(benzodioxan-2-ylmethyl)-8-methoxy-4-methyl-2,3-dihydro-1H-pyrrolo[3,2-c]quinoline;
(52) 1-cyclohexyl-8-methoxy-4-methyl-2,3-dihydro-1H-pyrrolo[3,2-c]quinoline;
(53) 8-methoxy-4-methyl-1-phenyl-2,3-dihydro-1H-pyrrolo[3,2-c]quinoline;
(54) 4-methyl-8-phenoxy-1-[4-(3-pyridyl)phenyl]-2,3-dihydro-1H-pyrrolo[3,2-c]-quinoline;
(55) 4-methyl-8-phenoxy-1-[2-(3-pyridyl)ethyl]-2,3-dihydro-1H-pyrrolo[3,2-c]-quinoline;
(56) 4-methyl-8-phenoxy-1-(2-pyridylmethyl)-2,3-dihydro-1H-pyrrolo[3,2-c]-quinoline;
(57) 4-methyl-1-(5-methylpyrazin-2-ylmethyl)-8-phenoxy-2,3-dihydro-1H-pyrrolo[3,2-c]quinoline;
(62) 1-[3-(4-methyl-8-phenoxy-2,3-dihydro-1H-pyrrolo[3,2-c]quinolin-1-yl)propyl]-pyrrolidin-2-one;
(63) 4-methyl-8-phenoxy-1-[2-(2-pyridyl)ethyl]-2,3-dihydro-1H-pyrrolo[3,2-c]-quinoline;
(64) ethyl 3-(8-methoxy-4-methyl-2,3-dihydro-1H-pyrrolo[3,2-c]quinoline-1-yl)propionate;
(65) ethyl 4-(4-methyl-8-phenoxy-2,3-dihydro-1H-pyrrolo[3,2-c]quinoline-1-yl)butanoate;
(66) methyl 4-(4-methyl-8-phenoxy-2,3-dihydro-1H-pyrrolo[3,2-c]quinoline-1-yl)butanoate;
(67) ethyl (4-methyl-8-phenoxy-2,3-dihydro-1H-pyrrolo[3,2-c]quinoline-1-yl)acetate;
(68) 4-methyl-1-(1-methylpiperidin-4-yl)-8-phenoxy-2,3-dihydro-1H-pyrrolo[3,2-c]quinoline;
(69) 1-(1-benzylpyrrolidin-3-yl)-8-methoxy-4-methyl-2,3-dihydro-1H-pyrrolo[3,2-c]quinoline;
(70) methyl 3-(4-methyl-8-phenoxy-2,3-dihydro-1H-pyrrolo[3,2-c]quinoline-1-yl)propionate;
(71) 1-((S)-indan-1-yl)-4-methyl-8-phenoxy-2,3-dihydro-1H-pyrrolo[3,2-c]-quinoline;
(72) 1-((R)-indan-1-yl)-4-methyl-8-phenoxy-2,3-dihydro-1H-pyrrolo[3,2-c]-quinoline;
(73) 1-(3-methoxypropyl)-4-methyl-8-phenoxy-2,3-dihydro-1H-pyrrolo[3,2-c]-quinoline;
(74) 4-methyl-8-phenoxy-1-(tetrahydrofuran-2-ylmethyl)-2,3-dihydro-1H-pyrrolo[3,2-c]quinoline;
(75) 1-[2-(4-chlorophenyl)ethyl]-4-methyl-8-phenoxy-2,3-dihydro-1H-pyrrolo[3,2-c]quinoline;
(76) 1-[2-(4-methoxyphenyl)ethyl]-4-methyl-8-phenoxy-2,3-dihydro-1H-pyrrolo[3,2-c]quinoline;
(77) 4-methyl-8-phenoxy-1-(2-phenylpropyl)-2,3-dihydro-1H-pyrrolo[3,2-c]-quinoline;
(80) 8-phenoxy-1-(2-phenylethyl)-2,3-dihydro-1H-pyrrolo[3,2-c]quinoline;
(82) 8-methoxy-4-methyl-1-[4-(4-methylpiperazin-1-yl)-3-fluorophenyl]-2,3-dihydro-1H-pyrrolo[3,2-c]quinoline;
(83) 4-methyl-8-phenylamino-1-(2-phenylethyl)-2,3-dihydro-1H-pyrrolo[3,2-c]-quinoline; or a pharmaceutically-acceptable salt thereof, wherein said disease is an infection with *S. aureus*, *Enterococcus*, *Pseudomonas*, MRSA, *Klebsiella aerogrenes*, *E. coli*, *Streptococcus pneumoniae*, *Streptococcus pyogenes* Group A Streptococci, Group B streptococci (*Streptococcus agalactiae*), *Streptococcus viridans*, *Haemophilus influenzae*, or *M. tuberculosis*.

4. The method of killing clinically latent bacterial microorganisms according to claim 1, wherein the clinically latent bacterial microorganism is selected from the group consisting of *E. coli*, *Enterococcus*, *Staph. aureus*, *Streptococcus* and *Mycobacterium tuberculosis*.

5. The method of treatment according to claim 2, wherein the bacterial infection is caused by *E. coli*, *Enterococcus*, *Staph. aureus*, *Streptococcus* or *Mycobacterium tuberculosis*.

6. A method of killing clinically latent fungal microorganisms in a mammal comprising administering a compound to a mammal in need thereof, wherein the compound is selected from the group consisting of:
(1) 6,8-dimethoxy-4-methyl-1-(3-phenoxyphenyl)-2,3-dihydro-1H-pyrrolo[3,2-c]-quinoline;
(2) 6,8-dimethoxy-4-methyl-1-(2-phenoxyethyl)-2,3-dihydro-1H-pyrrolo[3,2-c]-quinoline;
(3) 1-cyclopropyl-6,8-dimethoxy-4-methyl-2,3-dihydro-1H-pyrrolo[3,2-c]-quinoline;
(4) 8-methoxy-4-methyl-1-(4-phenoxyphenyl)-2,3-dihydro-1H-pyrrolo[3,2-c]-quinoline;
(5) {2-[4-(8-methoxy-4-methyl-2,3-dihydro-1H-pyrrolo[3,2-c]quinolin-1-yl)-phenyoxy]ethyl}dimethylamine;

(6) 8-methoxy-4-methyl-1-[4-(pyridin-3-yloxy)phenyl]-2,3-dihydro-1H-pyrrolo[3,2-c]quinoline;
(7) 4-methyl-8-phenoxy-1-phenyl-2,3-dihydro-1H-pyrrolo[3,2-c]quinoline;
(8) 1-benzyl-4-methyl-8-phenoxy-2,3-dihydro-1H-pyrrolo[3,2-c]quinoline;
(9) 1-(indan-2-yl)-4-methyl-8-phenoxy-2,3-dihydro-1H-pyrrolo[3,2-c]quinoline;
(10) 4-methyl-6-phenoxy-1-phenyl-2,3-dihydro-1H-pyrrolo[3,2-c]quinoline;
(11) 1-benzyl-4-methyl-6-phenoxy-2,3-dihydro-1H-pyrrolo[3,2-c]quinoline;
(12) 1-(indan-2-yl)-4-methyl-6-phenoxy-2,3-dihydro-1H-pyrrolo[3,2-c]quinoline;
(13) 4-methyl-1-(2-phenylethyl)-8-phenoxy-2,3-dihydro-1H-pyrrolo[3,2-c]-quinoline;
(14) 8-methoxy-4-methyl-1-(2-phenylethyl)-2,3-dihydro-1H-pyrrolo[3,2-c]-quinolin-6-ol;
(15) 1-(1-benzyl-piperidin-4-yl)-4-methyl-8-phenoxy-2,3-dihydro-1H-pyrrolo[3,2-c]quinoline;
(16) 1-(indan-1-yl)-4-methyl-8-phenoxy-2,3-dihydro-1H-pyrrolo[3,2-c]quinoline;
(17) 1-(benzodioxan-2-ylmethyl)-4-methyl-8-phenoxy-2,3-dihydro-1H-pyrrolo[3,2-c]quinoline;
(18) 4-methyl-8-phenoxy-1-(1,2,3,4-tetrahydronaphthalen-1-yl)-2,3-dihydro-1H-pyrrolo[3,2-c]quinoline;
(19) 1-cyclohexyl-4-methyl-8-phenoxy-2,3-dihydro-1H-pyrrolo[3,2-c]quinoline;
(20) 8-ethoxy-4-methyl-1-(4-phenoxyphenyl)-2,3-dihydro-1H-pyrrolo[3,2-c]-quinoline;
(21) 1-(4-methoxyphenyl)-4-methyl-8-phenoxy-2,3-dihydro-1H-pyrrolo[3,2-c]-quinoline;
(22) 4-methyl-1-(2-methylphenyl)methyl-8-phenoxy-2,3-dihydro-1H-pyrrolo[3,2-c]-quinoline;
(23) 4-methyl-8-phenoxy-1-(4-iso-propylphenyl)-2,3-dihydro-1H-pyrrolo[3,2-c]-quinoline;
(24) 4-methyl-8-phenoxy-1-(1-phenylethyl)-2,3-dihydro-1H-pyrrolo[3,2-c]-quinoline;
(25) 8-methoxy-4-methyl-1-(2-phenylethyl)-2,3-dihydro-1H-pyrrolo[3,2-c]quinoline;
(26) 6,8-dimethoxy-1-(4-hydroxyphenyl)-4-methyl-2,3-dihydro-1H-pyrrolo[3,2-c]quinoline;
(27) 6,8-dimethoxy-1-(3-hydroxyphenyl)-4-methyl-2,3-dihydro-1H-pyrrolo[3,2-c]quinoline;
(28) 6,8-dimethoxy-1-(3-hydroxy-5-methylphenyl)-4-methyl-2,3-dihydro-1H-pyrrolo[3,2-c]quinoline;
(30) 8-methoxy-1-(4-methoxyphenyl)-4-methyl-2,3-dihydro-1H-pyrrolo[3,2-c]-quinoline;
(31) 8-trifluoromethoxy-1-(4-phenoxyphenyl)-4-methyl-2,3-dihydro-1H-pyrrolo[3,2-c]quinoline;
(32) 6,8-dimethoxy-4-methyl-1-[4-(pyridin-3-yloxy)phenyl]-2,3-dihydro-1H-pyrrolo[3,2-c]quinoline;
(33) 1-benzyl-6,8-dimethoxy-4-methyl-2,3-dihydro-1H-pyrrolo[3,2-c]quinoline;
(34) 6,8-dimethoxy-4-methyl-1-(2-phenylethyl)-2,3-dihydro-1H-pyrrolo[3,2-c]quinoline;
(35) 4-methyl-1-(2-phenylethyl)-8-trifluoromethoxy-2,3-dihydro-1H-pyrrolo[3,2-c]quinoline;
(36) 6,8-dimethoxy-1-(indan-1-yl)-4-methyl-2,3-dihydro-1H-pyrrolo[3,2-c]quinoline;
(37) 6,8-dimethoxy-4-methyl-1-[(6-phenoxy)pyridin-3-yl]-2,3-dihydro-1H-pyrrolo[3,2-c]quinoline;
(38) 6,8-dimethoxy-1-[(6-methoxy)pyridin-3-yl]-4-methyl-2,3-dihydro-1H-pyrrolo[3,2-c]quinoline;
(39) 1-(benzodioxol-5-ylmethyl)-6,8-dimethoxy-4-methyl-2,3-dihydro-1H-pyrrolo[3,2-c]quinoline;
(40) 6,8-dimethoxy-4-methyl-1-(3-methylbutyl)-2,3-dihydro-1H-pyrrolo[3,2-c]quinoline;
(41) 1-cyclopropylmethyl-6,8-dimethoxy-4-methyl-2,3-dihydro-1H-pyrrolo[3,2-c]quinoline;
(43) 8-methoxy-4-methyl-1-(1,2,3,4-tetrahydronaphthalen-1-yl)-2,3-dihydro-1H-pyrrolo[3,2-c]quinoline;
(49) 1-{4-[2-(N,N-dimethylamino)ethoxy]phenyl}-4-methyl-8-phenoxy-2,3-dihydro-1H-pyrrolo[3,2-c]quinoline;
(50) 1-[4-(4-fluorophenoxy)phenyl]-8-methoxy-4-methyl-2,3-dihydro-1H-pyrrolo[3,2-c]quinoline;
(51) 1-(benzodioxan-2-ylmethyl)-8-methoxy-4-methyl-2,3-dihydro-1H-pyrrolo[3,2-c]quinoline;
(52) 1-cyclohexyl-8-methoxy-4-methyl-2,3-dihydro-1H-pyrrolo[3,2-c]quinoline;
(53) 8-methoxy-4-methyl-1-phenyl-2,3-dihydro-1H-pyrrolo[3,2-c]quinoline;
(54) 4-methyl-8-phenoxy-1-[4-(3-pyridyl)phenyl]-2,3-dihydro-1H-pyrrolo[3,2-c]-quinoline;
(55) 4-methyl-8-phenoxy-1-[2-(3-pyridyl)ethyl]-2,3-dihydro-1H-pyrrolo[3,2-c]quinoline;
(56) 4-methyl-8-phenoxy-1-(2-pyridylmethyl)-2,3-dihydro-1H-pyrrolo[3,2-c]-quinoline;
(57) 4-methyl-1-(5-methylpyrazin-2-ylmethyl)-8-phenoxy-2,3-dihydro-1H-pyrrolo[3,2-c]quinoline;
(62) 1-[3-(4-methyl-8-phenoxy-2,3-dihydro-1H-pyrrolo[3,2-c]quinolin-1-yl)propyl]-pyrrolidin-2-one;
(63) 4-methyl-8-phenoxy-1-[2-(2-pyridyl)ethyl]-2,3-dihydro-1H-pyrrolo[3,2-c]quinoline;
(64) ethyl 3-(8-methoxy-4-methyl-2,3-dihydro-1H-pyrrolo[3,2-c]quinoline-1-yl)propionate;
(65) ethyl 4-(4-methyl-8-phenoxy-2,3-dihydro-1H-pyrrolo[3,2-c]quinoline-1-yl)butanoate;
(66) methyl 4-(4-methyl-8-phenoxy-2,3-dihydro-1H-pyrrolo[3,2-c]quinoline-1-yl)butanoate;
(67) ethyl (4-methyl-8-phenoxy-2,3-dihydro-1H-pyrrolo[3,2-c]quinoline-1-yl)acetate;
(68) 4-methyl-1-(1-methylpiperidin-4-yl)-8-phenoxy-2,3-dihydro-1H-pyrrolo[3,2-c]quinoline;
(69) 1-(1-benzylpyrrolidin-3-yl)-8-methoxy-4-methyl-2,3-dihydro-1H-pyrrolo[3,2-c]quinoline;
(70) methyl 3-(4-methyl-8-phenoxy-2,3-dihydro-1H-pyrrolo[3,2-c]quinoline-1-yl)propionate;
(71) 1-((S)-indan-1-yl)-4-methyl-8-phenoxy-2,3-dihydro-1H-pyrrolo[3,2-c]-quinoline;
(72) 1-((R)-indan-1-yl)-4-methyl-8-phenoxy-2,3-dihydro-1H-pyrrolo[3,2-c]-quinoline;
(73) 1-(3-methoxypropyl)-4-methyl-8-phenoxy-2,3-dihydro-1H-pyrrolo[3,2-c]-quinoline;
(74) 4-methyl-8-phenoxy-1-(tetrahydrofuran-2-ylmethyl)-2,3-dihydro-1H-pyrrolo[3,2-c]quinoline;
(75) 1-[2-(4-chlorophenyl)ethyl]-4-methyl-8-phenoxy-2,3-dihydro-1H-pyrrolo[3,2-c]quinoline;
(76) 1-[2-(4-methoxyphenyl)ethyl]-4-methyl-8-phenoxy-2,3-dihydro-1H-pyrrolo[3,2-c]quinoline;
(77) 4-methyl-8-phenoxy-1-(2-phenylpropyl)-2,3-dihydro-1H-pyrrolo[3,2-c]quinoline;
(80) 8-phenoxy-1-(2-phenylethyl)-2,3-dihydro-1H-pyrrolo[3,2-c]quinoline;
(82) 8-methoxy-4-methyl-1-[4-(4-methylpiperazin-1-yl)-3-fluorophenyl]-2,3-dihydro-1H-pyrrolo[3,2-c]quinoline;
(83) 4-methyl-8-phenylamino-1-(2-phenylethyl)-2,3-dihydro-1H-pyrrolo[3,2-c]-quinoline; or a pharmaceutically-acceptable salt thereof, and wherein the clinically latent microorganisms are associated with a fungal infection caused by *Candida*.

7. The method of killing clinically latent microorganisms according to claim 6, wherein the fungal infection is caused by *Candida albicans*.

8. A method of treating a microbial infection in a mammal, comprising administering to a mammal in need thereof an effective amount of a compound, wherein the compound is selected from the group consisting of:

(1) 6,8-dimethoxy-4-methyl-1-(3-phenoxyphenyl)-2,3-dihydro-1H-pyrrolo[3,2-c]-quinoline;
(2) 6,8-dimethoxy-4-methyl-1-(2-phenoxyethyl)-2,3-dihydro-1H-pyrrolo[3,2-c]-quinoline;
(3) 1-cyclopropyl-6,8-dimethoxy-4-methyl-2,3-dihydro-1H-pyrrolo[3,2-c]-quinoline;
(4) 8-methoxy-4-methyl-1-(4-phenoxyphenyl)-2,3-dihydro-1H-pyrrolo[3,2-c]-quinoline;
(5) {2-[4-(8-methoxy-4-methyl-2,3-dihydro-1H-pyrrolo[3,2-c]quinolin-1-yl)-phenyoxy]ethyl}dimethylamine;
(6) 8-methoxy-4-methyl-1-[4-(pyridin-3-yloxy)phenyl]-2,3-dihydro-1H-pyrrolo[3,2-c]-quinoline;
(7) 4-methyl-8-phenoxy-1-phenyl-2,3-dihydro-1H-pyrrolo[3,2-c]quinoline;
(8) 1-benzyl-4-methyl-8-phenoxy-2,3-dihydro-1H-pyrrolo[3,2-c]quinoline;
(9) 1-(indan-2-yl)-4-methyl-8-phenoxy-2,3-dihydro-1H-pyrrolo[3,2-c]quinoline;
(10) 4-methyl-6-phenoxy-1-phenyl-2,3-dihydro-1H-pyrrolo[3,2-c]quinoline;
(11) 1-benzyl-4-methyl-6-phenoxy-2,3-dihydro-1H-pyrrolo[3,2-c]quinoline;
(12) 1-(indan-2-yl)-4-methyl-6-phenoxy-2,3-dihydro-1H-pyrrolo[3,2-c]quinoline;
(13) 4-methyl-1-(2-phenylethyl)-8-phenoxy-2,3-dihydro-1H-pyrrolo[3,2-c]-quinoline;
(14) 8-methoxy-4-methyl-1-(2-phenylethyl)-2,3-dihydro-1H-pyrrolo[3,2-c]-quinolin-6-ol;
(15) 1-(1-benzyl-piperidin-4-yl)-4-methyl-8-phenoxy-2,3-dihydro-1H-pyrrolo[3,2-c]quinoline;
(16) 1-(indan-1-yl)-4-methyl-8-phenoxy-2,3-dihydro-1H-pyrrolo[3,2-c]quinoline;
(17) 1-(benzodioxan-2-ylmethyl)-4-methyl-8-phenoxy-2,3-dihydro-1H-pyrrolo[3,2-c]quinoline;
(18) 4-methyl-8-phenoxy-1-(1,2,3,4-tetrahydronaphthalen-1-yl)-2,3-dihydro-1H-pyrrolo[3,2-c]quinoline;
(19) 1-cyclohexyl-4-methyl-8-phenoxy-2,3-dihydro-1H-pyrrolo[3,2-c]quinoline;
(20) 8-ethoxy-4-methyl-1-(4-phenoxyphenyl)-2,3-dihydro-1H-pyrrolo[3,2-c]-quinoline;
(21) 1-(4-methoxyphenyl)-4-methyl-8-phenoxy-2,3-dihydro-1H-pyrrolo[3,2-c]-quinoline;
(22) 4-methyl-1-(2-methylphenyl)methyl-8-phenoxy-2,3-dihydro-1H-pyrrolo[3,2-c]-quinoline;
(23) 4-methyl-8-phenoxy-1-(4-iso-propylphenyl)-2,3-dihydro-1H-pyrrolo[3,2-c]-quinoline;
(24) 4-methyl-8-phenoxy-1-(1-phenylethyl)-2,3-dihydro-1H-pyrrolo[3,2-c]-quinoline;
(25) 8-methoxy-4-methyl-1-(2-phenylethyl)-2,3-dihydro-1H-pyrrolo[3,2-c]-quinoline;
(26) 6,8-dimethoxy-1-(4-hydroxyphenyl)-4-methyl-2,3-dihydro-1H-pyrrolo[3,2-c]-quinoline;
(27) 6,8-dimethoxy-1-(3-hydroxyphenyl)-4-methyl-2,3-dihydro-1H-pyrrolo[3,2-c]-quinoline;
(28) 6,8-dimethoxy-1-(3-hydroxy-5-methylphenyl)-4-methyl-2,3-dihydro-1H-pyrrolo[3,2-c]quinoline;
(30) 8-methoxy-1-(4-methoxyphenyl)-4-methyl-2,3-dihydro-1H-pyrrolo[3,2-c]-quinoline;
(31) 8-trifluoromethoxy-1-(4-phenoxyphenyl)-4-methyl-2,3-dihydro-1H-pyrrolo[3,2-c]quinoline;
(32) 6,8-dimethoxy-4-methyl-1-[4-(pyridin-3-yloxy)phenyl]-2,3-dihydro-1H-pyrrolo[3,2-c]quinoline;
(33) 1-benzyl-6,8-dimethoxy-4-methyl-2,3-dihydro-1H-pyrrolo[3,2-c]quinoline;
(34) 6,8-dimethoxy-4-methyl-1-(2-phenylethyl)-2,3-dihydro-1H-pyrrolo[3,2-c]quinoline;
(35) 4-methyl-1-(2-phenylethyl)-8-trifluoromethoxy-2,3-dihydro-1H-pyrrolo[3,2-c]quinoline;
(36) 6,8-dimethoxy-1-(indan-1-yl)-4-methyl-2,3-dihydro-1H-pyrrolo[3,2-c]quinoline;
(37) 6,8-dimethoxy-4-methyl-1-[(6-phenoxy)pyridin-3-yl]-2,3-dihydro-1H-pyrrolo[3,2-c]quinoline;
(38) 6,8-dimethoxy-1-[(6-methoxy)pyridin-3-yl]-4-methyl-2,3-dihydro-1H-pyrrolo[3,2-c]quinoline;
(39) 1-(benzodioxol-5-ylmethyl)-6,8-dimethoxy-4-methyl-2,3-dihydro-1H-pyrrolo[3,2-c]quinoline;
(40) 6,8-dimethoxy-4-methyl-1-(3-methylbutyl)-2,3-dihydro-1H-pyrrolo[3,2-c]quinoline;
(41) 1-cyclopropylmethyl-6,8-dimethoxy-4-methyl-2,3-dihydro-1H-pyrrolo[3,2-c]quinoline;
(43) 8-methoxy-4-methyl-1-(1,2,3,4-tetrahydronaphthalen-1-yl)-2,3-dihydro-1H-pyrrolo[3,2-c]quinoline;
(49) 1-{4-[2-(N,N-dimethylamino)ethoxy]phenyl}-4-methyl-8-phenoxy-2,3-dihydro-1H-pyrrolo[3,2-c]quinoline;
(50) 1-[4-(4-fluorophenoxy)phenyl]-8-methoxy-4-methyl-2,3-dihydro-1H-pyrrolo[3,2-c]quinoline;
(51) 1-(benzodioxan-2-ylmethyl)-8-methoxy-4-methyl-2,3-dihydro-1H-pyrrolo[3,2-c]quinoline;
(52) 1-cyclohexyl-8-methoxy-4-methyl-2,3-dihydro-1H-pyrrolo[3,2-c]quinoline;
(53) 8-methoxy-4-methyl-1-phenyl-2,3-dihydro-1H-pyrrolo[3,2-c]quinoline;
(54) 4-methyl-8-phenoxy-1-[4-(3-pyridyl)phenyl]-2,3-dihydro-1H-pyrrolo[3,2-c]-quinoline;
(55) 4-methyl-8-phenoxy-1-[2-(3-pyridyl)ethyl]-2,3-dihydro-1H-pyrrolo[3,2-c]-quinoline;
(56) 4-methyl-8-phenoxy-1-(2-pyridylmethyl)-2,3-dihydro-1H-pyrrolo[3,2-c]-quinoline;
(57) 4-methyl-1-(5-methylpyrazin-2-ylmethyl)-8-phenoxy-2,3-dihydro-1H-pyrrolo[3,2-c]quinoline;
(62) 1-[3-(4-methyl-8-phenoxy-2,3-dihydro-1H-pyrrolo[3,2-c]quinolin-1-yl)propyl]-pyrrolidin-2-one;
(63) 4-methyl-8-phenoxy-1-[2-(2-pyridyl)ethyl]-2,3-dihydro-1H-pyrrolo[3,2-c]-quinoline;
(64) ethyl 3-(8-methoxy-4-methyl-2,3-dihydro-1H-pyrrolo[3,2-c]quinoline-1-yl)propionate;
(65) ethyl 4-(4-methyl-8-phenoxy-2,3-dihydro-1H-pyrrolo[3,2-c]quinoline-1-yl)butanoate;
(66) methyl 4-(4-methyl-8-phenoxy-2,3-dihydro-1H-pyrrolo[3,2-c]quinoline-1-yl)butanoate;
(67) ethyl (4-methyl-8-phenoxy-2,3-dihydro-1H-pyrrolo[3,2-c]quinoline-1-yl)acetate;
(68) 4-methyl-1-(1-methylpiperidin-4-yl)-8-phenoxy-2,3-dihydro-1H-pyrrolo[3,2-c]quinoline;
(69) 1-(1-benzylpyrrolidin-3-yl)-8-methoxy-4-methyl-2,3-dihydro-1H-pyrrolo[3,2-c]quinoline;
(70) methyl 3-(4-methyl-8-phenoxy-2,3-dihydro-1H-pyrrolo[3,2-c]quinoline-1-yl)propionate;
(71) 1-((S)-indan-1-yl)-4-methyl-8-phenoxy-2,3-dihydro-1H-pyrrolo[3,2-c]-quinoline;
(72) 1-((R)-indan-1-yl)-4-methyl-8-phenoxy-2,3-dihydro-1H-pyrrolo[3,2-c]quinoline;
(73) 1-(3-methoxypropyl)-4-methyl-8-phenoxy-2,3-dihydro-1H-pyrrolo[3,2-c]quinoline;
(74) 4-methyl-8-phenoxy-1-(tetrahydrofuran-2-ylmethyl)-2,3-dihydro-1H-pyrrolo[3,2-c]quinoline;

(75) 1-[2-(4-chlorophenyl)ethyl]-4-methyl-8-phenoxy-2,3-dihydro-1H-pyrrolo[3,2-c]quinoline;
(76) 1-[2-(4-methoxyphenyl)ethyl]-4-methyl-8-phenoxy-2,3-dihydro-1H-pyrrolo[3,2-c]quinoline;
(77) 4-methyl-8-phenoxy-1-(2-phenylpropyl)-2,3-dihydro-1H-pyrrolo[3,2-c]-quinoline;
(80) 8-phenoxy-1-(2-phenylethyl)-2,3-dihydro-1H-pyrrolo[3,2-c]quinoline;
(82) 8-methoxy-4-methyl-1-[4-(4-methylpiperazin-1-yl)-3-fluorophenyl]-2,3-dihydro-1H-pyrrolo[3,2-c]quinoline;
(83) 4-methyl-8-phenylamino-1-(2-phenylethyl)-2,3-dihydro-1H-pyrrolo[3,2-c]-quinoline; or a pharmaceutically-acceptable salt thereof,
wherein the microbial infection is a fungal infection caused by *Candida*.

9. The method of treating a microbial infection according to claim 8, wherein the fungal infection is caused by *Candida albicans*.

* * * * *